(12) United States Patent
Horvath et al.

(10) Patent No.: US 7,638,304 B2
(45) Date of Patent: Dec. 29, 2009

(54) HYBRID FUSION PROTEIN TRANSCRIPTION REGULATOR TO INDUCE INTERFERON TARGET GENE EXPRESSION

(75) Inventors: Curt M. Horvath, Wilmette, IL (US); Joe F. Lau, New York, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 446 days.

(21) Appl. No.: 10/492,043

(22) PCT Filed: Oct. 3, 2002

(86) PCT No.: PCT/US02/31768

§ 371 (c)(1),
(2), (4) Date: Sep. 23, 2004

(87) PCT Pub. No.: WO03/031575

PCT Pub. Date: Apr. 17, 2003

(65) Prior Publication Data

US 2005/0019306 A1  Jan. 27, 2005

Related U.S. Application Data

(60) Provisional application No. 60/327,476, filed on Oct. 5, 2001, provisional application No. 60/352,777, filed on Jan. 29, 2002.

(51) Int. Cl.
| | |
|---|---|
| C12P 21/02 | (2006.01) |
| C12N 5/00 | (2006.01) |
| C07K 14/00 | (2006.01) |
| A01K 38/21 | (2006.01) |
| A61K 39/00 | (2006.01) |

(52) U.S. Cl. .............. 435/69.5; 435/69.1; 435/325; 530/351; 424/85.4; 424/192.1

(58) Field of Classification Search .......... None
See application file for complete search history.

(56) References Cited

U.S. PATENT DOCUMENTS 6,087,478 A  7/2000  Vinkemeier .......... 530/350
6,348,586 B1  2/2002  Chang et al. .......... 536/23.72
7,087,726 B2 *  8/2006  Chuntharapai et al. . 530/388.23

FOREIGN PATENT DOCUMENTS

WO  WO 02/068614 A2  9/2002

OTHER PUBLICATIONS

Lin (1994) J. Biol. Chem. 269:17542-17549.*
Schang (2002) J. Antimicrob. Chemother. 50:779-792.*
Andrei (2006) Antivir. Res. 71:96-107.*
Kraus et al. (2003) J. Biol. Chem. 278:13033-13038.*
Honda et al. (2006) Nat. Rev. Immunol. 6:644-658.*
Tanaka et al. (2000) Seminars Cancer Biol. 10:73-81.*
Torchilin et al. (2003) DDT 8:259-266.*
Wei-Chu Au et al. Identification Of A Member Of The Interferon Regulatory Factor Family That Binds To The Interferon-stimulated Response Element And Activates Expression Of Interferon-induced Genes *Pro.Nat'l. Acad. Sci. USA*, vol. 92 pp. 11657-11661, Dec. 1995.
Hans A. R. Bluyssen et al., "Stat2 Is A Transcriptional Activator That Requires Sequence-specific Contacts Provided By Stat1 and p48 for Stable Interaction With DNA" *The Journal Of Biological Chemistry*, vol. 272, No. 7 pp. 4600-4605, Feb. 14, 1997.

* cited by examiner

*Primary Examiner*—Janet Epps-Smith
(74) *Attorney, Agent, or Firm*—Brandon T. Schurter; Locke Lord Bissell & Liddell LLP

(57) ABSTRACT

New hybrid or chimeric fusion polypeptide transcription regulators which induce interferon target gene expression are provided for use in anti-viral and anti-proliferative applications. The hybrid fusion proteins comprise the p48 interferon regulatory factor protein, or a functional portion thereof, fused to a transcriptional activation domain (TAD), or a functional portion thereof. More specifically, the p48 interferon regulatory factor protein is fused to a STAT transcriptional activation do main (TAD) (p48-STAT TAD). A particular p48-STAT TAD is p48-S2C, in which S2C is the TAD of STAT2. Another p48-TAD is p48-VP16 TAD, in which p48 is fused to the transcriptional activation domain of the VP16 protein of Herpes Simplex Virus (HSV). The p48-TAD nucleic acid sequences and encoded polypeptides can be employed for anti-viral treatment and for the treatment of cancers, tumors and neoplastic diseases.

5 Claims, 30 Drawing Sheets

Nucleic Acid Sequence of the Hybrid p48-S2C Fusion Protein

SEQ ID NO: 1 atggcatcaggcagggcacgctgcacccgaaaactccggaactgggtggtggagcaagtggagag
tgggcagtttcccggagtgtgctgggatgatacagctaagaccatgttccggattccctggaaacatgc
aggcaagcaggacttccgggaggaccaggatgctgccttcttcaaggcctgggcaatatttaaggga
aagtataaggagggggacacaggaggtccagctgtctggaagactcgcctgcgctgtgcactcaac
aagagttctgaatttaaggaggttcctgagaggggccgcatggatgttgctgagccctacaaggtgtat
cagttgctgccaccaggaatcgtctctggccagccagggactcagaaagtaccatcaaagcgacagc
acagttctgtgtcctctgagaggaaggaggaagaggatgccatgcagaactgcacactcagtccctct
gtgctccaggactccctcaataatgaggaggaggggggccagtgggggagcagtccattcagacatt
gggagcagcagcagcagcagcagccctgagccacaggaagttacagacacaactgaggcccccctt
tcaaggggatcagaggtccctggagtttctgcttcctccagagccagactactcactgctgctcaccttc
atctacaacgggcgcgtggtgggcgaggcccaggtgcaaagcctggattgccgccttgtggctgag
ccctcaggctctgagagcagcatggagcaggtgctgttccccaagcctggcccactggagcccacg
cagcgcctgctgagccagcttgagaggggcatcctagtggccagcaaccccccgaggcctcttcgtg
cagcgcctttgccccatccccatctcctggaatgcaccccaggctccacctgggccaggcccgcatct
gctgcccagcaacgagtgcgtggagctcttcagaaccgcctacttctgcagagacttggtcaggtactt
tcagggcctgggccccccaccgaagttccaggtaacactgaatttctgggaagagagccatggctcc
agccatactccacagaatcttatcacagtgaagatggagcaggcctttgcccgatacttgctggagca
gactccagagcagcaggcagccattctgtccctggtggggccagagctagagtctgtgctggagtc
cactctggagcctgtgatagagcccacactatgcatggtatcacaaacagtgccagagccaga
ccaaggacctgtatcacagccagtgccagagccagatttgccctgtgatctgagacatttgaac
actgagccaatggaaatcttcagaaactgtgtaaagattgaagaaatcatgccgaatggtgacc
cactgttggctggccagaacaccgtggatgaggtttacgtctcccgccccagccacttctacact
gatggaccettgatgccttctgacttc

FIG. 1

Amino Acid Sequence of the Hybrid p48-S2C Fusion Protein

SEQ ID NO: 2

MASGRARCTRKLRNWVVEQVESGQFPGVCWDDTAKTMFRIPWKHAGKQ
DFREDQDAAFFKAWAIFKGKYKEGDTGGPAVWKTRLRCALNKSSEFKEVP
ERGRMDVAEPYKVYQLLPPGIVSGQPGTQKVPSKRQHSSVSSERKEEEDAM
QNCTLSPSVLQDSLNNEEEGASGGAVHSDIGSSSSSSSPEPQEVTDTTEAPFQ
GDQRSLEFLLPPEPDYSLLLTFIYNGRVVGEAQVQSLDCRLVAEPSGSESSM
EQVLFPKPGPLEPTQRLLSQLERGILVASNPRGLFVQRLCPIPISWNAPQAPP
GPGPHLLPSNECVELFRTAYFCRDLVRYFQGLGPPPKFQVTLNFWEESHGSS
HTPQNLITVKMEQAFARYLLEQTPEQQAAILSLVGPELESVLESTLEPVIEP
TLCMVSQTVPEPDQGPVSQPVPEPDLPCDLRHLNTEPMEIFRNCVKIEEI
MPNGDPLLAGQNTVDEVYVSRPSHFYTDGPLMPSDF

FIG. 2

Nucleic Acid Sequence of p48

SEQ ID NO: 4 atggcatcaggcagggcacgctgcacccgaaaactccggaactgggtggtggagcaagtggagag
tgggcagtttcccggagtgtgctgggatgatacagctaagaccatgttccggattccctggaaacatgc
aggcaagcaggacttccgggaggaccaggatgctgccttcttcaaggcctgggcaatatttaaggga
aagtataaggagggggacacaggaggtccagctgtctggaagactcgcctgcgctgtgcactcaac
aagagttctgaatttaaggaggttcctgagaggggccgcatggatgttgctgagccctacaaggtgtat
cagttgctgccaccaggaatcgtctctggccagccagggactcagaaagtaccatcaaagcgacagc
acagttctgtgtcctctgagaggaaggaggaagaggatgccatgcagaactgcacactcagtccctct
gtgctccaggactccctcaataatgaggaggaggggccagtggggagcagtccattcagacatt
gggagcagcagcagcagcagcagccctgagccacaggaagttacagacacaactgaggccccctt
tcaaggggatcagaggtccctggagtttctgcttcctccagagccagactactcactgctgctcaccttc
atctacaacgggcgcgtggtgggcgaggcccaggtgcaaagcctggattgccgccttgtggctgag
ccctcaggctctgagagcagcatggagcaggtgctgttccccaagcctggcccactggagcccacg
cagcgcctgctgagccagcttgagaggggcatcctagtggccagcaacccccgaggcctcttcgtg
cagcgcctttgccccatccccatctcctggaatgcaccccaggctccacctgggccaggcccgcatct
gctgcccagcaacgagtgcgtggagctcttcagaaccgcctacttctgcagagacttggtcaggtactt
tcagggcctgggccccccaccgaagttccaggtaacactgaatttctgggaagagagccatggctcc
agccatactccacagaatcttatcacagtgaagatggagcaggcctttgcccgatacttgctggagca
gactccagagcagcaggcagccattctgtccctggtg

FIG. 6

Amino Acid Sequence of p48

SEQ ID NO: 5

MASGRARCTRKLRNWVVEQVESGQFPGVCWDDTAKTMFRIPWKHAGKQ
DFREDQDAAFFKAWAIFKGKYKEGDTGGPAVWKTRLRCALNKSSEFKEVP
ERGRMDVAEPYKVYQLLPPGIVSGQPGTQKVPSKRQHSSVSSERKEEEDAM
QNCTLSPSVLQDSLNNEEEGASGGAVHSDIGSSSSSSSPEPQEVTDTTEAPFQ
GDQRSLEFLLPPEPDYSLLLTFIYNGRVVGEAQVQSLDCRLVAEPSGSESSM
EQVLFPKPGPLEPTQRLLSQLERGILVASNPRGLFVQRLCPIPISWNAPQAPP
GPGPHLLPSNECVELFRTAYFCRDLVRYFQGLGPPPKFQVTLNFWEESHGSS
HTPQNLITVKMEQAFARYLLEQTPEQQAAILSLV

FIG. 7

Nucleic Acid Sequence of STAT2 TAD (S2C)

SEQ ID NO: 6 gggccagagctagagtctgtgctggagtccactctggagcctgtgatagagcccacactatgcatggt
atcacaaacagtgccagagccagaccaaggacctgtatcacagccagtgccagagccagatttgcc
ctgtgatctgagacatttgaacactgagccaatggaaatcttcagaaactgtgtaaagattgaagaaatc
atgccgaatggtgacccactgttggctggccagaacaccgtggatgaggtttacgtctcccgccccag
ccacttctacactgatggacccttgatgccttctgacttc

FIG. 8

Amino Acid Sequence of STAT2 TAD (S2C)

SEQ ID NO: 7

GPELESVLESTLEPVIEPTLCMVSQTVPEPDQGPVSQPVPEPDLPCDLRHLNT
EPMEIFRNCVKIEEIMPNGDPLLAGQNTVDEVYVSRPSHFYTDGPLMPSDF

FIG. 9

ANTI-IFN STRATEGIES OF VIRUSES

| Virus | Product | Target |
|---|---|---|
| Adenovirus | E1A | STATs; CBP |
|  | VA RNA | PKR |
| EBV | EBNA2 |  |
|  | EBER | dsRNA |
| Vaccinia | K3L | dsRNA |
|  | B18R | sIFNR |
|  | E3L | dsRNA |
| Herpes | γ1 34.5 | EIF2α |
|  | US11 | PKR |
|  | VIRF | ISRErepressor |
| Hepatitis B | Terminal |  |
| Papilloma | E6 | IRF3 |
|  | E7 | ISGF3γ |
| HIV1 | TAT | PKR |
| Hepatitis C | NS5A | PKR |
|  | E2 | PKR |
| Rotavirus C | NSP3 | dsRNA |
| Influenza A | NS1 | dsRNA, IRF3 |
| Sendai | C | STAT1 |
| SV5 | V | STAT1 |
| Other Paramyxos | V | STAT1, 2 |

FIG. 10

| Application | Viral Target | Description |
|---|---|---|
| | *Examples* | |
| Gene therapy in vivo | Hepatitis C | Liver-targeted expression of p48-TAD (by viral vector system) will rescue cells. Liver's regenerative capacity will aid in recovery of healthy liver |
| Gene therapy ex vivo | HIV, EBV | Coupled with the power of autologous bone marrow transplant. Bone marrow is isolated from patient, transfected with p48-TAD expression system, and returned to patient after radiation therapy. |
| Topical application | Herpes, Varicella, Kaposi's Sarcoma (KHSV) | A liposome encapsulated expression plasmid for p48-TAD is applied to infected area by a cream. The DNA is taken up by the skin cells and produces the IFN response limiting virus replication. |
| Prophylactic anti-viral by aerosol | Influenza Virus, Rhinovirus, Respiratory Syncytial virus, Parainfluenza | For Respiratory viruses, a liposome encapsulated expression plasmid for p48-TAD is inhaled as an aerosol. The DNA is taken up by lung epithelial cells and produces the IFN response |
| Health Care Workers, Hot Zone Outbreaks, Biological Warfare | West Nile Virus Nipah, Hendra, Ebola, Rift Valley Fever, Hemorrhagic Fevers, Encephalitis Virus | Aerosol or other delivery methods used to protect health care workers or soldiers during fatal outbreaks of virulent viral pathogens. Could similarly be used for protection of workers at risk during more common outbreaks like measles or mumps. |
| Veterinary and Agricultural use in Livestock, Poultry, Farming | Foot-and-mouth disease, Flock house viruses relevant to the Meat and Poultry Industry | Aerosol or other delivery methods used to protect animals from harmful and costly viral infections. |

FIG. 11

Nucleic Acid Sequence of STAT1 TAD (S1C)

SEQ ID NO: 14 cacccttctagacttcagaccacagacaacctgctccccatgtctcctgaggagtttgacgaggtgtctc
ggatagtgggctctgtagaattcgacagtatgatgaacacagta

FIG. 12

Amino Acid Sequence of STAT1 TAD (S1C)

SEQ ID NO: 15

HPSRLQTTDNLLPMSPEEFDEVSRIVGSVEFDSMMNTV

FIG. 13

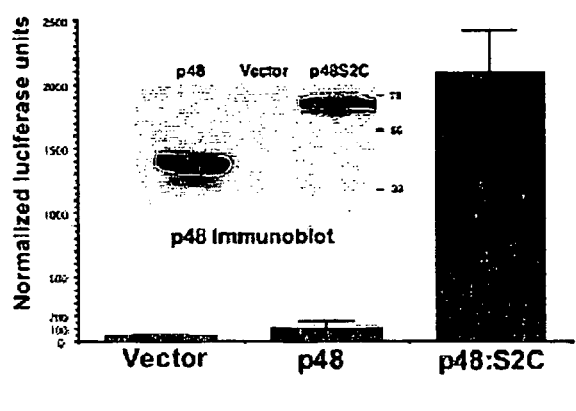 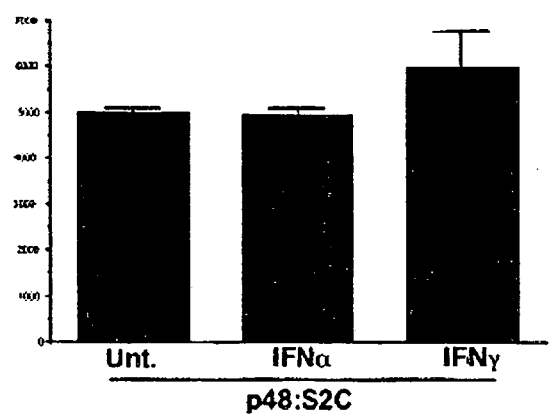
FIG. 14A FIG. 14B

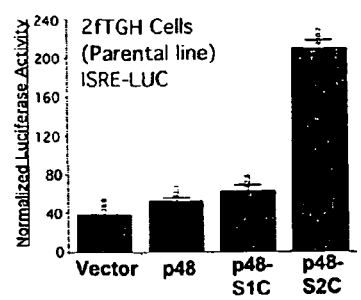 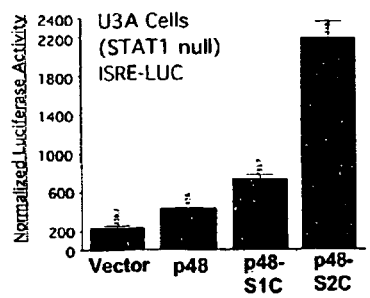 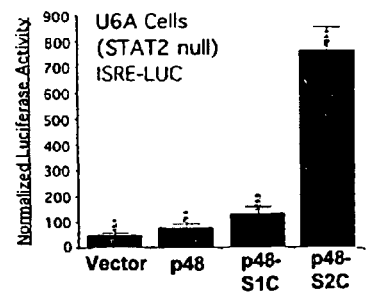
FIG. 15A  FIG. 15B  FIG. 15C
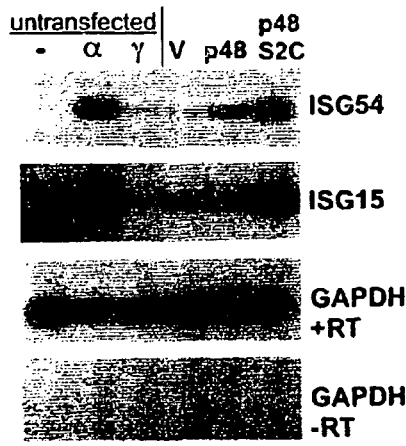
FIG. 16

FIG. 19A
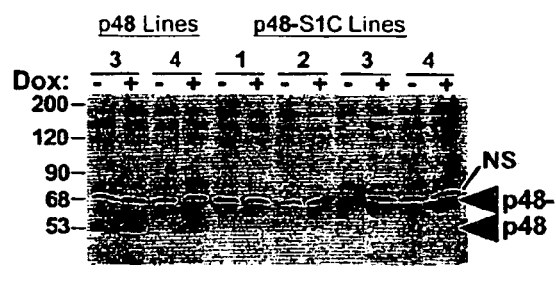
FIG. 19B
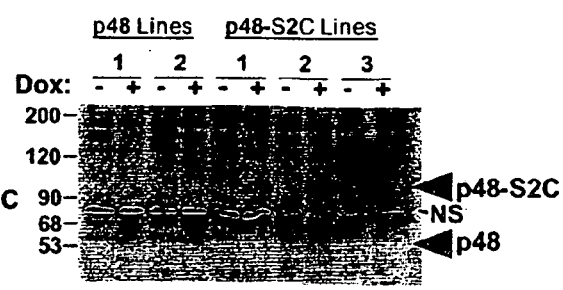
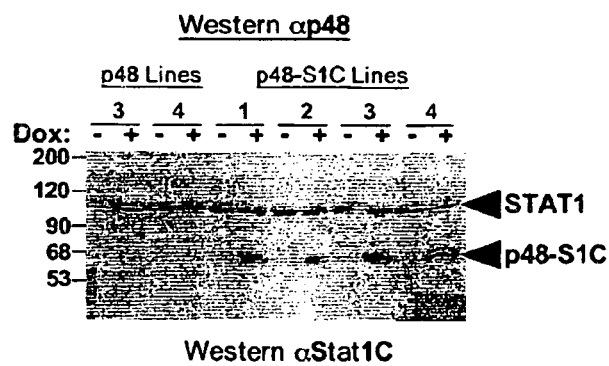
FIG. 19C

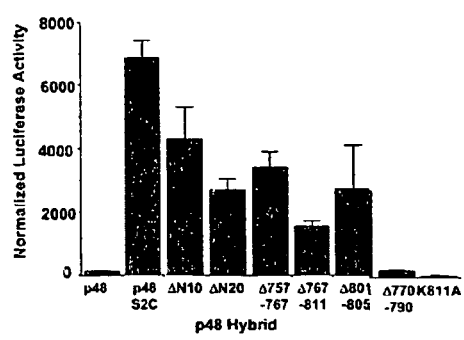 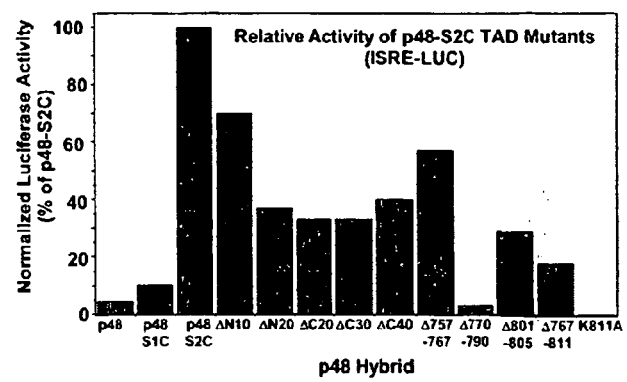
FIG. 22A
FIG. 22B

Nucleic Acid Sequence of STAT2
SEQ ID NO: 16 atggcgcagtgggaaatgctgcagaatcttgacagccccttcaggatcagctgcaccagctttactcgcacag
cctcctgcctgtggacattcgacagtacttggctgtctggattgaagaccagaactggcaggaagctgcacttg
ggagtgatgattccaaggctaccatgctattcttccacttcttggatcagctgaactatgagtgtggccgttgcag
ccaggacccagagtccttgttgctgcagcacaatttgcggaaattctgccgggacattcagccctttcccagg
atcctacccagttggctgagatgatctttaacctccttctggaagaaaaagaattttgatccaggctcagaggg
cccaattggaacaaggagagccagttctcgaaacacctgtggagagccagcaacatgagattaatcccgga
tcctggatttaagggctatgatggagaagctggtaaaatccatcagccaactgaaagaccagcaggatgtcttc
tgcttccgatataagatccaggccaagggaagacaccctctctggaccccatcagaccaaagagcagaag
attctgcaggaaactctcaatgaactggacaaaaggagaaaggaggtgctggatgcctccaaagcactgcta
ggccgattaactaccctaatcgagctactgctgccaaagttggaggagtggaaggcccagcagcaaaaagcc
tgcatcagagctcccattgaccacgggttggaacagctggagacatggttcacagctggagcaaagctgttgtt
tcacctgaggcagctgctgaaggagctgaagggactgagttgcctggttagctatcaggatgaccctctgacc
aaaggggtggacctacgcaacgcccaggtcacagagttgctacagcgtctgctccacagagcctttgtggta
gaaacccagccctgcatgccccaaactccccatcgaccctcatcctcaagactggcagcaagttcaccgtcc
gaacaaggctgctggtgagactccaggaaggcaatgagtcactgactgtggaagtctccattgacaggaatc
ctcctcaattacaaggcttccggaagttcaacattctgacttcaaaccagaaaactttgaccccgagaagggg
cagagtcagggtttgatttgggactttggttacctgactctggtggagcaacgttcaggtggttcaggaaaggg
cagcaataaggggccactaggtgtgacagaggaactgcacatcatcagcttcacggtcaaatatacctaccag
ggtctgaagcaggagctgaaaacggacaccctccctgtggtgattatttccaacatgaaccagctctcaattgc
ctgggcttcagttctctggttcaatttgctcagcccaaaccttcagaaccagcagttcttctccaaccccccaag
gcccctggagcttgctgggccctgctctcagttggcagttctcctcctatgttggccgaggcctcaactcagac
cagctgagcatgctgagaaacaagctgttcgggcagaactgtaggactgaggatccattattgtcctgggctg
acttcactaagcgagagagccctcctggcaagttaccattctggacatggctggacaaaattctggagttggta
catgaccacctgaaggatctctggaatgatggacgcatcatgggctttgtgagtcggagccaggagcgccgg
ctgctgaagaagaccatgtctggcaccttctactgcgcttcagtgaatcgtcagaagggggcattacctgctcc
tgggtggagcaccaggatgatgacaaggtgctcatctactctgtgcaaccgtacacgaaggaggtgctgcagt
cactcccgctgactgaaatcatccgccattaccagttgctcactgaggagaatatacctgaaaacccactgcgc
ttcctctatccccgaatccccgggatgaagcttttgggtgctactaccaggagaaagttaatctccaggaacg
gaggaaatacctgaaacacaggctcattgtggtctctaatagacaggtggatgaactgcaacaaccgctggag
cttaagccagagccagagctggagtcattagagctggaactagggctggtgccagagccagagctcagcct
ggacttagagccactgctgaaggcagggctggatctggggccagagctagagtctgtgctggagtccactct
ggagcctgtgatagagcccacactatgcatggtatcacaaacagtgccagagccagaccaaggacctgtatc
acagccagtgccagagccagatttgccctgtgatctgagacatttgaacactgagccaatggaaatcttcagaa
actgtgtaaagattgaagaaatcatgccgaatggtgacccactgttggctggccagaacaccgtggatgaggtt
tacgtctcccgccccagccacttctacactgatggacccttgatgccttctgacttctag

Amino Acid Sequence of STAT2

SEQ ID NO: 17

MAQWEMLQNLDSPFQDQLHQLYSHSLLPVDIRQYLAVWIEDQNWQEAAL
GSDDSKATMLFFHFLDQLNYECGRCSQDPESLLLQHNLRKFCRDIQPFSQDP
TQLAEMIFNLLLEEKRILIQAQRAQLEQGEPVLETPVESQQHEIESRILDLRA
MMEKLVKSISQLKDQQDVFCFRYKIQAKGKTPSLDPHQTKEQKILQETLNE
LDKRRKEVLDASKALLGRLTTLIELLLPKLEEWKAQQQKACIRAPIDHGLEQ
LETWFTAGAKLLFHLRQLLKELKGLSCLVSYQDDPLTKGVDLRNAQVTELL
QRLLHRAFVVETQPCMPQTPHRPLILKTGSKFTVRTRLLVRLQEGNESLTVE
VSIDRNPPQLQGFRKFNILTSNQKTLTPEKGQSQGLIWDFGYLTLVEQRSGG
SGKGSNKGPLGVTEELHIISFTVKYTYQGLKQELKTDTLPVVIISNMNQLSIA
WASVLWFNLLSPNLQNQQFFSNPPKAPWSLLGPALSWQFSSYVGRGLNSD
QLSMLRNKLFGQNCRTEDPLLSWADFTKRESPPGKLPFWTWLDKILELVHD
HLKDLWNDGRIMGFVSRSQERRLLKKTMSGTFLLRFSESSEGGITCSWVEH.
QDDDKVLIYSVQPYTKEVLQSLPLTEIIRHYQLLTEENIPENPLRFLYPRIPRD
EAFGCYYQEKVNLQERRKYLKHRLIVVSNRQVDELQQPLELKPEPELESLEL
ELGLVPEPELSLDLEPLLKAGLDLGPELESVLESTLEPVIEPTLCMVSQTVPEP
DQGPVSQPVPEPDLPCDLRHLNTEPMEIFRNCVKIEEIMPNGDPLLAGQNTV
DEVYVSRPSHFYTDGPLMPSDF

FIG. 25

Nucleic Acid Sequence of STAT1
SEQ ID NO: 18 atgtctcagtggtacgaacttcagcagcttgactcaaaattcctggagcaggttcaccagctttatgatg
acagttttcccatggaaatcagacagtacctggcacagtggttagaaaagcaagactgggagcacgct
gccaatgatgtttcatttgccaccatccgttttcatgacctcctgtcacagctggatgatcaatatagtcgc
ttttctttggagaataacttcttgctacagcataacataaggaaaagcaagcgtaatcttcaggataatttt
caggaagacccaatccagatgtctatgatcatttacagctgtctgaaggaagaaaggaaaattctggaa
aacgcccagagatttaatcaggctcagtcggggaatattcagagcacagtgatgttagacaaacagaa
agagcttgacagtaaagtcagaaatgtgaaggacaaggttatgtgtatagagcatgaaatcaagagcc
tggaagatttacaagatgaatatgacttcaaatgcaaaaccttgcagaacagagaacacgagaccaat
ggtgtggcaaagagtgatcagaaacaagaacagctgttactcaagaagatgtatttaatgcttgacaat
aagagaaaggaagtagttcacaaaataatagagttgctgaatgtcactgaacttacccagaatgccctg
attaatgatgaactagtggagtggaagcggagacagcagagcgcctgtattggggggccgcccaat
gcttgcttggatcagctgcagaactggttcactatagttgcggagagtctgcagcaagttcggcagcag
cttaaaaagttggaggaattggaacagaaatacacctacgaacatgaccctatcacaaaaaacaaaca
agtgttatgggaccgcaccttcagtcttttccagcagctcattcagagctcgtttgtggtggaaagacag
ccctgcatgccaacgcaccctcagaggccgctggtcttgaagacaggggtccagttcactgtgaagtt
gagactgttggtgaaattgcaagagctgaattataatttgaaagtcaaagtcttatttgataaagatgtga
atgagagaaatacagtaaaaggatttaggaagttcaacatttggggcacgcacacaaaagtgatgaac
atggaggagtccaccaatggcagtctggcggctgaatttcggcacctgcaattgaaagaacagaaaa
atgctggcaccagaacgaatgagggtcctctcatcgttactgaagagcttcactcccttagttttgaaac
ccaattgtgccagcctggtttggtaattgacctcgagacgacctctctgcccgttgtggtgatctccaac
gtcagccagctcccgagcggttgggcctccatcctttggtacaacatgctggtggcggaacccagga
atctgtccttcttcctgactccaccatgtgcacgatgggctcagctttcagaagtgctgagttggcagtttt
cttctgtcaccaaaagaggtctcaatgtggaccagctgaacatgttgggagagaagcttcttggtccta
acgccagccccgatggtctcattccgtggacgaggttttgtaaggaaaatataaatgataaaaatttttcc
cttctggctttggattgaaagcatcctagaactcattaaaaaacacctgctccctctctggaatgatgggt
gcatcatgggcttcatcagcaaggagcgagagcgtgccctgttgaaggaccagcagccggggacct
tcctgctgcggttcagtgagagctcccgggaaggggccatcacattcacatgggtggagcggtccca
gaacggaggcgaacctgacttccatgcggttgaaccctacacgaagaaagaactttctgctgttacttt
ccctgacatcattcgcaattacaaagtcatggctgctgagaatattcctgagaatcccctgaagtatctgt
atccaaatattgacaaagaccatgcctttggaaagtattactccaggccaaaggaagcaccagagcca
atggaacttgatggccctaaaggaactggatatatcaagactgagttgatttctgtgtctgaagttcaccc
ttctagacttcagaccacagacaacctgctccccatgtctcctgaggagtttgacgaggtgtctcggata
gtgggctctgtagaattcgacagtatgatgaacacagtatag

FIG. 26

Amino Acid Sequence of STAT1

SEQ ID NO: 19

MSQWYELQQLDSKFLEQVHQLYDDSFPMEIRQYLAQWLEKQDWEHAAND
VSFATIRFHDLLSQLDDQYSRFSLENNFLLQHNIRKSKRNLQDNFQEDPIQM
SMIIYSCLKEERKILENAQRFNQAQSGNIQSTVMLDKQKELDSKVRNVKDK
VMCIEHEIKSLEDLQDEYDFKCKTLQNREHETNGVAKSDQKQEQLLLKKM
YLMLDNKRKEVVHKIIELLNVTELTQNALINDELVEWKRRQQSACIGGPPN
ACLDQLQNWFTIVAESLQQVRQQLKKLEELEQKYTYEHDPITKNKQVLWD
RTFSLFQQLIQSSFVVERQPCMPTHPQRPLVLKTGVQFTVKLRLLVKLQELN
YNLKVKVLFDKDVNERNTVKGFRKFNILGTHTKVMNMEESTNGSLAAEFR
HLQLKEQKNAGTRTNEGPLIVTEELHSLSFETQLCQPGLVIDLETTSLPVVVI
SNVSQLPSGWASILWYNMLVAEPRNLSFFLTPPCARWAQLSEVLSWQFSSV
TKRGLNVDQLNMLGEKLLGPNASPDGLIPWTRFCKENINDKNFPFWLWIESI
LELIKKHLLPLWNDGCIMGFISKERERALLKDQQPGTFLLRFSESSREGAITF
TWVERSQNGGEPDFHAVEPYTKKELSAVTFPDIIRNYKVMAAENIPENPLK
YLYPNIDKDHAFGKYYSRPKEAPEPMELDGPKGTGYIKTELISVSEVHPSRL
QTTDNLLPMSPEEFDEVSRIVGSVEFDSMMNTV

FIG. 27

Nucleic Acid Sequence of HSV VP16 TAD

SEQ ID NO: 27 tcgacggccccccccaccgatgtcagcctgggggacgagctccacttagacggcgaggacgtggc
gatggcgcatgccgacgcgctagacgatttcgatctggacatgttgggggacggggattccccgggt
ccgggatttaccccccacgactccgcccccctacggcgctctggatatggccgacttcgactttgagca
gatgtttaccgatgcccttggaattgacgagtacggtggg

FIG. 28

Amino Acid Sequence of HSV VP16 TAD

SEQ ID NO: 28

STAPPTDVSLGDELHLDGRDYAMAHADALDDFDLDMLGDGDSPGPGFTPH
DSAPYGALDMADFEFEGHFTDALGIDEYGG

FIG. 29

Nucleic Acid Sequence of the Hybrid p48-VP16 TAD Fusion Protein

SEQ ID NO: 29 atggcatcaggcagggcacgctgcacccgaaaactccggaactgggtggtggagcaagtggagag
tgggcagtttcccggagtgtgctgggatgatacagctaagaccatgttccggattccctggaaacatgc
aggcaagcaggacttccgggaggaccaggatgctgccttcttcaaggcctgggcaatatttaaggga
aagtataaggagggggacacaggaggtccagctgtctggaagactcgcctgcgctgtgcactcaac
aagagttctgaatttaaggaggttcctgagaggggccgcatggatgttgctgagccctacaaggtgtat
cagttgctgccaccaggaatcgtctctggccagccagggactcagaaagtaccatcaaagcgacagc
acagttctgtgtcctctgagaggaaggaggaagaggatgccatgcagaactgcacactcagtccctct
gtgctccaggactccctcaataatgaggaggaggggccagtgggggagcagtccattcagacatt
gggagcagcagcagcagcagcagccctgagccacaggaagttacagacacaactgaggccccctt
tcaaggggatcagaggtccctggagtttctgcttcctccagagccagactactcactgctgctcaccttc
atctacaacgggcgcgtggtgggcgaggcccaggtgcaaagcctggattccgccttgtggctgag
ccctcaggctctgagagcagcatggagcaggtgctgttccccaagcctggcccactggagcccacg
cagcgcctgctgagccagcttgagaggggcatcctagtggccagcaaccccgaggcctcttcgtg
cagcgccttttgccccatccccatctcctggaatgcaccccaggctccacctgggccaggcccgcatct
gctgcccagcaacgagtgcgtggagctcttcagaaccgcctacttctgcagagacttggtcaggtactt
tcagggcctgggccccccaccgaagttccaggtaacactgaatttctgggaagagagccatggctcc
agccatactccacagaatcttatcacagtgaagatggagcaggcctttgcccgatacttgctggagca
gactccagagcagcaggcagccattctgtccctggtgtcgacggccccccccaccgatgtcagcct
ggggacgagctccacttagacggcgaggacgtggcgatggcgcatgccgacgcgctagacg
atttcgatctggacatgttggggacggggattccccgggtccgggatttaccccccacgactcc
gcccctacggcgctctggatatggccgacttcgactttgagcagatgtttaccgatgcccttgga
attgacgagtacggtggg

Amino Acid Sequence of the Hybrid p48-VP16 TAD Fusion Protein

SEQ ID NO: 30

MASGRARCTRKLRNWVVEQVESGQFPGVCWDDTAKTMFRIPWKHAGKQ
DFREDQDAAFFKAWAIFKGKYKEGDTGGPAVWKTRLRCALNKSSEFKEVP
ERGRMDVAEPYKVYQLLPPGIVSGQPGTQKVPSKRQHSSVSSERKEEEDAM
QNCTLSPSVLQDSLNNEEEGASGGAVHSDIGSSSSSSSPEPQEVTDTTEAPFQ
GDQRSLEFLLPPEPDYSLLLTFIYNGRVVGEAQVQSLDCRLVAEPSGSESSM
EQVLFPKPGPLEPTQRLLSQLERGILVASNPRGLFVQRLCPIPISWNAPQAPP
GPGPHLLPSNECVELFRTAYFCRDLVRYFQGLGPPPKFQVTLNFWEESHGSS
HTPQNLITVKMEQAFARYLLEQTPEQQAAILSLVSTAPPTDVSLGDELHLD
GRDYAMAHADALDDFDLDMLGDGDSPGPGFTPHDSAPYGALDMADFE
FEGHFTDALGIDEYGG

FIG. 31

| Virus[a] | Titer (pfu/ml) | | |
|---|---|---|---|
| | UNT | DOX[b] | IFN[c] |
| VSV | $9.6 \times 10^8$ | $8.7 \times 10^7$ | $4.3 \times 10^6$ |
| SV5 | $2.4 \times 10^6$ | $7.1 \times 10^4$ | $7.2 \times 10^3$ |
| HPIV2 | $2.3 \times 10^5$ | $7.7 \times 10^3$ | ND |
| HSV-1 | $2.0 \times 10^8$ | $2.6 \times 10^5$ | ND |

[a] Tet-regulated p48-S2C cell lines were treated as indicated then infected with SV5 or HPIV2 for 48 h, HSV-1 for 24 h or VSV for 18 h prior to harvest and titration of supernatants.

[b] Cells were pretreated with 1ug/ml Dox for 24h prior to infection.

[c] Cells were pretreated with 1000 U/ml IFNα for 24h prior to infection. ND, not determined.

FIG. 33

SEQUENCE LISTING

<160> NUMBER OF SEQ ID NOS: 30

<210> SEQ ID NO 1
<211> LENGTH: 1491
<212> TYPE: DNA
<213> ORGANISM: Artificial Sequence
<220> FEATURE:
<223> OTHER INFORMATION: Description of Artificial Sequence: Synthetic
      P48-S2C nucleotide sequence

<400> SEQUENCE: 1

| | | |
|---|---|---|
| atggcatcag gcagggcacg ctgcacccga aaactccgga actgggtggt ggagcaagtg | 60 |
| gagagtgggc agtttcccgg agtgtgctgg gatgatacag ctaagaccat gttccggatt | 120 |
| ccctggaaac atgcaggcaa gcaggacttc cgggaggacc aggatgctgc cttcttcaag | 180 |
| gcctgggcaa tatttaaggg aaagtataag gaggggggaca caggaggtcc agctgtctgg | 240 |
| aagactcgcc tgcgctgtgc actcaacaag agttctgaat ttaaggaggt tcctgagagg | 300 |
| ggccgcatgg atgttgctga ccctacaag gtgtatcagt tgctgccacc aggaatcgtc | 360 |
| tctggccagc cagggactca gaaagtacca tcaaagcgac agcacagttc tgtgtcctct | 420 |
| gagaggaagg aggaagagga tgccatgcag aactgcacac tcagtccctc tgtgctccag | 480 |
| gactccctca ataatgagga ggaggggggcc agtgggggag cagtccattc agacattggg | 540 |
| agcagcagca gcagcagcag ccctgagcca caggaagtta cagacacaac tgaggccccc | 600 |
| tttcaagggg atcagaggtc cctggagttt ctgcttcctc cagagccaga ctactcactg | 660 |
| ctgctcacct tcatctacaa cgggcgcgtg gtgggcgagg cccaggtgca aagcctggat | 720 |
| tgccgccttg tggctgagcc ctcaggctct gagagcagca tggagcaggt gctgttcccc | 780 |
| aagcctggcc cactggagcc cacgcagcgc ctgctgagcc agcttgagag gggcatccta | 840 |
| gtggccagca ccccgagg cctcttcgtg cagcgccttt gccccatccc catctcctgg | 900 |
| aatgcacccc aggctccacc tgggccaggc ccgcatctgc tgcccagcaa cgagtgcgtg | 960 |
| gagctcttca gaaccgccta cttctgcaga gacttggtca ggtactttca gggcctgggc | 1020 |
| cccccaccga agttccaggt aacactgaat ttctgggaag agagccatgg ctccagccat | 1080 |
| actccacaga atcttatcac agtgaagatg gagcaggcct ttgcccgata cttgctggag | 1140 |
| cagactccag agcagcaggc agccattctg tccctggtgg ggccagagct agagtctgtg | 1200 |
| ctggagtcca ctctggagcc tgtgatagag cccacactat gcatggtatc acaaacagtg | 1260 |
| ccagagccag accaaggacc tgtatcacag ccagtgccag agccagattt gccctgtgat | 1320 |
| ctgagacatt tgaacactga gccaatggaa atcttcagaa actgtgtaaa gattgaagaa | 1380 |
| atcatgccga atggtgaccc actgttggct ggccagaaca ccgtggatga ggtttacgtc | 1440 |
| tcccgcccca gccacttcta cactgatgga cccttgatgc cttctgactt c | 1491 |

<210> SEQ ID NO 2
<211> LENGTH: 497
<212> TYPE: PRT
<213> ORGANISM: Artificial Sequence
<220> FEATURE:
<223> OTHER INFORMATION: Description of Artificial Sequence: Synthetic
      P48-S2C protein sequence

```
<400> SEQUENCE: 2

Met Ala Ser Gly Arg Ala Arg Cys Thr Arg Lys Leu Arg Asn Trp Val
  1               5                  10                 15

Val Glu Gln Val Glu Ser Gly Gln Phe Pro Gly Val Cys Trp Asp Asp
             20                  25                 30

Thr Ala Lys Thr Met Phe Arg Ile Pro Trp Lys His Ala Gly Lys Gln
         35                  40                 45

Asp Phe Arg Glu Asp Gln Asp Ala Ala Phe Phe Lys Ala Trp Ala Ile
     50                  55                 60

Phe Lys Gly Lys Tyr Lys Glu Gly Asp Thr Gly Pro Ala Val Trp
 65                  70                 75                 80

Lys Thr Arg Leu Arg Cys Ala Leu Asn Lys Ser Ser Glu Phe Lys Glu
                 85                  90                 95

Val Pro Glu Arg Gly Arg Met Asp Val Ala Glu Pro Tyr Lys Val Tyr
                100                 105                110

Gln Leu Leu Pro Pro Gly Ile Val Ser Gly Pro Gly Thr Gln Lys
            115                 120                 125

Val Pro Ser Lys Arg Gln His Ser Ser Val Ser Ser Glu Arg Lys Glu
130                 135                 140

Glu Glu Asp Ala Met Gln Asn Cys Thr Leu Ser Pro Ser Val Leu Gln
145                 150                 155                160

Asp Ser Leu Asn Asn Glu Glu Gly Ala Ser Gly Gly Ala Val His
                165                 170                 175

Ser Asp Ile Gly Ser Ser Ser Ser Ser Pro Glu Pro Gln Glu
            180                 185                 190

Val Thr Asp Thr Thr Glu Ala Pro Phe Gln Gly Asp Gln Arg Ser Leu
            195                 200                 205

Glu Phe Leu Leu Pro Pro Glu Pro Asp Tyr Ser Leu Leu Thr Phe
     210                 215                 220

Ile Tyr Asn Gly Arg Val Val Gly Glu Ala Gln Val Gln Ser Leu Asp
225                 230                 235                240

Cys Arg Leu Val Ala Glu Pro Ser Gly Ser Glu Ser Ser Met Glu Gln
                245                 250                 255

Val Leu Phe Pro Lys Pro Gly Pro Leu Glu Pro Thr Gln Arg Leu Leu
                260                 265                 270

Ser Gln Leu Glu Arg Gly Ile Leu Val Ala Ser Asn Pro Arg Gly Leu
     275                 280                 285

Phe Val Gln Arg Leu Cys Pro Ile Pro Ile Ser Trp Asn Ala Pro Gln
     290                 295                 300

Ala Pro Pro Gly Pro Gly Pro His Leu Leu Pro Ser Asn Glu Cys Val
305                 310                 315                320

Glu Leu Phe Arg Thr Ala Tyr Phe Cys Arg Asp Leu Val Arg Tyr Phe
                325                 330                 335

Gln Gly Leu Gly Pro Pro Lys Phe Gln Val Thr Leu Asn Phe Trp
     340                 345                 350

Glu Glu Ser His Gly Ser Ser His Thr Pro Gln Asn Leu Ile Thr Val
            355                 360                 365

Lys Met Glu Gln Ala Phe Ala Arg Tyr Leu Leu Glu Gln Thr Pro Glu
     370                 375                 380

Gln Gln Ala Ala Ile Leu Ser Leu Val Gly Pro Glu Leu Glu Ser Val
385                 390                 395                400

Leu Glu Ser Thr Leu Glu Pro Val Ile Glu Pro Thr Leu Cys Met Val
     405                 410                 415
```

```
Ser Gln Thr Val Pro Glu Pro Asp Gln Gly Pro Val Ser Gln Pro Val
            420                 425                 430

Pro Glu Pro Asp Leu Pro Cys Asp Leu Arg His Leu Asn Thr Glu Pro
        435                 440                 445

Met Glu Ile Phe Arg Asn Cys Val Lys Ile Glu Ile Met Pro Asn
    450                 455                 460

Gly Asp Pro Leu Leu Ala Gly Gln Asn Thr Val Asp Glu Val Tyr Val
465                 470                 475                 480

Ser Arg Pro Ser His Phe Tyr Thr Asp Gly Pro Leu Met Pro Ser Asp
                485                 490                 495

Phe

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence:
      Illustrative ISRE promotor element
<220> FEATURE:
<221> NAME/KEY: modified_base
<222> LOCATION: (6)..(8)
<223> OTHER INFORMATION: a, t, c, g, unknown or other

<400> SEQUENCE: 3 agtttnnnttt tcc                                                         13

<210> SEQ ID NO 4
<211> LENGTH: 1179
<212> TYPE: DNA
<213> ORGANISM: Homo sapiens

<400> SEQUENCE: 4
atggcatcag gcagggcacg ctgcacccga aaactccgga actgggtggt ggagcaagtg       60
gagagtgggc agtttcccgg agtgtgctgg gatgatacag ctaagaccat gttccggatt      120
ccctggaaac atgcaggcaa gcaggacttc cgggaggacc aggatgctgc cttcttcaag      180
gcctgggcaa tatttaaggg aaagtataag gaggggggaca caggaggtcc agctgtctgg      240
aagactcgcc tgcgctgtgc actcaacaag agttctgaat ttaaggaggt tcctgagagg      300
ggccgcatgg atgttgctga gccctacaag gtgtatcagt tgctgccacc aggaatcgtc      360
tctggccagc cagggactca gaaagtacca tcaaagcgac agcacagttc tgtgtcctct      420
gagaggaagg aggaagagga tgccatgcag aactgcacac tcagtccctc tgtgctccag      480
gactccctca ataatgagga ggaggggggcc agtgggggag cagtccattc agacattggg      540
agcagcagca gcagcagcag ccctgagcca caggaagtta cagacacaac tgaggccccc      600
tttcaagggg atcagaggtc cctggagttt ctgcttcctc cagagccaga ctactcactg      660
ctgctcacct tcatctacaa cgggcgcgtg gtgggcgagg cccaggtgca aagcctggat      720
tgccgccttg tggctgagcc ctcaggctct gagagcagca tggagcaggt gctgttcccc      780
aagcctggcc cactggagcc cacgcagcgc ctgctgagcc agcttgagag ggcatccta      840 gtggccagca accccgagg cctcttcgtg cagcgccttt gccccatccc catctcctgg      900
aatgcacccc aggctccacc tgggccaggc ccgcatctgc tgcccagcaa cgagtgcgtg      960
gagctcttca gaaccgccta cttctgcaga gacttggtca ggtactttca gggcctgggc     1020 ccccccaccga agttccaggt aacactgaat ttctgggaag agagccatgg ctccagccat     1080
```

-continued

```
actccacaga atcttatcac agtgaagatg gagcaggcct ttgcccgata cttgctggag    1140
cagactccag agcagcaggc agccattctg tccctggtg                           1179
```

<210> SEQ ID NO 5
<211> LENGTH: 393
<212> TYPE: PRT
<213> ORGANISM: Homo sapiens

<400> SEQUENCE: 5

| Met | Ala | Ser | Gly | Arg | Ala | Arg | Cys | Thr | Arg | Lys | Leu | Arg | Asn | Trp | Val |
|---|---|---|---|---|---|---|---|---|---|---|---|---|---|---|---|
| 1 | | | | 5 | | | | | 10 | | | | | 15 | |

| Val | Glu | Gln | Val | Glu | Ser | Gly | Gln | Phe | Pro | Gly | Val | Cys | Trp | Asp | Asp |
|---|---|---|---|---|---|---|---|---|---|---|---|---|---|---|---|
| | | | 20 | | | | | 25 | | | | | 30 | | |

| Thr | Ala | Lys | Thr | Met | Phe | Arg | Ile | Pro | Trp | Lys | His | Ala | Gly | Lys | Gln |
|---|---|---|---|---|---|---|---|---|---|---|---|---|---|---|---|
| | | 35 | | | | | 40 | | | | | 45 | | | |

| Asp | Phe | Arg | Glu | Asp | Gln | Asp | Ala | Ala | Phe | Phe | Lys | Ala | Trp | Ala | Ile |
|---|---|---|---|---|---|---|---|---|---|---|---|---|---|---|---|
| | 50 | | | | | 55 | | | | | 60 | | | | |

| Phe | Lys | Gly | Lys | Tyr | Lys | Glu | Gly | Asp | Thr | Gly | Gly | Pro | Ala | Val | Trp |
|---|---|---|---|---|---|---|---|---|---|---|---|---|---|---|---|
| 65 | | | | | 70 | | | | | 75 | | | | | 80 |

| Lys | Thr | Arg | Leu | Arg | Cys | Ala | Leu | Asn | Lys | Ser | Ser | Glu | Phe | Lys | Glu |
|---|---|---|---|---|---|---|---|---|---|---|---|---|---|---|---|
| | | | 85 | | | | | 90 | | | | | 95 | | |

| Val | Pro | Glu | Arg | Gly | Arg | Met | Asp | Val | Ala | Glu | Pro | Tyr | Lys | Val | Tyr |
|---|---|---|---|---|---|---|---|---|---|---|---|---|---|---|---|
| | | | 100 | | | | | 105 | | | | | 110 | | |

| Gln | Leu | Leu | Pro | Pro | Gly | Ile | Val | Ser | Gly | Gln | Pro | Gly | Thr | Gln | Lys |
|---|---|---|---|---|---|---|---|---|---|---|---|---|---|---|---|
| | | 115 | | | | | 120 | | | | | 125 | | | |

| Val | Pro | Ser | Lys | Arg | Gln | His | Ser | Ser | Val | Ser | Ser | Glu | Arg | Lys | Glu |
|---|---|---|---|---|---|---|---|---|---|---|---|---|---|---|---|
| | 130 | | | | | 135 | | | | | 140 | | | | |

| Glu | Glu | Asp | Ala | Met | Gln | Asn | Cys | Thr | Leu | Ser | Pro | Ser | Val | Leu | Gln |
|---|---|---|---|---|---|---|---|---|---|---|---|---|---|---|---|
| 145 | | | | | 150 | | | | | 155 | | | | | 160 |

| Asp | Ser | Leu | Asn | Asn | Glu | Glu | Glu | Gly | Ala | Ser | Gly | Gly | Ala | Val | His |
|---|---|---|---|---|---|---|---|---|---|---|---|---|---|---|---|
| | | | 165 | | | | | 170 | | | | | 175 | | |

| Ser | Asp | Ile | Gly | Ser | Ser | Ser | Ser | Ser | Ser | Ser | Pro | Glu | Pro | Gln | Glu |
|---|---|---|---|---|---|---|---|---|---|---|---|---|---|---|---|
| | | | 180 | | | | | 185 | | | | | 190 | | |

| Val | Thr | Asp | Thr | Thr | Glu | Ala | Pro | Phe | Gln | Gly | Asp | Gln | Arg | Ser | Leu |
|---|---|---|---|---|---|---|---|---|---|---|---|---|---|---|---|
| | | 195 | | | | | 200 | | | | | 205 | | | |

| Glu | Phe | Leu | Leu | Pro | Pro | Glu | Pro | Asp | Tyr | Ser | Leu | Leu | Leu | Thr | Phe |
|---|---|---|---|---|---|---|---|---|---|---|---|---|---|---|---|
| | 210 | | | | | 215 | | | | | 220 | | | | |

| Ile | Tyr | Asn | Gly | Arg | Val | Val | Gly | Glu | Ala | Gln | Val | Gln | Ser | Leu | Asp |
|---|---|---|---|---|---|---|---|---|---|---|---|---|---|---|---|
| 225 | | | | | 230 | | | | | 235 | | | | | 240 |

| Cys | Arg | Leu | Val | Ala | Glu | Pro | Ser | Gly | Ser | Glu | Ser | Ser | Met | Glu | Gln |
|---|---|---|---|---|---|---|---|---|---|---|---|---|---|---|---|
| | | | 245 | | | | | 250 | | | | | 255 | | |

| Val | Leu | Phe | Pro | Lys | Pro | Gly | Pro | Leu | Glu | Pro | Thr | Gln | Arg | Leu | Leu |
|---|---|---|---|---|---|---|---|---|---|---|---|---|---|---|---|
| | | | 260 | | | | | 265 | | | | | 270 | | |

| Ser | Gln | Leu | Glu | Arg | Gly | Ile | Leu | Val | Ala | Ser | Asn | Pro | Arg | Gly | Leu |
|---|---|---|---|---|---|---|---|---|---|---|---|---|---|---|---|
| | | 275 | | | | | 280 | | | | | 285 | | | |

| Phe | Val | Gln | Arg | Leu | Cys | Pro | Ile | Pro | Ile | Ser | Trp | Asn | Ala | Pro | Gln |
|---|---|---|---|---|---|---|---|---|---|---|---|---|---|---|---|
| | 290 | | | | | 295 | | | | | 300 | | | | |

| Ala | Pro | Pro | Gly | Pro | Gly | Pro | His | Leu | Leu | Pro | Ser | Asn | Glu | Cys | Val |
|---|---|---|---|---|---|---|---|---|---|---|---|---|---|---|---|
| 305 | | | | | 310 | | | | | 315 | | | | | 320 |

| Glu | Leu | Phe | Arg | Thr | Ala | Tyr | Phe | Cys | Arg | Asp | Leu | Val | Arg | Tyr | Phe |
|---|---|---|---|---|---|---|---|---|---|---|---|---|---|---|---|
| | | | 325 | | | | | 330 | | | | | 335 | | |

| Gln | Gly | Leu | Gly | Pro | Pro | Lys | Phe | Gln | Val | Thr | Leu | Asn | Phe | Trp | |
|---|---|---|---|---|---|---|---|---|---|---|---|---|---|---|---|
| | | | 340 | | | | | 345 | | | | | 350 | | |

```
Glu Glu Ser His Gly Ser Ser His Thr Pro Gln Asn Leu Ile Thr Val
            355                 360                 365

Lys Met Glu Gln Ala Phe Ala Arg Tyr Leu Leu Glu Gln Thr Pro Glu
        370                 375                 380

Gln Gln Ala Ala Ile Leu Ser Leu Val
385                 390

<210> SEQ ID NO 6
<211> LENGTH: 312
<212> TYPE: DNA
<213> ORGANISM: Homo sapiens

<400> SEQUENCE: 6
gggccagagc tagagtctgt gctggagtcc actctggagc ctgtgataga gcccacacta      60
tgcatggtat cacaaacagt gccagagcca gaccaaggac ctgtatcaca gccagtgcca     120
gagccagatt tgccctgtga tctgagacat ttgaacactg agccaatgga aatcttcaga     180
aactgtgtaa agattgaaga aatcatgccg aatggtgacc cactgttggc tggccagaac     240
accgtggatg aggtttacgt ctcccgcccc agccacttct acactgatgg acccttgatg     300
ccttctgact tc                                                         312

<210> SEQ ID NO 7
<211> LENGTH: 104
<212> TYPE: PRT
<213> ORGANISM: Homo sapiens

<400> SEQUENCE: 7

Gly Pro Glu Leu Glu Ser Val Leu Glu Ser Thr Leu Glu Pro Val Ile
 1               5                  10                  15

Glu Pro Thr Leu Cys Met Val Ser Gln Thr Val Pro Glu Pro Asp Gln
            20                  25                  30

Gly Pro Val Ser Gln Pro Val Pro Glu Pro Asp Leu Pro Cys Asp Leu
        35                  40                  45

Arg His Leu Asn Thr Glu Pro Met Glu Ile Phe Arg Asn Cys Val Lys
    50                  55                  60

Ile Glu Glu Ile Met Pro Asn Gly Asp Pro Leu Leu Ala Gly Gln Asn
65                  70                  75                  80

Thr Val Asp Glu Val Tyr Val Ser Arg Pro Ser His Phe Tyr Thr Asp
                85                  90                  95

Gly Pro Leu Met Pro Ser Asp Phe
            100

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 8
caacgaattc caggtgtc                                                    18

<210> SEQ ID NO 9
<211> LENGTH: 18
<212> TYPE: DNA
<213> ORGANISM: Artificial Sequence
```

```
<220> FEATURE:
<223> OTHER INFORMATION: Description of Artificial Sequence: Primer

<400> SEQUENCE: 9
cccttgttat tcctcacc                                                        18

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 10
aatgccattt cacctggaac ttg                                                  23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
gtgatagtag acccaggcat agt                                                  23

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
gtgaaggtcg gagtcaac                                                        18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 13
tggaatttgc catgggtg                                                        18

<210> SEQ ID NO 14
<211> LENGTH: 114
<212> TYPE: DNA
<213> ORGANISM: Homo sapiens

<400> SEQUENCE: 14
cacccttcta gacttcagac cacagacaac ctgctcccca tgtctcctga ggagtttgac          60
gaggtgtctc ggatagtggg ctctgtagaa ttcgacagta tgatgaacac agta               114

<210> SEQ ID NO 15
<211> LENGTH: 38
<212> TYPE: PRT
<213> ORGANISM: Homo sapiens
```

<400> SEQUENCE: 15

His Pro Ser Arg Leu Gln Thr Thr Asp Asn Leu Leu Pro Met Ser Pro
 1               5                  10                  15

Glu Glu Phe Asp Glu Val Ser Arg Ile Val Gly Ser Val Glu Phe Asp
             20                  25                  30

Ser Met Met Asn Thr Val
         35

<210> SEQ ID NO 16
<211> LENGTH: 2556
<212> TYPE: DNA
<213> ORGANISM: Homo sapiens

<400> SEQUENCE: 16

```
atggcgcagt gggaaatgct gcagaatctt gacagcccct ttcaggatca gctgcaccag     60
ctttactcgc acagcctcct gcctgtggac attcgacagt acttggctgt ctggattgaa    120
gaccagaact ggcaggaagc tgcacttggg agtgatgatt ccaaggctac catgctattc    180
ttccacttct tggatcagct gaactatgag tgtggccgtt gcagccagga cccagagtcc    240
ttgttgctgc agcacaattt gcggaaattc tgccgggaca ttcagccctt tcccaggat    300
cctacccagt tggctgagat gatctttaac ctccttctgg aagaaaaaag aatttttgatc    360
caggctcaga gggcccaatt ggaacaagga gagccagttc tcgaaacacc tgtggagagc    420
cagcaacatg agattgaatc ccggatcctg gatttaaggg ctatgatgga gaagctggta    480
aaatccatca gccaactgaa agaccagcag gatgtcttct gcttccgata taagatccag    540
gccaaaggga gacacccctc tctggacccc catcagacca agagcagaa gattctgcag    600
gaaactctca tgaactgga caaaaggaga aggaggtgc tggatgcctc caaagcactg    660
ctaggccgat taactaccct aatcgagcta ctgctgccaa agttggagga gtggaaggcc    720
cagcagcaaa aagcctgcat cagagctccc attgaccacg ggttgaaca gctggagaca    780
tggttcacag ctggagcaaa gctgttgttt cacctgaggc agctgctgaa ggagctgaag    840
ggactgagtt gcctggttag ctatcaggat gaccctctga ccaaaggggt ggacctacgc    900
aacgcccagg tcacagagtt gctacagcgt ctgctccaca gagcctttgt ggtagaaacc    960
cagccctgca tgccccaaac tccccatcga cccctcatcc tcaagactgg cagcaagttc   1020
accgtccgaa caaggctgct ggtgagactc caggaaggca atgagtcact gactgtggaa   1080
gtctccattg acaggaatcc tcctcaatta caaggcttcc ggaagttcaa cattctgact   1140
tcaaaccaga aactttgac ccccgagaag gggcagagtc agggtttgat tgggacttt    1200
ggttacctga ctctggtgga gcaacgttca ggtggttcag gaaagggcag caataagggg   1260
ccactaggtg tgacagagga actgcacatc atcagcttca cggtcaaata tacctaccag   1320
ggtctgaagc aggagctgaa aacggacacc ctccctgtgg tgattatttc caacatgaac   1380
cagctctcaa ttgcctgggc ttcagttctc tggttcaatt tgctcagccc aaaccttcag   1440
aaccagcagt tcttctccaa cccccccaag gcccctgga gcttgctggg ccctgctctc   1500
agttggcagt tctcctccta tgttggccga ggcctcaact cagaccagct gagcatgctg   1560
agaaacaagc tgttcgggca gaactgtagg actgaggatc cattattgtc ctgggctgac   1620
ttcactaagc gagagagccc tcctggcaag ttaccattct ggacatggct ggacaaaatt   1680
ctggagttgg tacatgacca cctgaaggat ctctggaatg atggacgcat catgggcttt   1740
gtgagtcgga gccaggagcg ccggctgctg aagaagacca tgtctggcac ctttctactg   1800
```

-continued

```
cgcttcagtg aatcgtcaga aggggggcatt acctgctcct gggtggagca ccaggatgat    1860
gacaaggtgc tcatctactc tgtgcaaccg tacacgaagg aggtgctgca gtcactcccg    1920
ctgactgaaa tcatccgcca ttaccagttg ctcactgagg agaatatacc tgaaaaccca    1980
ctgcgcttcc tctatccccg aatccccgg gatgaagctt ttgggtgcta ctaccaggag    2040
aaagttaatc tccaggaacg gaggaaatac ctgaaacaca ggctcattgt ggtctctaat    2100
agacaggtgg atgaactgca caaccgctg gagcttaagc cagagccaga gctggagtca    2160
ttagagctgg aactagggct ggtgccagag ccagagctca gcctggactt agagccactg    2220
ctgaaggcag ggctggatct ggggccagag ctagagtctg tgctggagtc cactctggag    2280
cctgtgatag agcccacact atgcatggta tcacaaacag tgccagagcc agaccaagga    2340
cctgtatcac agccagtgcc agagccagat ttgccctgtg atctgagaca tttgaacact    2400
gagccaatgg aaatcttcag aaactgtgta aagattgaag aaatcatgcc gaatggtgac    2460
ccactgttgg ctggccagaa caccgtggat gaggtttacg tctcccgccc cagccacttc    2520
tacactgatg gaccccttgat gccttctgac ttctag                              2556
```

<210> SEQ ID NO 17
<211> LENGTH: 851
<212> TYPE: PRT
<213> ORGANISM: Homo sapiens

<400> SEQUENCE: 17

```
Met Ala Gln Trp Glu Met Leu Gln Asn Leu Asp Ser Pro Phe Gln Asp
  1               5                  10                  15

Gln Leu His Gln Leu Tyr Ser His Ser Leu Leu Pro Val Asp Ile Arg
             20                  25                  30

Gln Tyr Leu Ala Val Trp Ile Glu Asp Gln Asn Trp Gln Glu Ala Ala
         35                  40                  45

Leu Gly Ser Asp Asp Ser Lys Ala Thr Met Leu Phe Phe His Phe Leu
     50                  55                  60

Asp Gln Leu Asn Tyr Glu Cys Gly Arg Cys Ser Gln Asp Pro Glu Ser
 65                  70                  75                  80

Leu Leu Leu Gln His Asn Leu Arg Lys Phe Cys Arg Asp Ile Gln Pro
                 85                  90                  95

Phe Ser Gln Asp Pro Thr Gln Leu Ala Glu Met Ile Phe Asn Leu Leu
            100                 105                 110

Leu Glu Glu Lys Arg Ile Leu Ile Gln Ala Gln Arg Ala Gln Leu Glu
        115                 120                 125

Gln Gly Glu Pro Val Leu Glu Thr Pro Val Glu Ser Gln Gln His Glu
    130                 135                 140

Ile Glu Ser Arg Ile Leu Asp Leu Arg Ala Met Met Glu Lys Leu Val
145                 150                 155                 160

Lys Ser Ile Ser Gln Leu Lys Asp Gln Gln Asp Val Phe Cys Phe Arg
                165                 170                 175

Tyr Lys Ile Gln Ala Lys Gly Lys Thr Pro Ser Leu Asp Pro His Gln
            180                 185                 190

Thr Lys Glu Gln Lys Ile Leu Gln Glu Thr Leu Asn Glu Leu Asp Lys
        195                 200                 205

Arg Arg Lys Glu Val Leu Asp Ala Ser Lys Ala Leu Leu Gly Arg Leu
    210                 215                 220

Thr Thr Leu Ile Glu Leu Leu Leu Pro Lys Leu Glu Glu Trp Lys Ala
225                 230                 235                 240
```

```
Gln Gln Gln Lys Ala Cys Ile Arg Ala Pro Ile Asp His Gly Leu Glu
                245                 250                 255

Gln Leu Glu Thr Trp Phe Thr Ala Gly Ala Lys Leu Leu Phe His Leu
            260                 265                 270

Arg Gln Leu Leu Lys Glu Leu Lys Gly Leu Ser Cys Leu Val Ser Tyr
        275                 280                 285

Gln Asp Asp Pro Leu Thr Lys Gly Val Asp Leu Arg Asn Ala Gln Val
290                 295                 300

Thr Glu Leu Leu Gln Arg Leu His Arg Ala Phe Val Val Glu Thr
305                 310                 315                 320

Gln Pro Cys Met Pro Gln Thr Pro His Arg Pro Leu Ile Leu Lys Thr
                325                 330                 335

Gly Ser Lys Phe Thr Val Arg Thr Arg Leu Leu Val Arg Leu Gln Glu
            340                 345                 350

Gly Asn Glu Ser Leu Thr Val Glu Val Ser Ile Asp Arg Asn Pro Pro
        355                 360                 365

Gln Leu Gln Gly Phe Arg Lys Phe Asn Ile Leu Thr Ser Asn Gln Lys
    370                 375                 380

Thr Leu Thr Pro Glu Lys Gly Gln Ser Gln Gly Leu Ile Trp Asp Phe
385                 390                 395                 400

Gly Tyr Leu Thr Leu Val Glu Gln Arg Ser Gly Gly Ser Gly Lys Gly
                405                 410                 415

Ser Asn Lys Gly Pro Leu Gly Val Thr Glu Glu Leu His Ile Ile Ser
            420                 425                 430

Phe Thr Val Lys Tyr Thr Tyr Gln Gly Leu Lys Gln Glu Leu Lys Thr
        435                 440                 445

Asp Thr Leu Pro Val Val Ile Ile Ser Asn Met Asn Gln Leu Ser Ile
450                 455                 460

Ala Trp Ala Ser Val Leu Trp Phe Asn Leu Leu Ser Pro Asn Leu Gln
465                 470                 475                 480

Asn Gln Gln Phe Phe Ser Asn Pro Pro Lys Ala Pro Trp Ser Leu Leu
                485                 490                 495

Gly Pro Ala Leu Ser Trp Gln Phe Ser Ser Tyr Val Gly Arg Gly Leu
            500                 505                 510

Asn Ser Asp Gln Leu Ser Met Leu Arg Asn Lys Leu Phe Gly Gln Asn
        515                 520                 525

Cys Arg Thr Glu Asp Pro Leu Leu Ser Trp Ala Asp Phe Thr Lys Arg
    530                 535                 540

Glu Ser Pro Pro Gly Lys Leu Pro Phe Trp Thr Trp Leu Asp Lys Ile
545                 550                 555                 560

Leu Glu Leu Val His Asp His Leu Lys Asp Leu Trp Asn Asp Gly Arg
                565                 570                 575

Ile Met Gly Phe Val Ser Arg Ser Gln Glu Arg Arg Leu Leu Lys Lys
            580                 585                 590

Thr Met Ser Gly Thr Phe Leu Leu Arg Phe Ser Glu Ser Ser Glu Gly
        595                 600                 605

Gly Ile Thr Cys Ser Trp Val Glu His Gln Asp Asp Asp Lys Val Leu
    610                 615                 620

Ile Tyr Ser Val Gln Pro Tyr Thr Lys Glu Val Leu Gln Ser Leu Pro
625                 630                 635                 640

Leu Thr Glu Ile Ile Arg His Tyr Gln Leu Leu Thr Glu Glu Asn Ile
                645                 650                 655
```

```
Pro Glu Asn Pro Leu Arg Phe Leu Tyr Pro Arg Ile Pro Arg Asp Glu
            660                 665                 670
Ala Phe Gly Cys Tyr Tyr Gln Glu Lys Val Asn Leu Gln Glu Arg Arg
        675                 680                 685
Lys Tyr Leu Lys His Arg Leu Ile Val Val Ser Asn Arg Gln Val Asp
    690                 695                 700
Glu Leu Gln Gln Pro Leu Glu Leu Lys Pro Glu Pro Glu Leu Glu Ser
705                 710                 715                 720
Leu Glu Leu Glu Leu Gly Leu Val Pro Glu Pro Glu Leu Ser Leu Asp
                725                 730                 735
Leu Glu Pro Leu Leu Lys Ala Gly Leu Asp Leu Gly Pro Glu Leu Glu
            740                 745                 750
Ser Val Leu Glu Ser Thr Leu Glu Pro Val Ile Glu Pro Thr Leu Cys
        755                 760                 765
Met Val Ser Gln Thr Val Pro Glu Pro Asp Gln Gly Pro Val Ser Gln
    770                 775                 780
Pro Val Pro Glu Pro Asp Leu Pro Cys Asp Leu Arg His Leu Asn Thr
785                 790                 795                 800
Glu Pro Met Glu Ile Phe Arg Asn Cys Val Lys Ile Glu Glu Ile Met
                805                 810                 815
Pro Asn Gly Asp Pro Leu Leu Ala Gly Gln Asn Thr Val Asp Glu Val
            820                 825                 830
Tyr Val Ser Arg Pro Ser His Phe Tyr Thr Asp Gly Pro Leu Met Pro
        835                 840                 845
Ser Asp Phe
    850

<210> SEQ ID NO 18
<211> LENGTH: 2253
<212> TYPE: DNA
<213> ORGANISM: Homo sapiens

<400> SEQUENCE: 18
atgtctcagt ggtacgaact tcagcagctt gactcaaaat tcctggagca ggttcaccag      60
ctttatgatg acagttttcc catggaaatc agacagtacc tggcacagtg gttagaaaag     120
caagactggg agcacgctgc caatgatgtt tcatttgcca ccatccgttt tcatgacctc     180
ctgtcacagc tggatgatca atatagtcgc ttttctttgg agaataactt cttgctacag     240
cataacataa ggaaaagcaa gcgtaatctt caggataatt ttcaggaaga cccaatccag     300
atgtctatga tcatttacag ctgtctgaag gaagaaagga aaattctgga aaacgcccag     360
agatttaatc aggctcagtc ggggaatatt cagagcacag tgatgttaga caaacagaaa     420
gagcttgaca gtaaagtcag aaatgtgaag acaaggtta tgtgtataga gcatgaaatc     480
aagagcctgg aagatttaca agatgaatat gacttcaaat gcaaaaccttg cagaacagaa     540 gaacacgaga ccaatggtgt ggcaaagagt gatcagaaac aagaacagct gttactcaag     600
aagatgtatt taatgcttga caataagaga aggaagtag ttcacaaaat aatagagttg     660
ctgaatgtca ctgaacttac ccagaatgcc ctgattaatg atgaactagt ggagtggaag     720
cggagacagc agagcgcctg tattgggggg ccgcccaatg cttgcttgga tcagctgcag     780
aactggttca ctatagttgc ggagagtctg cagcaagttc ggcagcagct taaaaagttg     840
gaggaattgg aacagaaata cacctacgaa catgacccta tcacaaaaaa caaacaagtg     900
ttatgggacc gcaccttcag tcttttccag cagctcattc agagctcgtt tgtggtggaa     960
```

```
agacagccct gcatgccaac gcaccctcag aggccgctgg tcttgaagac agggtccag    1020 ttcactgtga agttgagact gttggtgaaa ttgcaagagc tgaattataa tttgaaagtc    1080
aaagtcttat ttgataaaga tgtgaatgag agaaatacag taaaaggatt taggaagttc    1140
aacattttgg gcacgcacac aaaagtgatg aacatggagg agtccaccaa tggcagtctg    1200
gcggctgaat tcggcacct gcaattgaaa gaacagaaaa atgctggcac cagaacgaat    1260
gagggtcctc tcatcgttac tgaagagctt cactccctta gttttgaaac ccaattgtgc    1320
cagcctggtt tggtaattga cctcgagacg acctctctgc ccgttgtggt gatctccaac    1380
gtcagccagc tcccgagcgg ttgggcctcc atcctttggt acaacatgct ggtggcggaa    1440
cccaggaatc tgtccttctt cctgactcca ccatgtgcac gatgggctca gctttcagaa    1500
gtgctgagtt ggcagttttc ttctgtcacc aaaagaggtc tcaatgtgga ccagctgaac    1560
atgttgggag agaagcttct tggtcctaac gccagccccg atggtctcat ccgtggacg    1620 aggttttgta aggaaaatat aaatgataaa aattttccct tctggctttg gattgaaagc    1680
atcctagaac tcattaaaaa acacctgctc cctctctgga atgatgggtg catcatgggc    1740
ttcatcagca aggagcgaga gcgtgccctg ttgaaggacc agcagccggg gaccttcctg    1800
ctgcggttca gtgagagctc ccgggaaggg gccatcacat tcacatgggt ggagcggtcc    1860
cagaacggag cgaacctga cttccatgcg gttgaaccct acacgaagaa agaactttct    1920
gctgttactt tccctgacat cattcgcaat tacaaagtca tggctgctga aatattcct    1980 gagaatcccc tgaagtatct gtatccaaat attgacaaag accatgcctt tggaaagtat    2040
tactccaggc caaaggaagc accagagcca atggaacttg atggccctaa ggaactgga    2100 tatatcaaga ctgagttgat ttctgtgtct gaagttcacc cttctagact tcagaccaca    2160
gacaacctgc tccccatgtc tcctgaggag tttgacgagg tgtctcggat agtgggctct    2220
gtagaattcg acagtatgat gaacacagta tag                                2253
```

<210> SEQ ID NO 19
<211> LENGTH: 750
<212> TYPE: PRT
<213> ORGANISM: Homo sapiens

<400> SEQUENCE: 19

```
Met Ser Gln Trp Tyr Glu Leu Gln Gln Leu Asp Ser Lys Phe Leu Glu
 1               5                  10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140
```

-continued

```
Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
            165                 170                 175

Leu Gln Asn Arg Glu His Glu Thr Asn Gly Val Ala Lys Ser Asp Gln
        180                 185                 190

Lys Gln Glu Gln Leu Leu Lys Lys Met Tyr Leu Met Leu Asp Asn
    195                 200                 205

Lys Arg Lys Glu Val Val His Lys Ile Ile Glu Leu Leu Asn Val Thr
210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
    290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
    370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
        435                 440                 445

Glu Thr Thr Ser Leu Pro Val Val Val Ile Ser Asn Val Ser Gln Leu
    450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
        515                 520                 525

Pro Asn Ala Ser Pro Asp Gly Leu Ile Pro Trp Thr Arg Phe Cys Lys
    530                 535                 540

Glu Asn Ile Asn Asp Lys Asn Phe Pro Phe Trp Leu Trp Ile Glu Ser
545                 550                 555                 560
```

```
Ile Leu Glu Leu Ile Lys Lys His Leu Leu Pro Leu Trp Asn Asp Gly
            565                 570                 575
Cys Ile Met Gly Phe Ile Ser Lys Glu Arg Glu Arg Ala Leu Leu Lys
        580                 585                 590
Asp Gln Gln Pro Gly Thr Phe Leu Leu Arg Phe Ser Glu Ser Ser Arg
    595                 600                 605
Glu Gly Ala Ile Thr Phe Thr Trp Val Glu Arg Ser Gln Asn Gly Gly
610                 615                 620
Glu Pro Asp Phe His Ala Val Glu Pro Tyr Thr Lys Lys Glu Leu Ser
625                 630                 635                 640
Ala Val Thr Phe Pro Asp Ile Ile Arg Asn Tyr Lys Val Met Ala Ala
                645                 650                 655
Glu Asn Ile Pro Glu Asn Pro Leu Lys Tyr Leu Tyr Pro Asn Ile Asp
            660                 665                 670
Lys Asp His Ala Phe Gly Lys Tyr Tyr Ser Arg Pro Lys Glu Ala Pro
        675                 680                 685
Glu Pro Met Glu Leu Asp Gly Pro Lys Gly Thr Gly Tyr Ile Lys Thr
    690                 695                 700
Glu Leu Ile Ser Val Ser Glu Val His Pro Ser Arg Leu Gln Thr Thr
705                 710                 715                 720
Asp Asn Leu Leu Pro Met Ser Pro Glu Glu Phe Asp Glu Val Ser Arg
                725                 730                 735
Ile Val Gly Ser Val Glu Phe Asp Ser Met Met Asn Thr Val
            740                 745                 750

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 20
cccggatccc cgccatggca tcaggcaggg cacgc                                35

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 21
ggggcggccg cctagaagtc agaaggcatc                                      30

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 22
gccattctgt ccctggtggg gccagagcta gagtct                               36

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Primer
```

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 24
ggggcggccg cctacccacc gtactcgtc                                    29

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 25
gccattctgt ccctggtgtc gacggccccc cca                               33

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 26
tggggggggc cgtcgacacc agggacagaa tggc                              34

<210> SEQ ID NO 27
<211> LENGTH: 240
<212> TYPE: DNA
<213> ORGANISM: Artificial Sequence
<220> FEATURE:
<223> OTHER INFORMATION: Description of Artificial Sequence: Synthetic
      HSV VP16 TAD nucleotide sequence

<400> SEQUENCE: 27
tcgacggccc cccccaccga tgtcagcctg ggggacgagc tccacttaga cggcgaggac    60
gtggcgatgg cgcatgccga cgcgctagac gatttcgatc tggacatgtt ggggacggg    120 gattccccgg gtccgggatt taccccccac gactccgccc cctacggcgc tctggatatg   180
gccgacttcg actttgagca gatgtttacc gatgcccttg gaattgacga gtacggtggg   240

<210> SEQ ID NO 28
<211> LENGTH: 80
<212> TYPE: PRT
<213> ORGANISM: Artificial Sequence
<220> FEATURE:
<223> OTHER INFORMATION: Description of Artificial Sequence: Synthetic
      HSV VP16 TAD peptide sequence

<400> SEQUENCE: 28

Ser Thr Ala Pro Pro Thr Asp Val Ser Leu Gly Asp Glu Leu His Leu
  1               5                  10                  15

Asp Gly Arg Asp Tyr Ala Met Ala His Ala Asp Ala Leu Asp Asp Phe
             20                  25                  30

-continued

```
Asp Leu Asp Met Leu Gly Asp Gly Asp Ser Pro Gly Pro Gly Phe Thr
         35                  40                  45
Pro His Asp Ser Ala Pro Tyr Gly Ala Leu Asp Met Ala Asp Phe Glu
     50                  55                  60
Phe Glu Gly His Phe Thr Asp Ala Leu Gly Ile Asp Glu Tyr Gly Gly
 65                  70                  75                  80
```

<210> SEQ ID NO 29
<211> LENGTH: 1419
<212> TYPE: DNA
<213> ORGANISM: Artificial Sequence
<220> FEATURE:
<223> OTHER INFORMATION: Description of Artificial Sequence: Synthetic
      p48-VP16 nucleotide sequence

<400> SEQUENCE: 29

| | | |
|---|---|---|
| atggcatcag gcagggcacg ctgcacccga aaactccgga actgggtggt ggagcaagtg | 60 |
| gagagtgggc agtttcccgg agtgtgctgg gatgatacag ctaagaccat gttccggatt | 120 |
| ccctggaaac atgcaggcaa gcaggacttc cgggaggacc aggatgctgc cttcttcaag | 180 |
| gcctgggcaa tatttaaggg aaagtataag gaggggggaca caggaggtcc agctgtctgg | 240 |
| aagactcgcc tgcgctgtgc actcaacaag agttctgaat ttaaggaggt tcctgagagg | 300 |
| ggccgcatgg atgttgctga gcctacaag gtgtatcagt tgctgccacc aggaatcgtc | 360 |
| tctggccagc cagggactca gaaagtacca tcaaagcgac agcacagttc tgtgtcctct | 420 |
| gagaggaagg aggaagagga tgccatgcag aactgcacac tcagtccctc tgtgctccag | 480 |
| gactccctca taatgagga ggaggggcc agtgggggag cagtccattc agacattggg | 540 |
| agcagcagca gcagcagcag ccctgagcca caggaagtta cagacacaac tgaggccccc | 600 |
| tttcaagggg atcagaggtc cctggagttt ctgcttcctc cagagccaga ctactcactg | 660 |
| ctgctcacct tcatctacaa cgggcgcgtg gtgggcgagg cccaggtgca aagcctggat | 720 |
| tgccgccttg tggctgagcc ctcaggctct gagagcagca tggagcaggt gctgttcccc | 780 |
| aagcctggcc cactggagcc cacgcagcgc ctgctgagcc agcttgagag gggcatccta | 840 |
| gtggccagca cccccgagg cctcttcgtg cagcgccttt gccccatccc catctcctgg | 900 |
| aatgcacccc aggctccacc tgggccaggc ccgcatctgc tgcccagcaa cgagtgcgtg | 960 |
| gagctcttca gaaccgccta cttctgcaga gacttggtca ggtactttca gggcctgggc | 1020 |
| cccccaccga gttccaggt aacactgaat ttctgggaag agagccatgg ctccagccat | 1080 |
| actccacaga tcttatcac agtgaagatg gagcaggcct ttgcccgata cttgctggag | 1140 |
| cagactccag agcagcaggc agccattctg tccctggtgt cgacggcccc ccccaccgat | 1200 |
| gtcagcctgg ggacgagct ccacttagac ggcgaggacg tggcgatggc catgccgac | 1260 |
| gcgctagacg atttcgatct ggacatgttg gggacgggg attccccggg tccgggattt | 1320 |
| accccccacg actccgcccc ctacggcgct ctggatatgg ccgacttcga ctttgagcag | 1380 |
| atgtttaccg atgcccttgg aattgacgag tacggtggg | 1419 |

<210> SEQ ID NO 30
<211> LENGTH: 473
<212> TYPE: PRT
<213> ORGANISM: Artificial Sequence
<220> FEATURE:
<223> OTHER INFORMATION: Description of Artificial Sequence: Synthetic
      p48-VP16 protein sequence

<400> SEQUENCE: 30

```
Met Ala Ser Gly Arg Ala Arg Cys Thr Arg Lys Leu Arg Asn Trp Val
  1               5                  10                  15

Val Glu Gln Val Glu Ser Gly Gln Phe Pro Gly Val Cys Trp Asp Asp
             20                  25                  30

Thr Ala Lys Thr Met Phe Arg Ile Pro Trp Lys His Ala Gly Lys Gln
         35                  40                  45

Asp Phe Arg Glu Asp Gln Asp Ala Ala Phe Phe Lys Ala Trp Ala Ile
     50                  55                  60

Phe Lys Gly Lys Tyr Lys Glu Gly Asp Thr Gly Pro Ala Val Trp
 65                  70                  75                  80

Lys Thr Arg Leu Arg Cys Ala Leu Asn Lys Ser Ser Glu Phe Lys Glu
                 85                  90                  95

Val Pro Glu Arg Gly Arg Met Asp Val Ala Glu Pro Tyr Lys Val Tyr
            100                 105                 110

Gln Leu Leu Pro Pro Gly Ile Val Ser Gly Pro Gly Thr Gln Lys
            115                 120                 125

Val Pro Ser Lys Arg Gln His Ser Ser Val Ser Ser Glu Arg Lys Glu
130                 135                 140

Glu Glu Asp Ala Met Gln Asn Cys Thr Leu Ser Pro Ser Val Leu Gln
145                 150                 155                 160

Asp Ser Leu Asn Asn Glu Glu Glu Gly Ala Ser Gly Gly Ala Val His
                165                 170                 175

Ser Asp Ile Gly Ser Ser Ser Ser Ser Ser Pro Glu Pro Gln Glu
            180                 185                 190

Val Thr Asp Thr Thr Glu Ala Pro Phe Gln Gly Asp Gln Arg Ser Leu
            195                 200                 205

Glu Phe Leu Leu Pro Pro Glu Pro Asp Tyr Ser Leu Leu Leu Thr Phe
            210                 215                 220

Ile Tyr Asn Gly Arg Val Val Gly Glu Ala Gln Val Gln Ser Leu Asp
225                 230                 235                 240

Cys Arg Leu Val Ala Glu Pro Ser Gly Ser Glu Ser Ser Met Glu Gln
                245                 250                 255

Val Leu Phe Pro Lys Pro Gly Pro Leu Glu Pro Thr Gln Arg Leu Leu
            260                 265                 270

Ser Gln Leu Glu Arg Gly Ile Leu Val Ala Ser Asn Pro Arg Gly Leu
            275                 280                 285

Phe Val Gln Arg Leu Cys Pro Ile Pro Ile Ser Trp Asn Ala Pro Gln
            290                 295                 300

Ala Pro Pro Gly Pro Gly Pro His Leu Leu Pro Ser Asn Glu Cys Val
305                 310                 315                 320

Glu Leu Phe Arg Thr Ala Tyr Phe Cys Arg Asp Leu Val Arg Tyr Phe
                325                 330                 335

Gln Gly Leu Gly Pro Pro Lys Phe Gln Val Thr Leu Asn Phe Trp
            340                 345                 350

Glu Glu Ser His Gly Ser Ser His Thr Pro Gln Asn Leu Ile Thr Val
            355                 360                 365

Lys Met Glu Gln Ala Phe Ala Arg Tyr Leu Leu Glu Gln Thr Pro Glu
    370                 375                 380

Gln Gln Ala Ala Ile Leu Ser Leu Val Ser Thr Ala Pro Pro Thr Asp
385                 390                 395                 400

Val Ser Leu Gly Asp Glu Leu His Leu Asp Gly Arg Asp Tyr Ala Met
                405                 410                 415
```

```
-continued

Ala His Ala Asp Ala Leu Asp Asp Phe Asp Leu Asp Met Leu Gly Asp
            420                 425                 430

Gly Asp Ser Pro Gly Pro Gly Phe Thr Pro His Asp Ser Ala Pro Tyr
        435                 440                 445

Gly Ala Leu Asp Met Ala Asp Phe Glu Phe Glu Gly His Phe Thr Asp
    450                 455                 460

Ala Leu Gly Ile Asp Glu Tyr Gly Gly
465                 470
```

HYBRID FUSION PROTEIN TRANSCRIPTION REGULATOR TO INDUCE INTERFERON TARGET GENE EXPRESSION

This application is a national phase application under 35 U.S.C. § 371 of international application number PCT/US02/31768, filed on Oct. 3, 2002, entitled "A Hybrid Fusion Protein Transcription Regulator to Induce Interferon Target Gene Expression," which claims priority to U.S. provisional application No. 60/352,777, filed on Jan. 29, 2002 and U.S. provisional application No. 60/327,746, filed on Oct. 5, 2001, all of which are hereby incorporated in their entirety.

FIELD OF THE INVENTION

The present invention relates to isolated fusion proteins which induce innate anti-viral immune responses and regulate viral proliferation in the absence of interferon treatment. These fusion proteins can be used for the treatment and therapy of tumors, cancers, and viral infections.

BACKGROUND OF THE INVENTION

Interferons (IFNS) are cytokine proteins that are produced by cells infected with viruses and that induce potent anti-viral activities via the immediate induction of gene expression following binding to cell surface receptors. Thus, interferons are not direct anti-viral agents, but induce one or several anti-viral mechanisms. In addition, interferons act on viruses other than the specific virus inducing the interferon.

The principal innate anti-viral mechanism for most cells involves the actions of Type I interferons (IFN$\alpha$ and IFN$\beta$), leading to the induction of interferon responsive gene expression. Two families of transcriptional regulators, i.e., members of the "signal transducers and activators of transcription" (STAT) and "interferon regulatory factor" (IRF) families, work in conjunction to establish a cascade of gene regulation and signal transduction events that lead to transcriptional activation of interferon-stimulated genes (ISGs). Proteins encoded by such ISGs have potent anti-viral properties, which include disruption of the viral replicative life cycle, blockage of cell cycle progression, and apoptosis.

A trimeric complex, IFN Stimulated Gene Factor 3 (ISGF3), is formed following IFN binding to cell surface receptors and is comprised of (i) STAT1, (ii) STAT2, and (iii) p48/ISGF3$\gamma$/IRF9 (FIG. 3). The STAT family members are proteins of 100 kDa molecular weight containing highly conserved SH2 domains, SH3-like domains, and unique regions which serve as sites of interaction with other proteins involved in signal transduction. The STATs also contain general characteristics of transcription factors including a conserved DNA binding domain, a COOH-terminal transcriptional activation domain, and regions to contact other transcriptional regulators. The p48/ISGF3$\gamma$/IRF9 protein, herein referred to as p48, is not a STAT factor, but is a member of the IRF (Interferon Regulatory Factor) family. In addition, the p48 protein is an essential component of ISGF3 that contributes DNA binding specificity and provides specific protein binding sites for the recruitment of STAT1 and STAT2 proteins to the promoter, but is otherwise transcriptionally inert.

Genes that are transcriptionally activated by IFNs share a common promoter element called the IFN stimulated gene response element (ISRE); (AGTTTN$_3$TTTCC, SEQ ID NO: 3). The trimeric protein complex, ISGF3, binds with high affinity to the ISRE following IFN treatment (Fu et al., 1990, *Proc. Natl. Acad. Sci. USA*, 87: 8555-8559; Fu et al., 1992, *Proc. Natl. Acad. Sci. USA*, 89: 7840-7843; Schindler et al., 1992, *Proc. Natl. Acad. Sci. USA*, 89: 7836-7839).

The general mechanism for activation of transcription by ISGF3 can be viewed as a two-phase process: As depicted in FIG. 4, the first phase (signaling phase) involves receptor-mediated signal transduction to generate a nuclear transcription complex; the second phase (transcription phase) involves the initiation of activation of target genes by the complex. The first phase has been well characterized. Binding of IFN to its receptor activates the tyrosine kinases JAK1 and TYK2 to phosphorylate the IFN receptor cytoplasmic domain, providing a docking site for STAT2. STAT2 phosphorylation provides a docking site for STAT1. Following STAT1 phosphorylation, the two STATs heterodimerize to form STAT1:2 heterodimer. Thereafter, the STAT1:2 heterodimer associates with p48 to form the trimeric ISGF3 complex. This trimeric complex represents an elaborate scheme to target the STAT2 C-terminus, which contains the essential transcriptional activation domain of ISGF3, to the appropriate promoters for participation in transcriptional activation.

Most transcription activating proteins contain a sequence-specific DNA binding domain linked to a transcriptional activation domain. Therefore, this modular nature of transcription factors is the basis of "two hybrid systems" for screening libraries for protein interaction partners. Indeed, it has been well documented that many protein regions can act as transcriptional activation domains (TADs) when fused to DNA binding domains, regardless of their original cellular function (see, e.g., Brent and Ptashne, 1985, *Cell*: 43: 729-36; Ma and Ptashne, 1987, *Cell* 51: 113-9; Ma and Ptashne, 1988, *Cell* 55: 443-6). While such TADs differ in the ability to mediate precise protein:protein contacts with transcriptional machinery, the TADs function similarly as activators of RNA polymerase.

IFNs are the principle innate anti-viral and anti-tumor cytokines and are also potent immuno-modulators that participate in the regulation of the functions of T-cells, B-cells, natural killer cells, and macrophages. Moreover, IFNs possess direct anti-proliferative activities and are cytostatic or cytotoxic for a number of different tumor and cancer cell types. Therefore, IFNs are involved in both anti-viral and anti-neoplastic (e.g., cancer and tumor) responses.

IFN genes were first cloned in 1979 and have been approved since 1991 for the treatment of hepatitis C infection. IFNs have been associated with the treatment of cancer and infectious diseases because of their roles in both the innate and adaptive immune systems. Specifically, IFNs have been employed for therapeutic use against hairy-cell leukemia, chronic hepatitis B, a major cause of liver cancer and cirrhosis, as well as for treatment of genital warts and some rarer cancers of the blood and bone marrow. Nasal sprays containing alpha interferon also provide some protection against colds caused by rhinoviruses.

However, as the IFN system represents an early and crucial step in anti-viral immunity, it is not surprising to find that many viruses have evolved strategies to block the actions of IFN. The ability of a virus to antagonize the IFN pathway can have dramatic consequences for the success of infection. The virulence of a specific virus strain can be determined largely by susceptibility to the anti-viral effects of IFN. Furthermore, the mutations which enhance IFN resistance can lead to highly infectious and persistent infections. The ability of a wide variety of viruses to fight the IFN system is illustrated by the diverse strategies used to overcome the effects of IFN (Bergmann et al., 2000, *Journal of Virology;* 74(13): 6203-6206 and Kitajewski et al., 1986, *Cell;* 45(2): 195-200). The viral proteins block a variety of steps in the IFN signaling system, in many cases at an early point upstream of gene activation.

Accordingly, there exists a need to activate interferon stimulated gene expression directly by bypassing the normal interferon induced pathway for the transcription of ISGs. Consequently, the virus families which have evolved strategies to block the actions of IFN will not have the ability to hinder the IFN pathway, since the interferon stimulated genes will be activated directly even in the absence of IFN binding to its receptor. In addition, cancer cells and tumor cells which have developed mechanisms to evade IFN action may also benefit by the direct activation of interferon stimulated genes. The present invention satisfies such a need by providing fusion protein transcription regulators which provide effective gene therapy strategies for virus infections as a result of activating transcription of interferon stimulated genes directly, thus bypassing the need of IFN for ISG-gene expression.

SUMMARY OF THE INVENTION

It is an aspect of the present invention to provide chimeric polynucleotide molecules encoding novel hybrid fusion polypeptide transcription regulators to induce interferon target gene expression for use in anti-viral, anti-tumor, and/or anti-cancer applications. More specifically, the present invention provides hybrid fusion (or chimeric) proteins comprising a component which is an IRF, e.g., a DNA binding domain, and a component which is a transcriptional activation domain (TAD). Preferably, the TAD is a STAT transcriptional activation domain. However, the TAD can also be a transcriptional activation domain isolated from a protein possessing a TAD, such as a viral protein, e.g., VP16 of Herpes Simplex Virus (HSV).

A particular example of a chimeric fusion protein of the invention is p48-S2C, wherein p48 is all or a functional portion of the p48 protein and S2C is a STAT2 TAD. The nucleic acid sequence and amino acid sequence (SEQ ID NOS: 1 and 2, respectively) of the p48-S2C fusion protein are provided. In the absence of IFN, the p48-S2C chimeric protein produces Type I interferon (IFNα/β) induced activities, yielding constitutive ISG expression, as well as anti-viral and growth regulatory effects.

An additional example of a chimeric fusion protein of the invention is p48-VP16 TAD, wherein p48 is all or a functional portion of the p48 protein and VP16 TAD is the transcriptional activation domain of the VP16 protein of HSV, preferably comprising amino acids 411-490 of VP16. The nucleic acid sequence and amino acid sequence (SEQ ID NOS: 29 and 30, respectively) of the p48-VP6 TAD fusion protein are provided.

The present invention provides purified and isolated nucleic acid molecules encoding the p48-S2C and the p48-VP16 TAD protein products according to the present invention. The polynucleotide sequences of the p48-S2C fusion product and the p48-VP16 TAD fusion product are set forth in SEQ ID NO: 1 and SEQ ID NO: 29, respectively.

It is a further aspect of the present invention to provide novel p48-TAD fusion polynucleotide molecules, associated vectors, host cells, and methods of use. Preferably, the fusion polynucleotide molecules are DNA molecules.

It is yet a further aspect of the present invention to provide vectors, preferably expression vectors, comprising a nucleic acid sequence coding for a hybrid p48-TAD fusion polypeptide. A particular example is the p48 IRF protein fused to a STAT TAD. A further, but non-limiting, example is the p48 IRF protein fused to the TAD of HSV VP16. Functional or biologically active fragments of p48-TAD are also encompassed by the present invention. Host cells containing p48-TAD encoding vectors and isolated polypeptides comprising the amino acid sequence of the p48-TAD protein are provided. Such polypeptides may be isolated and purified employing conventional methodologies, following expression in the host cell. In the case of STAT TADs, the vector preferably contains a full-length p48-STAT TAD polynucleotide sequence encoding a full-length p48-STAT TAD polypeptide. Also provided by the invention are functional portions of p48 and TAD molecules comprising the chimeric transcription regulator described herein. In a more preferred embodiment, the vector contains a full length p48-S2C polynucleotide sequence encoding a full-length p48-S2C polypeptide.

A further aspect of the present invention is to provide methods of inducing anti-viral and anti-neoplastic cell immune responses by using a p48-TAD fusion protein. In addition, the present invention encompasses a method of treating chronic viral infections including viral infections associated with IFN-resistant viruses. Accordingly, the present invention provides a therapeutic for treating an individual in need of treatment for a condition that is susceptible to the activity of ISG products. Such conditions include virus infection and tumors, or cancers, in view of the anti-proliferative effects of IFN.

This invention further provides a method of activating cellular interferon stimulated genes which encode proteins that have potent anti-viral properties. The method comprises contacting cells with the hybrid fusion polypeptide p48-TAD, preferably p48 fused to a STAT2 TAD, or a functional portion thereof, in an amount effective to activate transcription of the interferon stimulated genes and/or to effect an anti-viral, anti-cancer, or anti-tumor response.

Additional aspects and advantages afforded by the present invention will be apparent from the detailed description hereinbelow.

DESCRIPTION OF THE FIGURES

The appended drawings of the figures are presented to further describe the invention and to assist in its appreciation and understanding through clarification of its various aspects.

FIG. 1 illustrates the nucleic acid sequence (i.e., cDNA) encoding the hybrid fusion protein p48-S2C (SEQ ID NO: 1). In FIG. 1, the nucleotides presented in bold font represent the nucleic acid sequence encoding the STAT2 TAD.

FIG. 2 illustrates the amino acid sequence (SEQ ID NO: 2) of the hybrid fusion protein p48-S2C, as encoded by SEQ ID NO: 1. In FIG. 2, the amino acids presented in bold font represent the amino acid sequence of the STAT2 TAD.

FIG. 6 illustrates the nucleic acid sequence (SEQ ID NO: 4) encoding the p48 interferon regulatory factor.

FIG. 7 illustrates the amino acid sequence (SEQ ID NO: 5) of the p48 interferon regulatory factor, encoded by SEQ ID NO: 4.

FIG. 8 illustrates the nucleic acid sequence (SEQ ID NO: 6) encoding STAT2 TAD (S2C).

FIG. 9 illustrates the amino acid sequence (SEQ ID NO: 7) of STAT2 TAD (S2C), encoded by SEQ ID NO: 6.

FIG. 10 illustrates a partial list of viral gene products used to bypass the IFN system, and the target protein in the IFN signaling system. The viral proteins produced block a variety of steps in the IFN signaling system, in many cases at an early point upstream of gene activation.

FIG. 11 illustrates various non-limiting applications of the p48-TAD fusion protein transcription regulator according to this invention.

FIG. 12 illustrates the nucleic acid sequence (SEQ ID NO: 14) encoding STAT1 TAD (S1C).

FIG. 13 illustrates the amino acid sequence (SEQ ID NO: 15) of STAT1 TAD (S1C), encoded by SEQ ID NO: 14.

FIGS. 14A and 14B illustrate the expression and activity of p48-S2C fusion protein.

FIGS. 15A, 15B and 15C illustrate the expression and activity of the p48-S2C fusion protein in STAT-deficient cell lines.

FIG. 16 illustrates the activity of p48-S2C in endogenous interferon stimulated gene (ISG) regulation.

FIGS. 19A, 19B and 19C illustrate Tet-inducible expression of p48, p48-S1C, and p48-S2C in several stable cell lines.

FIGS. 22A and 22B illustrate the transcriptional activities of p48-S2C and the TAD variants. FIG. 22B depicts the relative activity of the p48-S2C TAD mutant variants compared to p48-S2C.

FIG. 24 illustrates the nucleic acid sequence (SEQ ID NO: 16) encoding STAT2.

FIG. 25 illustrates the amino acid sequence (SEQ ID NO: 17) of STAT2, encoded by SEQ ID NO: 16.

FIG. 26 illustrates the nucleic acid sequence (SEQ ID NO: 18) encoding STAT1.

FIG. 27 illustrates the amino acid sequence (SEQ ID NO: 19) of STAT1, encoded by SEQ ID NO: 18.

FIG. 28 illustrates the nucleic acid sequence (SEQ ID NO: 27) encoding the transcriptional activation domain of HSV VP16.

FIG. 29 illustrates the amino acid sequence (SEQ ID NO: 28) of the transcriptional activation domain of HSV VP16 as encoded by SEQ ID NO: 27.

FIG. 30 illustrates the nucleic acid sequence (i.e., cDNA) encoding the hybrid fusion protein p48-VP16 TAD (SEQ ID NO: 29). In FIG. 30, the nucleotides presented in bold font represent the HSV VP16 TAD.

FIG. 31 illustrates the amino acid sequence (SEQ ID NO: 30) of the hybrid fusion protein p48-VP16 TAD as encoded by SEQ ID NO: 29. In FIG. 31, the amino acids presented in bold font represent the amino acid sequence of the HSV VP16 TAD.

FIG. 32A compares the transcriptional activities of p48-S2C and p48-VP16 TAD and FIG. 32B illustrates the activity of p48-VP16 TAD in endogenous interferon stimulated gene (ISG) regulation.

FIG. 33 tabulates the anti-viral effects of p48-S2C expression for both IFN-sensitive and IFN-resistant viruses, which include vesicular stomatitis virus (VSV), simian virus 5 (SV5), type II human parainfluenza virus (HPIV2), and herpes simplex virus (HSV-1).

DETAILED DESCRIPTION OF THE INVENTION

Figure 3:
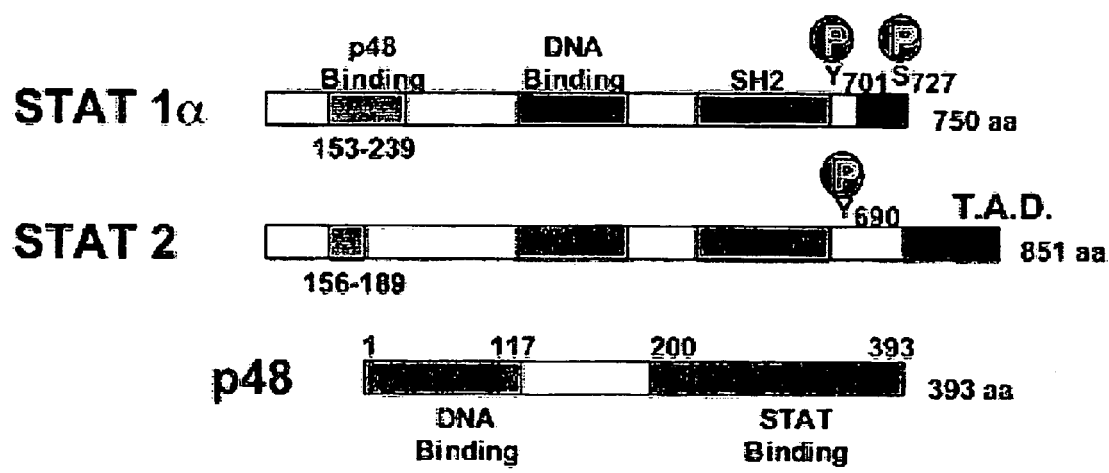
FIG. 3 illustrates the three proteins that form the ISGF3 transcription factor complex; STAT1, STAT2 and p48.
Figure 4:
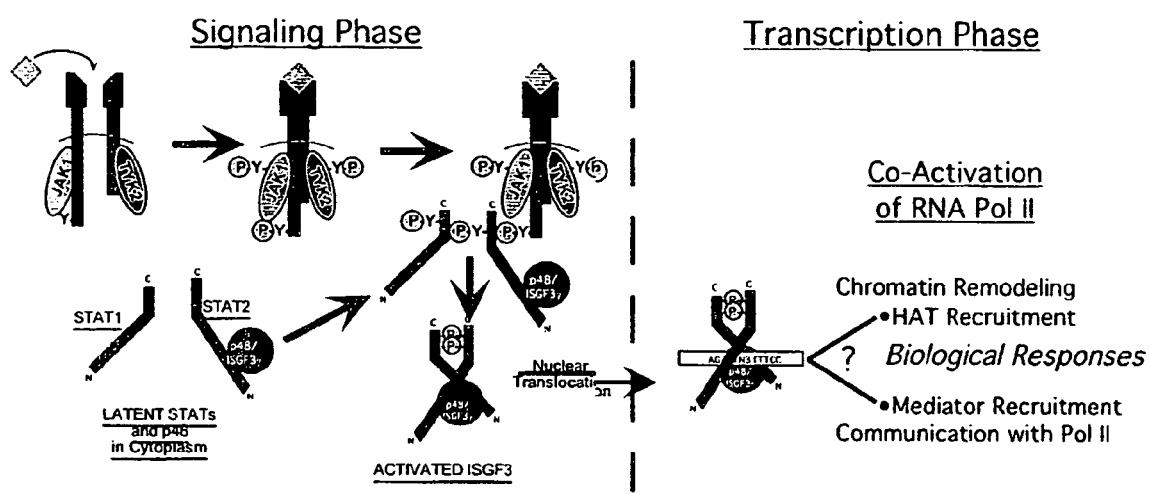
FIG. 4 illustrates the general mechanism for activation of interferon induced transcription by ISGF3 as a two-phase process.

The present invention is directed to novel transcription regulators, which induce interferon target gene expression and provide beneficial uses in anti-viral, anti-cancer, and anti-tumor applications. The transcription regulators which comprise a fusion protein, include a DNA binding domain and a transcriptional activation domain (TAD). According to the present invention, the TAD in the novel transcription regulator causes p48 to activate transcription of interferon stimulated genes thus recapitulating IFN biological responses in the absence of IFN stimulation.

In one embodiment of the present invention, the DNA binding domain of the transcription regulators comprises the p48 protein, or a functional portion thereof. Preferably, the p48 protein component comprises 90-175 amino acids, and more preferably comprises 150 amino acids, of the DNA binding domain of p48.

In another embodiment of the invention, the TAD is obtained from a STAT protein and thus the chimeric proteins comprise p48, or a functional portion thereof, fused to a STAT TAD. In a more preferred embodiment the TAD is from STAT2, and the p48 and STAT2 TAD-containing containing fusion protein is termed p48-S2C.

In another embodiment of this invention, the TAD can be obtained from proteins other than STAT. TAD proteins are typically modular in nature, including those that regulate transcription. Most transcription activating proteins consist of a sequence-specific DNA binding domain linked to a transcriptional activation domain. As discussed herein, many protein regions can act as TADs when fused to DNA binding domains, regardless of their original cellular function (see, e.g., Brent and Ptashne, 1985, *Cell* 43: 729-36; Ma and Ptashne, 1987, *Cell* 51: 113-9; Ma and Ptashne, 1988, *Cell* 55: 443-6.). While such TADs differ in the ability to mediate precise protein:protein contacts with transcriptional machinery, they function similarly as activators of RNA polymerase.

Accordingly, any transcriptional activating portion of any protein or any random peptide sequence may function in activating an inert p48 or the p48 DNA binding domain alone. The various TADs will very likely differ in intensity, and thus could be useful for fine tuning the degree of responsiveness. As a particular, but not limiting example, the transcriptional activation domain from the VP16 protein of HSV is known to be potent and serves as a model of a "generic" TAD. Preferably, the TAD of the HSV VP16 protein comprises amino acids 411-490 of the VP16 protein. The Genbank Accession Number for the VP16 protein of Herpes Simplex Virus (HSV) is M15621 (Pellett et al., 1985, *PNAS*, 82 (17): 5870-74).

The HSV VP16 TAD fused to p48, referred to herein as p48-VP16 TAD, has been shown to be a effective transcriptional activator (FIG. 32). Therefore, despite the qualitative differences in the way the STAT TAD and the VP16 TAD function, they are both able to activate p48 so as to allow it to be an ISG activator. Further, and by way of example, the yeast protein GAL4 also provides a transcriptional activation domain that can be fused to the p48 protein in order to activate transcription of interferon stimulated genes.

When expressed in mammalian cells, the p48-TAD fusion protein accumulates in the nucleus and is believed to bind to target gene promoters via its p48 DNA binding domain. The presence of the transcriptional activation domain in the p48-TAD product, particularly the p48-S2C or p48-VP16 TAD product, allows the protein to recruit RNA polymerase and associated factors, thereby initiating target gene transcription. The p48 protein component comprises a DNA recognition subunit for the native IFN responsive complex. Therefore, the hybrid proteins induce the expression of genes normally responsive to IFN signals. A particular advantage of the IFN transcription regulators according to the present invention is that they can induce anti-viral, anti-tumor, or anti-cancer effects and control cell proliferation in the absence of IFN and through a mechanism which is independent of IFN receptor binding.

Abbreviations

The following abbreviatons used herin are defined as follows:

| | |
|---|---|
| HSV VPI6 | VP16 protein of the Herpes Simplex Virus |
| IFN | Interferon |
| IRF | IFN regulatory factor |
| ISG | IFN-stimulated gene |
| ISGF | IFN-stimulated gene factor |
| ISRE | IFN-stimulated gene response element |
| ORF | open reading frame |
| p48 | IRF protein; DNA sequence recognition subunit of the ISGF3 complex |
| p48-S1C | hybrid protein comprising p48 fused to STAT1 TAD |
| p48-S2C | hybrid protein comprising p48 fused to STAT2 TAD |
| p48-VP16 TAD | hybrid protein comprising p48 fused to HSV VP16 TAD |
| STAT | signal transducer and activator of transcription |
| S1C | STAT1 transcriptional activation domain (C-terminal 38 amino acids) |
| S2C | STAT2 transcriptional activation domain (C-terminal 104 amino acids) |
| TAD | transcriptional activation domain |

Definitions

Unless otherwise defined, the technical and scientific terms as used herein have the same meanings as are commonly understood by persons skilled in the art to which the present invention pertains. The following definitions apply to the terms used throughout this specification, unless otherwise defined in specific instances:

Signaling molecule refers to an extracellular polypeptide, peptide, oligosaccharide or other non-peptidyl molecule, in either a free or bound form, that interacts with a receptor at or near the surface of a cell. This interaction in turn triggers an intracellular pathway which includes the activation of one or more transcriptional regulatory proteins that bind to a regulatory element, thereby transcriptionally modulating the expression of an associated gene or genes. As used herein, signaling molecule includes naturally occurring molecules, such as cytokines, peptidyl and non-peptidyl hormones, antibodies, cell-surface antigens, or synthetic mimics of any of these signaling molecules, or synthetic molecules that mimic the action of any of these signaling molecules.

Cytokines refer to a diverse grouping of soluble polypeptides, including growth factors and hormones, that control the growth, differentiation and function of cells in such a manner as to ultimately elicit a phenotypic response in an organism.

Transcriptional regulatory proteins refer to cytoplasmic or nuclear proteins that, when activated, bind the regulatory elements/oligonucleotide sequences either directly, or indirectly through a complex of transcriptional regulatory proteins or other adapter proteins, to transcriptionally modulate the activity of an associated gene or genes.

To transcriptionally modulate the expression of an associated gene or genes means to affect the transcription, e.g., change the rate of transcription, activate transcription or inhibit transcription of a gene or genes.

STAT protein refers to those transcriptional regulatory proteins designated as "Signal Transducers and Activators of Transcription."

A vector or construct refers to any genetic element, including, but not limited to, plasmids, vectors, chromosomes and viruses, that incorporates the nucleic acid sequences of the present invention. The construct can be a DNA construct or an RNA construct. As a nonlimiting example, a DNA construct can be a vector comprising a promoter that is operably linked to an oligonucleotide sequence of the present invention, which is in turn operably linked to a heterologous gene, such as the gene for the luciferase reporter molecule.

Promoter is a regulatory element and refers to a nucleic acid regulatory region capable of binding directly or indirectly to RNA polymerase in a cell and initiating transcription of a downstream (3' direction) coding sequence.

A host cell that has been "transfected" or "transformed" by exogenous or heterologous DNA (e.g. a DNA construct) contains such DNA following introduction into the cell. The transfecting DNA may or may not be integrated into the chromosomal DNA of the cell. In prokaryotes, yeast, and mammalian cells, for example, the transfecting DNA can be maintained on an episomal element such as a plasmid. With respect to eukaryotic cells, a stably transfected or transformed cell comprises transfected DNA inherited by daughter cells. This stability is demonstrated by the ability of the eukaryotic cell to establish cell lines or clones comprised of a population of daughter cells containing the transfected DNA.

Host cell refers to a cell or cell line that expresses the fusion protein of the present invention after transfection of the requisite DNA.

Purified refers to molecules, either polynucleotides or amino acids (polypeptides and proteins) that are removed from their natural environment and substantially isolated or separated from at least one other component with which they are naturally associated. Polynucleotides include nucleic acids, namely, DNA, cDNA, genomic DNA, RNA, synthetic forms and mixed polymers, both sense and antisense strands, and may be chemically or biochemically modified, or may contain non-natural or derivatized nucleotide bases, as will be readily appreciated by those skilled in the art.

In general, a polypeptide refers to a polymer of amino acids and its equivalents, and does not refer to a specific length of the product. Peptides, oligopeptides and proteins can be termed polypeptides. The terms polypeptide and protein are often used interchangeably herein. The term polypeptide includes modifications of the polypeptide, e.g., glycosylation, acetylation, phosphorylation and the like. Also included in the definition of polypeptides, e.g., p48-TAD polypeptides, are, for example, polypeptides containing one or more analogs of an amino acid (including, for example, unnatural amino acids, and the like), polypeptides with substituted linkages, as well as other modifications known in the art, both naturally and non-naturally occurring.

Open reading frame, or "ORF", refers to a DNA sequence containing a series of nucleotide triplets coding for amino acids and typically lacking any termination codons.

Description of the Invention

The present invention encompasses novel hybrid, chimeric, or fusion proteins, termed p48-TAD proteins, produced either synthetically or recombinantly. p48-TAD proteins are transcription regulators, which, in the absence of IFN treatment, can induce the expression of genes normally regulated by IFN.

Figure 5:
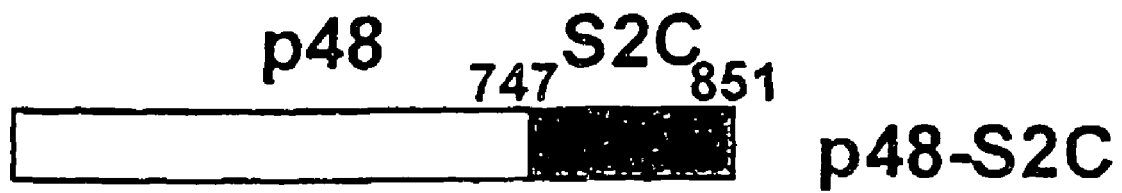
FIG. 5 illustrates the p48-S2C transcription regulator according to the present invention.

In one embodiment of the present invention, the novel transcription regulators comprise functionally important regions of two of the three protein subunits, i.e., STAT1, STAT2 and p48, that form the ISGF3 transcription factor complex. For example, the present invention provides the p48 protein genetically fused to the transcriptional activation domain (TAD) of the STAT2 protein (FIG. 5). A further embodiment comprises the p48 protein fused to the transcriptional activation domain (TAD) of any protein that can activate p48 as an IFN mimetic transcription factor, for example, the TAD of HSV VP16. The fusion proteins as described herein comprise all or a functional portion of p48 fused to all of a functional portion of a protein TAD.

More particularly, DNA clones comprising full-length p48-S2C cDNA and p48-VP16 TAD cDNA (in pcDNA3.1) of the present invention have been deposited with the American Type Culture Collection (ATCC) (10801 University Blvd., Manassas, Va. 20110-2209) on Nov. 28, 2001, ATCC Accession Numbers PTA-3886 and PTA-3887, respectively. The deposit(s) referred to herein will be maintained under the terms of the Budapest Treaty on the International Recognition of the Deposit of Microorganisms for purposes of Patent Procedure. These deposits are provided merely as convenience to those of skill in the art and are not an admission that a deposit is required under 35 U.S.C. 112. The sequence of the polynucleotides contained in the deposited materials, as well as the amino acid sequence of the of the polypeptides encoded thereby, are incorporated herein by reference and are controlling in the event of any conflict with any description of sequences herein. A license may be required to make, use or sell the deposited materials, and no such license is hereby granted.

p48, a 48 kDa protein, is a member of the interferon regulatory factor (IRF) family. The p48 protein serves as the DNA sequence recognition subunit of the ISGF3 complex and is required for IFN responses. Also, the COOH terminus of p48 mediates ISGF3 formation (Horvath et al., 1996, *Mol. Cell. Biol.*, 16: 6957-6964) by binding directly to the STAT1 and STAT2 subunits. In addition, p48 contains a bipartite nuclear retention signal within its amino-terminal DNA-binding domain (see, Lau et al., 2000, *PNAS*, 97:13, 7278-83). FIGS. 6 and 7 illustrate the nucleic acid sequence (SEQ ID NO: 4) and the amino acid sequence (SEQ ID NO: 5), respectively, of p48.

STAT2 is a member of the signal transducer and activator of transcription family (STAT). The STAT family members are proteins of 100 kDa molecular weight containing highly conserved SH2 domains, SH3-like domains, and unique regions which serve as sites of interaction with other proteins involved in signal transduction. The STATs also contain general characteristics of transcription factors, including a conserved DNA binding domain, a carboxy (COOH)-terminal transcriptional activation domain, and regions to contact other transcriptional regulators. For anti-viral effects, the transcriptional activation domain is preferably, although not limited to, STAT2. FIGS. 24 and 25 illustrate the nucleic acid sequence (SEQ ID NO: 16) and the amino acid sequence (SEQ ID NO: 17) of STAT2, respectively.

In one embodiment of the present invention, the fusion proteins comprise the p48 binding IRF protein fused to the transcriptional activating domain of any protein or peptide sequence that functions to activate inert p48 or the p48 DNA binding domain alone, thus resulting in the ability of p48 to serve as an activator of IFN-stimulated gene expression in the absence of interferon treatment.

Figure 21:
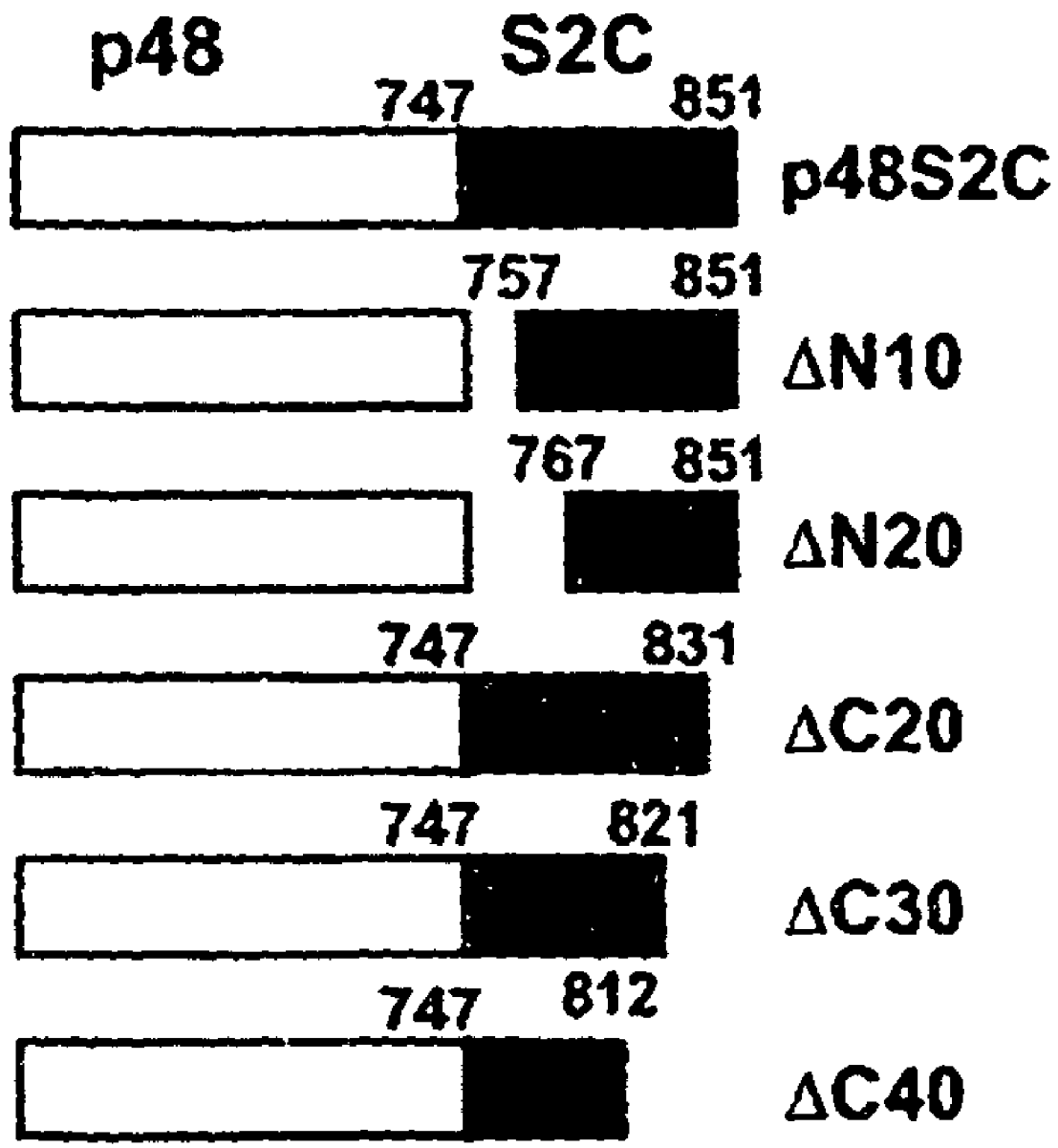
FIG. 21 depicts variants of the STAT2 transcriptional activation domain (TAD). Additional p48-S2C hybrids were constructed which comprise N- or C-terminal deletions within the 104 amino acids comprising STAT2 TAD.

In a further embodiment of the present invention, the fusion proteins comprise the p48 binding IRF protein fused either chemically, synthetically, or recombinantly to the transcription activation domain of STAT2. Preferably, the C-terminal 104 amino acids of STAT2 are employed. FIGS. 8 and 9 illustrate the nucleic acid sequence (SEQ ID NO: 6) and the amino acid sequence (SEQ ID NO: 7) of the STAT2 TAD (S2C). In yet another embodiment, functional fragments or portions of the p48 protein are fused to functional fragments or portions of the STAT transcriptional activation domain. The fragments of p48 preferably comprise 90-175 amino acids, more preferably 150 amino acids of the p48 DNA binding domain. The fragments or portions of STAT TAD, preferably STAT2 TAD, comprise amino (N)- or carboxy (C)-terminal deletions within the 104 amino acids of the STAT TAD, such that the N-terminal or the C-terminal deletions of the STAT TAD result in the retention of transcriptional activity. Accordingly, the STAT transcriptional activation domain can be subdivided into various sub-domains which can transcriptionally modulate the expression of the associated interferon stimulated genes. For example, suitable STAT2 portions can include, without limitation, amino acids 747-851, 757-851, 767-851, 747-831, 747-821 or 747-812, such as shown in FIG. 21.

In yet a further embodiment of the present invention, the chimeric proteins comprise the p48 binding protein, or any functional portion thereof, fused to the transcriptional activation domain of a protein having a TAD. In a more preferred and related embodiment, the protein is the VP16 protein of HSV. Preferably, the C-terminal amino acids, 411-490, of VP16 TAD are employed. FIGS. 28 and 29 illustrate the nucleic acid sequence (SEQ ID NO: 27) and the amino acid sequence (SEQ ID NO: 28) of the transcriptional activation domain (TAD) of the HSV VP16 protein. In a further embodiment, functional fragments of the p48 protein are fused to functional fragments or portions of the VP16 transcriptional activation domain.

In another of its embodiments, this invention encompasses novel hybrid or chimeric proteins that serve as transcription regulators and induce the expression of genes normally regulated by Type I interferon (IFN) in the absence of IFN treatment. Expression of such ISGs indicates that when expressed in mammalian cells, the chimeric p48-TAD proteins of the invention accumulate in the nucleus and bind to target gene promoters via the p48 DNA binding domain, thus resulting in transcription of the ISGs.

The presence of the transcriptional activation domain (TAD), e.g., STAT2 TAD or VP16 TAD, in the chimeric p48-TAD proteins allows the proteins to recruit RNA polymerase and associated factors, thereby initiating target gene expression. The p48 protein component serves as the DNA recognition subunit for the native IFN response complex and therefore, the hybrid factor induces the expression of genes normally responsive to IFN signals. The result of this gene activation is the production of proteins that create an anti-viral (or an anti-tumor or anti-cancer) state in the cells, independent of IFN or IFN receptor binding. Such anti-viral properties include disruption of the viral replicative life cycle, blockage of cell cycle progression and apoptosis. Anti-tumor properties can include sensitivity to drug or chemo-therapeutic agents. Thus, the use of the p48-TAD novel chimeric IFN transcription regulator provides an effective agent for treating or preventing virus infections because of its ability to bypass virus induced antagonism to host anti-viral mechanisms, thus magnifying anti-viral immunity.

In another embodiment of the present invention, the p48-TAD hybrid proteins serve as direct activators of interferon stimulated genes (ISGs) to provide effective gene therapy strategies for treating and/or preventing virus infection or in treating and/or preventing neoplasms, e.g., tumors or cancers. As particular examples, the p48-S2C and p48-VP16 TAD hybrid proteins can bypass the block to normal IFN-dependent regulation, which is caused by viruses that have evolved to evade the IFN response, and thus hyperactivate ISG expression directly. The virulence of a specific virus strain can be determined largely by susceptibility to the anti-viral effects of IFN, and mutations which enhance IFN resistance can lead to highly infectious and persistent infections. FIG. 10 illustrates representative examples of viral gene products used to bypass target proteins in the IFN system that are affected. The viral proteins block a variety of steps in the IFN signaling system, in many cases at an early point upstream of gene activation, thereby antagonizing both IFN responses and IFN production. For example, negative-strand RNA viruses of the family Paramyxoviridae have evolved specific proteins that directly suppress IFN signaling by lowering the concentration of cellular STAT proteins.

In accordance with the present invention, the novel p48-TAD transcription regulators provide anti-viral and therapeutic agents. Because the IFN response is effective against a broad range of virus types, p48-TAD can be utilized in the treatment of infection caused by a multitude of virus strains. Because the p48-TAD hybrid proteins are capable of activating endogenous interferon-stimulated genes (ISG) in the absence of IFN treatment, these chimeric proteins, used alone or in combination, are useful in the treatment of infection caused by a broad range of virus types, including, but not limited to, Hepatitis C, HIV, EBV, Herpes, Varicella, Kaposi's Sarcoma, Influenza Virus, Rhinovirus, Respiratory Syncytial Virus, Parainfluenza, West Nile Virus, Nipah, Hendra, Ebola, Rift Valley Fever, Hemorrhagic Fevers, Encephalitis Virus, Foot-and-Mouth Disease Virus, and Flock house virus relevant to the meat and poultry Industry. Examples of suitable applications of the p48-TAD chimeric proteins, preferably the p48-STAT TAD chimeric protein of the present invention include, but are not limited to, those described in FIG. 11.

Also in accordance with this invention, the novel p48-TAD transcription regulators can be used in the treatment and/or therapy of cancers, tumors, or neoplastic diseases. Indeed, it has been reported that that IRF9 (p48) is expressed in paclitaxel (taxol)-resistant breast tumors and may play a role in linking downstream mediators of IFN signaling to drug resistance in human cancers (see, Luker et al., 2001, *Cancer Research;* 61: 6540-6547). Thus, p48 alone in its normal state may control the resistant phenotype. In this regard, an active p48 as provided by the novel transcription regulators of the present invention can be used to revert drug resistant tumors, e.g. taxol-resistant breast tumor cells, to drug sensitivity.

One advantage of the fusion proteins of the present invention is their ability to directly activate interferon stimulated genes in target cells in the absence of IFN treatment. As illustrated in FIG. 11 and discussed in further detail herein, the novel hybrid protein p48-TAD can be used as a prophylactic or therapeutic anti-viral agent, or as an anti-tumor or anti-cancer agent. It can be administered to an individual in need of treatment either as a polypeptide-containing pharmaceutical composition, or as a polynucleotide in a pharmaceutical composition, by means of gene therapy in both in vivo and ex vivo applications. Such compositions contain a physiologically-acceptable carrier, diluent or excipient. Combinations of p48-TADs are envisioned for therapeutic and/or prophylactic uses according to the present invention.

In a particular embodiment of the present invention, the p48-S2C nucleic acid sequence is provided (SEQ ID NO: 1), (FIG. 1). For therapy involving p48-S2C, p48-S2C-encoding nucleic acid is preferably introduced into vectors and/or formulated as described hereinbelow and as known and practiced in the art. In addition, the p48-VP16 TAD nucleic acid sequence is provided (SEQ ID NO: 29), (FIG. 30). For therapy involving p48-VP16 TAD, p48-VP16 TAD encoding nucleic acid is preferably introduced into vectors and/or formulated as described hereinbelow and as known and practiced in the art.

Another particular embodiment of the present invention encompasses a polypeptide comprising the p48-S2C amino acid sequence provided herein (SEQ ID NO: 2), (FIG. 2). A further embodiment encompasses a polypeptide comprising the p48-VP16 TAD amino acid sequence provided herein (SEQ ID NO: 30), (FIG. 31). In addition, p48-S2C and p48-VP16 TAD polypeptides and polynucleotides can be used to prepare vectors, cells and/or cell lines using procedures routinely practiced in the art. All of these materials are useful in therapeutic anti-viral, anti-cancer, and anti-tumor applications.

While the foregoing and following detailed description often relates to a preferred embodiment of the present invention, i.e., the hybrid protein p48-S2C, it will be understood by the skilled practitioner in the art that a chimeric protein comprising p48, or a functional portion thereof, fused to a p48-activating TAD of a protein, or a functional portion thereof, can be employed without departing from the spirit or scope of the invention. For instance, transcriptional activating domains of any protein or peptide sequence, e.g., the TAD of VP16, can function in activating inert p48, or a functional portion thereof, to induce ISG expression.

Production of p48-S2C/p48-VP16 TAD Nucleic Acid

The p48-S2C and p48-VP16 TAD polynucleotide sequences are set forth in SEQ ID NO: 1 and SEQ ID NO: 29, respectively.

The nucleic acid encoding the p48-S2C or the p48-VP16 TAD protein can be modified to prepare useful mutations and/or variant proteins. For example, the polynucleotide sequence can be modified to provide additional restriction endonuclease recognition sites in the nucleic acid. Such mutations may be silent or may change the amino acid encoded by the mutated codon. Moreover, modified nucleic acids can be prepared, for example, by mutating the nucleic acid coding for p48-S2C or p48-VP16 TAD to result in deletion, substitution, insertion, inversion, or addition of one or more amino acids in the encoded polypeptide. For methods of site-directed mutagenesis, see Taylor, J. W. et al., 1985, *Nucl. Acids Res.,* 13, 8749-64 and Kunkel, J. A., 1985, *Proc. Natl. Acad. Sci. U.S.A.* 82: 482-92. In addition, kits for site-directed mutagenesis are available from commercial vendors (e.g., BioRad Laboratories, Richmond, Calif.; Amersham Corp., Arlington Heights, Ill.). For disruption, deletion and truncation methods, see Sayers, J. R. et al., 1988, *Nucl. Acids Res.,* 16: 791-800.

Expression Vectors

The present invention further encompasses expression vectors which comprise all or a functional portion of the polynucleotide sequences encoding p48-TAD fusion polypeptides as described herein, or functional peptides thereof. Preferably, the expression vectors comprise all or a portion of the nucleic acid sequence as shown in SEQ ID NO: 1 or SEQ ID NO: 29.

Expression vectors are usually plasmids, but the invention includes other vector forms, such as viral vectors, including recombinant viral vectors known and used by those skilled in the art, as well as vectors that serve equivalent functions and become known in the art subsequently hereto. The polynucleotide sequences encoding p48-TAD proteins can be stably integrated into the chromosome of an appropriate host cell using direct DNA introduction methods as practiced in the art. Suitable expression vectors include, but are not limited to, mammalian cell expression vectors, such as pcDNA3 (available from Invitrogen), bacterial cell expression vectors, such as pET-30 (available from Novagen or Promega) or yeast expression vectors. Preferred are mammalian cell expression vectors.

Expression vectors typically contain regulatory elements capable of affecting expression of the p48-TAD protein, e.g., p48-S2C or p48-VP16 TAD protein. These regulatory elements can be heterologous to native p48, or native S2C or VP16 TAD elements. Typically, a vector contains an origin of replication, a promoter, and a transcription termination sequence. The vector may also include other regulatory sequences, including mRNA stability sequences, which provide for stability of the expression product; secretory leader sequences, which provide for secretion of the expression product; environmental feedback sequences, which allow expression of the structural gene to be modulated (e.g., by the presence or absence of nutrients or other inducers in the growth medium); marking sequences, which are capable of providing phenotypic selection in transformed host cells; restriction sites, which provide sites for cleavage by restriction endonucleases; and sequences which allow expression in various types of host cells, including prokaryotic cells, yeast, fungi, algae, plant cells, insect cells, mammalian cells, including human cells and non-human animal cells, cells of non-human primates, and cells of higher eukaryotes.

As will be appreciated by the skilled practitioner, expression vectors comprise a nucleic acid sequence encoding at least one p48-TAD polypeptide, such as the p48-S2C or p48-VP16 TAD polypeptide described herein, operably linked to at least one regulatory sequence or element. Operably linked is intended to mean that the nucleotide acid sequence is linked to a regulatory sequence in a manner which allows expression of the nucleotide sequence. Regulatory sequences are known in the art and are selected to direct expression of the desired protein in an appropriate host cell. Accordingly, the term regulatory sequence includes promoters, enhancers and other expression control elements (see, D. V. Goeddel, 1990, *Methods Enzymol.*, 185:3-7). It will be appreciated by the skilled practitioner that the design of the expression vector can depend on such factors as the choice of the host cell to be transfected and/or the type of protein to be expressed.

Vectors can contain one or more replication and inheritance systems for cloning or expression, one or more markers for selection in the host, e.g. antibiotic resistance, and/or one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Host Cells

Host cells containing an expression vector that comprises a nucleic acid sequence encoding the p48-TAD fusion proteins of the present invention can be cultured under conditions suitable for the expression and recovery of the expressed protein, e.g., from cell membranes or cell lysates, using methods known and practiced by those in the art. In particular, the host cells can contain an expression vector which comprises all or a portion of the DNA sequence having the nucleotide sequence substantially as shown in SEQ ID NO:1, i.e. the p48-S2C coding region. The host cells can also contain an expression vector which comprises all or a portion of the DNA sequence having the nucleotide sequence substantially as shown in SEQ ID NO: 29, i.e. the p48-VP16 TAD coding region.

Suitable host cells include both prokaryotic cells (e.g., without limitation, *E. coli* strains HB101, DH5a, XL1 Blue, Y1090 and JM101), plant cells, fungal cells, and eukaryotic cells. Eukaryotic recombinant host cells are preferred. Examples of eukaryotic host cells include, but are not limited to, yeast, e.g., *S. cerevisiae* cells, cell lines of human, bovine, porcine, monkey, and rodent origin, as well as insect cells, including but not limited to, *Spodoptera frugiperda* insect cells and *Drosophila*-derived insect cells. Mammalian species-derived cell lines suitable for use and commercially available include, but are not limited to, L cells, CV-1 cells, CHO cells, (CHO-K1, ATCC CCL 61), COS-1 cells (ATCC CRL 1650), COS-7 cells (ATCC CRL 1651), HEK 293 cells, human skin fibroblasts, 3T3 cells (ATCC CCL 92), HeLa cells (ATCC CCL 2), C127I (ATCC CRL 1616), BS-C-1 (ATCC CCL 26) and MRC-5 (ATCC CCL 171).

The expression vectors can be introduced into host cells by various methods known in the art. Exemplary, yet nonlimiting, methods include transfection by calcium phosphate precipitation, electroporation, liposomal fusion/lipofection, transformation, transduction, protoplast fusion, direct DNA injection, nuclear injection, microparticle (e.g., colloidal gold) bombardment and viral or phage infection. The host cells are then cultured under conditions permitting expression of the p48-TAD fusion protein, preferably in large amounts. The cells containing expression vectors and expressing the p48-TAD proteins can be clonally propagated and individually analyzed to determine the level of novel p48-TAD, e.g., p48-S2C or p48-VP16 TAD, transcription regulator production; the p48-TAD proteins are isolated by conventional methods as discussed hereinbelow.

Recombinant host cells expressing the p48-TAD proteins of this invention can be identified by any of several approaches. Nonlimiting examples include (1) DNA-DNA hybridization with probes complementary to the nucleic acid sequence encoding the p48-TAD protein (Southern blotting); (2) detection of marker gene functions, such as thymidine kinase activity, resistance to antibiotics, and the like (A marker gene can be placed in the same plasmid as the p48-TAD sequence under the regulation of the same or a different promoter); (3) detection of mRNA transcripts by hybridization assays (e.g., Northern blotting or a nuclease protection assay using a probe complementary to the RNA sequence); (4) immunodetection of gene expression (e.g., by Western blotting with antibody to the p48-TAD protein; and (5) PCR with primers homologous to expression vector sequences or sequences encoding the p48-TAD protein. The PCR technique produces a DNA fragment of predicted length, indicating incorporation of the expression system in the host cell. DNA sequencing can be performed by various known methods. See, for example, the dideoxy chain termination method in Sanger et al., 1977, *Proc. Nati. Acad. Sci. U.S.A.* 74: 5463-7.

The p48-TAD polypeptides, e.g., p48-S2C or p48-VP16 TAD, of the present invention can be expressed as recombinant proteins with one or more additional polypeptide domains added to facilitate isolation and protein purification. Nonlimiting examples of protein purification-facilitating domains include metal chelating peptides, such as histidine-tryptophan modules that allow purification on immobilized beads (Porath, 1992, *Protein Exp. Purif.* 3: 263); protein A domains that allow purification on immobilized immunoglobulin; and the FLAGS domain extension/affinity purification system (Immunex Corp.). Other tags such as poly-histidine (HIS) tags and glutathione transferase (GST) tags, as known and used in the art, are also suitable for use. The inclusion of a cleavable linker sequence, such as Factor XA, or enterokinase (Invitrogen), between the purification domain and the p48-TAD coding region is also useful to facilitate purification of the expressed p48-TAD polypeptide.

Further, a host cell strain can be selected for its ability to modulate the expression of the inserted and expressed sequences, or to process the expressed protein in a desired fashion. Such modifications of the polypeptide include, but are not limited to, acetylation, carboxylation, glycosylation, phosphorylation, lipidation and acylation. Post-translational processing which cleaves a nascent form of the protein may also be important for correct folding, insertion and/or function. Different host cells, such as CHO, HeLa, MDCK, 293 (ATCC CRL 1573), WI38, NIH 3T3, HEK293, and the like, have specific cellular machinery and characteristic mechanisms for such post-translational activities, and may be employed to ensure the correct modification and processing of an introduced, heterologous protein.

Examples of protocols useful for detecting and measuring the expression of the p48-TAD transcription regulators using either polyclonal or monoclonal antibodies include, but are not limited to, enzyme linked immunosorbent assay (ELISA), radioimmunoassay (RIA), and fluorescence activated cell sorting (FACS). A two-site, monoclonal antibody-based immunoassay utilizing monoclonal antibodies reactive to two non-interfering epitopes may be utilized. Competitive binding techniques may also be employed (see, for example, Hampton, 1990, *Serological Methods—A Laboratory Manual*, APS Press, St. Paul, Minn. and Maddox et al., 1983, *J. Exp. Med.*, 158:1211).

Not all expression vectors and DNA regulatory sequences will function equally well to express the DNA sequences of this invention. Neither will all host cells function equally well with the same expression system. However, one of ordinary skill in the art can make a selection among expression vectors, DNA regulatory sequences, and host cells using the guidance provided herein and routine skill without departing from the scope of the invention, to achieve expression and purification of the p48-TAD proteins, e.g., p48-S2C or p48-VP16 TAD proteins, for the variety of uses described.

p48-S2C Polypeptide

A particular embodiment of the present invention encompasses a polypeptide comprising all or a portion of the amino acid sequence of the p48-S2C protein (SEQ ID NO:2). Where a portion of the p48-S2C protein is used, the portion most preferably retains function so as to regulate transcription and induce the expression of genes normally regulated by interferon, but in the absence of IFN treatment. In addition, the STAT TAD of the p48-S2C protein may contain one or more mutations or deletions, so long as the product functions to regulate transcription and activate IFN-response genes in the target cells to produce an anti-viral state in the cells in the absence of IFN treatment. For example, the p48-STAT TAD construct can contain the N or C terminal deletions of the TAD, as shown in FIG. 21, such that the STAT TAD portion contains amino acids selected from 747-851, 757-851, 767-851, 747-831, 747-831, 747-821, or 747-812 of STAT2. The p48-STAT TAD construct can also contain internal deletions of the STAT2 TAD, as shown in FIG. 22, such that the STAT TAD portion contains STAT2 TAD with one or more of the following amino acid regions deleted: 757-767, 770-790, 801-805, and 767-811.

p48-VP16 TAD Polypeptide

A further embodiment of the present invention encompasses a polypeptide comprising all or a functional portion of the amino acid sequence of the p48-VP16 TAD protein (SEQ ID NO: 30). In addition, the TAD of the p48-VP16 TAD (i.e. transcriptional activation domain of HSV VP16 preferably comprising amino acids 411-490), can contain one or more mutations or deletions, so long as the product functions to regulate transcription and activate IFN-response genes in the target cells to produce an anti-viral state (inhibit virus infection) in the cells in the absence of IFN treatment.

The p48-TAD polypeptides, e.g., p48-S2C or p48-VP16 TAD polypeptide, can be prepared by methods known in the art. For example, chemical synthesis, such as the solid phase procedure described by Houghton et al., 1985, *Proc. Natl. Acad. Sci. U.S.A.*, 82: 5131-5, can be used. A preferred method involves the recombinant production of protein in host cells transfected within a vector containing polynucleotide sequence(s) encoding p48-S2C or p48-VP16 TAD, as described above. For example, DNA comprising all or a portion of SEQ ID NO:1 or SEQ ID NO:29 can be synthesized by PCR as described above, inserted into an expression vector, and host cells transformed with the expression vector. Thereafter, the host cells are cultured to produce the desired polypeptides, which are isolated and/or purified. Protein isolation and purification are achieved by any one of several known techniques; for example and without limitation, ion exchange chromatography, gel filtration chromatography and affinity chromatography, high pressure liquid chromatography (HPLC), reversed phase HPLC, preparative disc gel electrophoresis.

In addition, cell-free translation systems (Sambrook et al., *Molecular Cloning: A Laboratory Manual*, Cold Spring Harbor Laboratory, Cold Spring Harbor, N.Y., 1989) can be used to produce recombinant p48-TADs, e.g., p48-S2C or p48-VP16 TAD polypeptides or peptides. Suitable cell-free expression systems for use in accordance with the present invention include, but are not limited to, rabbit reticulocyte lysate, wheat germ extract, canine pancreatic microsomal membranes, *E. coli* S30 extract, and coupled transcription/translation systems (Promega Corp., Madison, Wis.). These systems allow the expression of recombinant polypeptides or peptides upon the addition of cloning vectors, DNA fragments, or RNA sequences containing coding regions and appropriate promoter elements.

Protein isolation/purification techniques may require modification of the p48-TAD protein using conventional methods. For example, a histidine tag can be added to the protein to allow purification on a nickel column. Other modifications may cause higher or lower activity, permit higher levels of protein production, or simplify purification of the protein. Amino acid substitutions can be made based on similarities in polarity, charge, solubility, hydrophobicity, hydrophilicity and/or the amphipathic nature of the residues involved. Most preferably, the biological activity or functional activity of the transcription regulator is retained. For example, negatively charged amino acids include aspartic acid and glutamic acid; positively charged amino acids include lysine and arginine. Amino acids with uncharged polar head groups, or nonpolar head groups having similar hydrophilicity values, include the following: leucine, isoleucine, valine; glycine, alanine; asparagine, glutamine; serine, threonine; phenylalanine and tyrosine.

Conservative substitutions of amino acids in the p48-TAD fusion polypeptides of the present invention can include the use of a chemically derivatized residue to replace a non-derivatized residue, with the proviso that the derivatized polypeptide displays the desired biological activity. D-isomers, as well as other known derivatives, may also be substituted for the naturally-occurring amino acids. See, for example, U.S. Pat. No. 5,652,369, issued Jul. 29, 1997. Preferably, conservative substitutions are made without altering the biological activity of the resulting polypeptide. All of the above-described modified polypeptides are included within the scope of the present invention.

In a further embodiment, the present invention includes a p48 polypeptide covalently attached to the transcriptional activation domain of STAT2 (S2C) to form a fusion chimeric, or hybrid protein. In yet another aspect, the p48 polypeptide is covalently attached to a fragment or variant of the STAT2 transcriptional activation domain or a heterologous transcriptional activation domain (TAD).

The fused proteins of the present invention can be formed by synthetic means, chemical conjugation, or by recombinant techniques. For chemical conjugation, the p48 polypeptide and the TAD polypeptide or peptide, or functional portions thereof, are modified by conventional coupling agents for covalent attachment. If recombinant production is employed, an expression vector containing the coding sequence of the TAD is joined to the p48 coding sequence or the coding sequence of a functional portion of the TAD and/or p48. The fusion protein is then expressed in a suitable host cell. The fusion protein may be purified, for example, by molecular-sieve and ion-exchange chromatography methods, with additional purification by polyacrylamide gel electrophoretic separation and/or HPLC chromatography, if necessary.

In another aspect, the present invention includes an expression vector comprising a nucleic acid sequence containing an open reading frame (ORF) that encodes the p48-TAD hybrid interferon fusion polypeptide, including the nucleic acid and polypeptide sequences described herein. The vector further includes regulatory sequences effective to express the ORF in a host cell; such sequences may be endogenous or heterologous (such as a secretory signals recognized in yeast, mammalian cells, insect cells, tissue culture or bacterial expression systems). In the expression vector, regulatory sequences may also include, 5' to the nucleic acid sequence, a promoter region and an ATG start codon in-frame with the hybrid fusion polypeptide coding sequence (chimeric nucleic acid molecule), and 3' to the coding sequence, a translation termination signal followed by a transcription termination signal. Further, the invention includes a method of recombinantly producing a transcriptional regulating hybrid fusion polypeptide using an expression vector. The expression vectors are introduced into suitable host cells and the host cells are then cultured under conditions that result in the expression of the open reading frame sequence (see Example 1).

Functional Expression

Biologically active p48-TAD mRNA, e.g. p48-S2C or p48-VP16 TAD mRNA, can be introduced into host cells, either heterologous or homologous to the vector or polynucleotide molecule, for functional expression and analyses by methods well-known in the art. cRNA (i.e., synthetic RNA from a cDNA construct) or cDNA can be introduced into host cells, such as eukaryotic, including mammalian cells, for example, RBL cells (ATCC CRL 1378) or 293 cells (ATCC CRL 1573), can be transformed, using routine methods in the art. As an example, direct nucleic acid injection can be employed, such as the Eppendorf microinjection system (Micromanipulator 5171 and Transjector 5242), as well as calcium phosphate ($CaPO_4$) precipitation, as practiced in the art (see, e.g., Maniatis et al., Cold Spring Harbor, Molecular Cloning: *A Laboratory Manual*, 1982).

Antibodies

Polyclonal antibodies that are immunoreactive with (and specific for) a given p48-TAD polypeptide, or an immunoreactive fragment thereof, can be purified from antisera of an animal previously immunized with the p48-TAD polypeptide, for example, the p48-S2C or p48-VP16 TAD polypeptide, or an immunoreactive fragment thereof, as immunogen. In addition, monoclonal antibodies can be prepared using protocols and techniques routinely practiced in the art (e.g., Kohler and Milstein, 1975, *Nature*, 256:495). Examples of immunogenic portions of p48-S2C are described in Example 1. Antibody preparation, manipulation, and purification techniques are well known in the art and can be performed using conventional methodologies and protocols.

Therapeutic Agents/Uses p48-TAD nucleic acid molecules can also be used as therapeutic agents following expression of encoded p48-TAD polypeptides that directly activate interferon stimulated genes in target cells, thereby creating an anti-viral, anti-tumor, or anti-cancer state. Vectors can be designed and constructed to direct the synthesis of the desired DNA or RNA or to formulate the nucleic acid molecules as discussed above.

The p48-TAD transcription regulator polypeptide-encoding nucleic acids described herein can be delivered to cells, either as naked DNA or in an expression vector, wherein the cells express the polypeptide. In this way, the p48-TAD transcription regulator polypeptides can be delivered to target cells and activate transcription of interferon stimulated genes. More specifically, the p48-TAD polypeptide coding regions can be ligated into expression vectors, preferably, viral expression vectors, which mediate transfer of the transactivator polypeptide nucleic acid by infection of recipient host cells. Suitable viral vectors include retrovirus, adenovirus, adeno-associated virus, herpes virus, vaccinia virus, polio virus, modified human immunodeficiency virus (HIV), or portions thereof, and the like. See, e.g., U.S. Pat. No. 5,624,820, Episomal Expression Vector for Human Gene Therapy.

The nucleic acid coding region of the p48-TAD fusion proteins can be incorporated into effective eukaryotic expression vectors, which are directly administered or introduced into somatic cells (a nucleic acid fragment comprising a coding region, preferably mRNA transcript, can also be administered directly or introduced into somatic cells). See, e.g., U.S. Pat. No. 5,589,466, issued Dec. 31, 1996. Such nucleic acid and vectors may remain episomal, may be incorporated into the host chromosomal DNA, e.g., as a provirus, or a portion thereof, that includes the gene fusion and appropriate eukaryotic transcription and translation signals, i.e., an effectively positioned RNA polymerase promoter 5' to the transcriptional start site and ATG translation initiation codon of the gene fusion, as well as termination codon(s) and transcript polyadenylation signals effectively positioned 3' to the coding region.

Alternatively, p48-TAD transcription regulator polypeptide DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection, or microparticle bombardment. Furthermore, the novel p48-TAD molecules can be introduced into cells by microinjection or liposome encapsulation. See, e.g., U.S. Pat. Nos. 6,063,629, 5,773,027, and 4,235,871, issued May 16, 2000, Jun. 30, 1998, and Nov. 25, 1980, respectively. These procedures and variations thereof are suitable for ex vivo, as well as in vivo therapies, including use in humans, according to established methods and protocols known in this art.

Once a novel p48-TAD fusion protein is introduced into cells by the techniques described above, it accumulates in the nucleus and binds to target gene promoters via its activated p48 DNA binding domain. The presence of the transcriptional activation domain in the p48-TAD product allows the protein to recruit RNA polymerase and associated factors, thereby activating transcription of the interferon stimulated genes. The p48 protein component comprises the DNA recognition for the native IFN responsive complex. Therefore, the hybrid protein is able to induce the expression of interferon stimulated genes in the absence of IFN or IFN receptor binding. The interferon stimulated genes encode proteins that have potent anti-viral properties.

In accordance with the present invention, a method of activating cellular interferon stimulated genes which are involved in cellular anti-viral effects, growth inhibition and immune regulation is provided. The method involves contacting cells with the p48-TAD fusion protein, or encoding nucleic acid, for example, the p48-S2C or p48-VP16 TAD fusion protein or encoding nucleic acid, in an amount effective to activate transcription of interferon stimulated genes. The determination of effective amounts to use is well within the capability of those skilled in the art, and is also described herein. The cells may be isolated from tissue, or they may comprise tissue, and can be contacted in vitro, ex vivo, or in vivo. The p48-TAD fusion protein can be introduced into the cells as described supra using techniques known in the art. Such cells include, for example, tumor or cancer cells, e.g. ovarian cancer cells, cervical cancer cells, lung cancer cells, liver cancer cells, stomach cancer cells, esophageal cancer cells, breast cancer cells, prostate cancer cells, colon cancer cells, kidney cancer cells, etc., and virus-infected cells, e.g. HSV-infected cells, hepatitis-virus-infected cells (HAV, HBV, HCV, HEV, etc), HIV-infected cells, papilloma-virus infected cells and the like. The p48-TAD fusion proteins can serve as agents that block, inhibit, or eliminate viral infection or uncontrolled cell growth, as in cancers and tumors.

p48-TAD-Containing Compositions

Pharmaceutically useful compositions comprising p48-TAD polynucleotide or polypeptide sequences, or variants and analogs which preferably have transcriptional activity, can be formulated as compositions, preferably physiologically acceptable compositions, according to known methods, such as by admixture with a pharmaceutically acceptable carrier, diluent, or excipient. Such compositions may also include compounds which activate cellular interferon stimulated genes (ISGs). The compositions can comprise more than one p48-TAD polynucleotide or polypeptide molecule. Examples of suitable carriers, and the like, and methods of formulation can be found in the latest edition of *Remington's Pharmaceutical Sciences,* 18th Ed., 1990, Mack Publishing Co, Easton, Pa. To formulate a pharmaceutically acceptable composition suitable for effective administration, preferably in vivo, or even ex vivo, such compositions will contain an effective amount of the polypeptide, DNA, RNA, or compound activator.

Pharmaceutical compositions of the present invention are administered to an individual in amounts effective to treat or prevent infection caused by a broad range of virus types, or to treat uncontrolled cell growth, e.g. tumor or cancer cell growth. The effective amount may vary according to a variety of factors, such as an individual's physical condition, weight, sex and age. Other factors include the mode and route of administration. These factors are realized and understood by the skilled practitioner and are routinely taken into account when administering a therapeutic agent to an individual.

Pharmaceutical compositions suitable for use in the present invention include compositions wherein the active ingredients are contained in an effective and sufficient amount to directly activate interferon stimulated genes and produce an anti-viral state in the cells. The determination of an effective dose is well within the capability of those skilled in the art. The therapeutically effective dose can be estimated initially either in cell culture assays, e.g., of neoplastic cells, or in animal models, usually mice, rabbits, dogs, pigs, rats, monkeys, or guinea pigs. The animal model is also used to achieve a desirable concentration range and route of administration. Such information can then be used to determine useful doses and routes for administration in humans. In addition, dosages may be chosen which result in cellular concentrations of p48-TADs which are similar to amounts that are effective to cause activation of ISGs in vitro. A therapeutically effective dose refers to that amount of a p48-TAD fusion protein which ameliorates, reduces, inhibits or eliminates the symptoms or condition. The exact dosage is chosen in view of the patient to be treated, the route of administration, the severity of disease, and the like.

The daily dosage of the products may be varied over a wide range, for example, from about 0.01 to 1,000 mg per adult human/per day. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course, it will be understood by the skilled practitioner that the dosage level will vary depending upon the potency of the particular compound, and that certain compounds will be more potent than others.

In addition, the dosage level will vary depending upon the bioavailability of the compound. The more bioavailable and potent the compound, the less amount of the compound will need to be administered through any delivery route, including, but not limited to, oral delivery. The dosages of the p48-TAD transcriptional regulators are adjusted if combined in order to achieve desired effects. On the other hand, dosages of the various agents or modulating compounds may be independently optimized and combined to achieve a synergistic result wherein the pathology is reduced more than it would be if one single agent or compound were used alone. Those skilled in the art know to employ different formulations for nucleotides than for proteins. Similarly, the delivery of polynucleotides or polypeptides will be specific to particular cells and conditions.

The pharmaceutical compositions may be provided to an individual in need of therapeutic treatment by a variety of routes, such as, for example, subcutaneous, topical, oral, intraperitoneal, intradermal, intravenous, intranasal, rectal, intramuscular, and within the pleural cavity. Administration of pharmaceutical compositions is accomplished orally or parenterally. More specifically, methods of parenteral delivery include topical, intra-arterial, intramuscular, subcutaneous, intramedullary, intrathecal, intraventricular, intravenous, intraperitoneal, intranasal administration, or via the pleural cavity.

The present invention also provides suitable topical, oral, systemic and parenteral pharmaceutical formulations for use in the novel methods of treatment comprising a p48-TAD fusion protein transcription regulator as active ingredient described herein. The compositions containing p48-TADs can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, the therapeutic compounds may also be administered in intravenous (both bolus and infusion), intraperitoneal, subcutaneous, topical (e.g., transdermal patches, with or without occlusion), or intramuscular form, all using forms well known to those of ordinary skill in the pharmaceutical arts.

In another of its aspects, the present invention provides targeting therapies to deliver an active agent, such as a p48-TAD fusion polypeptide, antibodies, peptides and nucleic acids of the present invention, more specifically to certain types of cells, for example, by the use of targeting systems such as antibodies or cell specific ligands. Targeting may be desirable for a variety of reasons, e.g., if an agent is unacceptably toxic, or if it would require too high a dosage, or if it would not otherwise be able to enter the target cells.

Rather than administering an active agent directly, the agent can be produced in the target cell, e.g., in a viral vector as described hereinabove, or in a cell-based delivery system, e.g., as described in U.S. Pat. No. 5,550,050, or published international application numbers WO 92/19195, WO 94/25503, WO 95/01203, WO 95/05452, WO 96/02286, WO 96/02646, WO 96/40871, WO 96/40959 and WO 97/12635, designed for implantation in a patient, i.e., an ex vivo type of therapy. The vector can be targeted to the specific cells to be treated, or it can contain regulatory elements which are more tissue specific to the target cells. The cell-based delivery system is designed to be administered to a patient, or implanted in a patient's body at the desired target site and contains a coding sequence for the active agent. Alternatively, the agent can be administered in a precursor form for conversion to the active form by an activating agent produced in, or targeted to, the cells to be treated (see, e.g., EP 425 731 A or WO 90/07936).

As described supra, the applications of the novel p48-TAD, transcription regulators include gene therapies suitable for ex vivo, as well as in vivo treatments, to target and affect a number of different virus types (see FIG. 11). For example, the viral vector system comprising p48-TAD, and more specifically, the p48-S2C or p48-VP16 TAD described herein, is utilized as an in vivo therapeutic agent for Hepatitis C. Moreover, ex vivo therapies can include the transfection of bone marrow isolated from a patient with p48-TAD expression system, and the subsequent implantation of the transfected bone marrow to the patient following radiation therapy. Additional applications may include a liposomal encapsulated expression plasmid for the p48-TAD fusion protein, which is applied to the infected area by a cream or ointment in order to target viral infections, including but not limited to, Herpes and Varicella Kaposi's Sarcoma (KHSV) viruses. For respiratory viruses, a liposome encapsulated expression plasmid for p48-TAD may be inhaled as an aerosol. In the applications described herein, the novel p48-TAD fusion protein transcription regulators directly activate IFN-response genes in the target cells to induce anti-viral activity which includes inhibition of cell cycle progression, cell proliferation, disruption of the viral replicative life cycle, and apoptosis, as well as having an anti-tumor or anti-cancer effect.

EXAMPLES

The following examples as set forth herein are meant to illustrate and exemplify the various aspects of carrying out the present invention and are not intended to limit the invention in any way.

The Examples do not include detailed descriptions for conventional methods employed, such as in the construction of vectors, the insertion of cDNA into such vectors, or the introduction of the resulting vectors into the appropriate host cells. Such methods are well known to and conventionally practiced by those skilled in the art and are described in numerous publications, for example, Sambrook, Fritsch, and Maniatis, *Molecular Cloning: A Laboratory Manual*, $2^{nd}$ Edition, Cold Spring Harbor Laboratory Press, Cold Spring Harbor, N.Y., USA, (1989).

Example 1

Materials and Methods

Cell Culture and Transfection. Human fibrosarcoma 2fTGH, U6A (2fTGH derivative), and 293T cells were maintained in DMEM supplemented with 100/9 cosmic calf serum (Hyclone). Transfection of cells with cDNAs was carried out by standard $CaPO_4$ procedures (see, e.g., Horvath et al., 1995, *Genes and Devel.*, 9: 984-994).

Fluorescence Microscopy. For indirect immunofluorescence, cells grown on chamber slides were fixed in 1:1 methanol:acetone at −20° C. for 15 minutes, washed with PBS, then blocked with 1% BSA in PBS for 15 minutes. Samples were stained with p48 antiserum (diluted 1:50 in 1% BSA/PBS solution) and FITC-conjugated goat anti-rabbit for 1 hour each at 37° C. Green fluorescent protein (GFP) fluorescence of transfected cells was observed at 24 hours post-transfection with a fluorescence microscope (Olympus BX60) with the fluorescein filter set. Images were then captured with a CCD camera (Optronics) at 40 times magnification.

Plasmid Construction. Inserts for the p48-S2C and p48-VP16 TAD hybrid cDNAs were created by standard PCR techniques and oligonucleotide-primed mutagenesis using Vent polymerase (NEB). The primer sequences used to generate the p48-S2C and p48-VP16 TAD gene fusions are as follows:

| | | |
|---|---|---|
| T p48, | 5'-CCCGGATCCCCGCCATGGCATCAGGCAGGGCACGC-3'; | (SEQ ID NO: 20) |
| S2 REV 3', | 5'-GGGGCGGCCGCCTAGAAGTCAGAAGGCATC-3'; | (SEQ ID NO: 21) |
| p48-S2C T, | 5'-GCCATTCTGTCCCTGGTGGGGCCAGAGCTAGAGTCT-3'; | (SEQ ID NO: 22) |

```
                          -continued
p48-S2C B,      5'-AGACTCTAGCTCTGGCCCCACCAGGGACAGAATGGC-3';    (SEQ ID NO: 23)

VP16 Rev 3',    5'-GGGGCGGCCGCCTACCCACCGTACTCGTC-3';           (SEQ ID NO: 24)

p48 VP16 T,     5'-GCCATTCTGTCCCTGGTGTCGACGGCCCCCCCA-3';        (SEQ ID NO: 25)

p48-VP16 TAD B, 5'-TGGGGGGGCCGTCGACACCAGGGACAGAATGGC-3'.        (SEQ ID NO: 26)
```

In brief, two PCR fragments were first generated: a full-length p48 fragment with the 5'-end of its antisense strand complementary to the 5'-end of the STAT2 sense strand fragment or the 5'-end of the VP16 sense strand fragment. These products were then gel-purified and combined for use as templates for a second PCR reaction, with primers for N-terminal p48, C-terminal STAT2, and C-terminal VP16. Site-directed mutagenesis was performed with a four-primer PCR method (see, e.g., Horvath et al., 1995, *Genes and Devel.*, 9: 984-994). Inserts for GST-STAT Transcriptional Activation Domain (TAD) fusion cDNAs were also generated by PCR amplification with in-frame Bam HI and Not I restriction sites, and fragments were cloned into the pGEX5.1 vector (Amersham Pharmacia). The PCR-generated insert for p48-DBD (encoding residues 1-200 of p48) was cloned into pCDNA3. All constructs were verified by DNA sequencing. Both the wild type and mutant GFP-p48 fusion cDNAs and the FLAG-tagged STAT2 cDNA were described previously (see, Lau et al., 2000, *PNAS*, 97: 7278-7283).

Electrophoretic Mobility Shift and Reporter Gene Assays. Electrophoretic gel mobility shift assays were carried out essentially as described in Horvath et al., 1995, *Genes and Devel.*, 9: 984-994. Double stranded oligonucleotides representing the ISG15 ISRE element were radiolabelled by filling in protruding ends with $^{32}$P using the Klenow fragment of DNA polymerase. Cell extracts were mixed with $1 \times 10^5$ cpm of probe for 15 minutes prior to separation on a 5% polyacrylamide-gel. For antibody supershifts, 0.1 μl of antibody was added to the reaction during incubation. Gels were dried and subjected to autoradiography. For detection of GAL4, a DNA binding domain fusion, constructs in a reporter gene assay, 293T, U3A, and U6A cells were transiently transfected with either vector alone or GAL4-p48 fusion constructs, along with a reporter gene containing 5 GAL4 UAS elements fused to the luciferase gene. For the detection of p48-STAT hybrid protein activity, 293T cells were transiently co-transfected with hybrid proteins and a reporter gene containing 5 copies of the ISG54 ISRE element upstream of a TATA box and firefly luciferase ORF. Luciferase assays were normalized to β-galactosidase activity derived from 1 μg of co-transfected CMV-lacZ.

Cell Extracts and Protein Assays. Antibodies against p48 (C-20), the C-terminal 20 amino acids, STAT2 (C-20), and CBP (A-22) were obtained from Santa Cruz Biotechnology (Santa Cruz, Calif.), and used according to manufacturers' instructions. For protein analyses, cytoplasmic and nuclear extracts, or whole cell extracts were prepared as described. Proteins were separated by SDS-PAGE and transferred to nitrocellulose filters and immunoblotted by standard procedures. Preparation of GST fusion proteins was carried out by induction of *Escherichia coli* containing the fusion vector at 30° C. with 0.1 mM IPTG. Following lysis by sonication, GST fusion proteins were purified on glutathione-Sepharose beads (Pharmacia) and washed with phosphate-buffered saline (PBS). The proteins were retained on the beads for affinity chromatography. 2fTGH cells metabolically labeled with [$^{35}$S]-methionine (NEN) for 16 hours and extracts were prepared. Extracts were incubated 2 hours with equal amounts of GST fusion proteins, and washed three times in sample buffer. After washing, the specifically bound proteins were eluted by boiling in SDS-gel loading buffer and subjected to electrophoresis and autoradiography. For purification of His-tagged proteins, extracts with expressed proteins were purified by incubation with Ni-NTA resin (Qiagen) and subsequently eluted with imidazole.

RNA analysis. Total RNA was prepared from confluent 6-cm cell culture dishes by using Trizol reagent (GIBCO BRL), digested with DNase 1, and subjected to reverse transcriptase PCR (RT-PCR) analysis. RNA was reverse transcribed with SuperScript II RNase H Reverse Transcriptase (GIBCO BRL) using random hexamer primers. A mock reaction was carried out with no reverse transcriptase added (–RT). One-tenth of the resulting cDNA product was used as template for 25 cycles of PCR in the presence of [α-$^{32}$P]-dATP (NEN) using specific primers for the ISGs (Interferon Stimulated Genes), ISG15, ISG54 or glyceraldehyde-3-phosphate dehydrogenase (GAPDH). As a control for genomic DNA contamination, PCR was carried out with GAPDH primers using the mock (–RT) reaction products as templates. Following gel electrophoresis, products were detected by autoradiography. The primer sequences used included:

```
ISG15 a,
5'-CAACGAATTCCAGGTGTC-3';           (SEQ ID NO: 8)

ISG15 b,
5'-CCCTTGTTATTCCTCACC-3';           (SEQ ID NO: 9)

ISG54a,
5'-AATGCCATTTCACCTGGAACTTG-3';      (SEQ ID NO: 10)

ISG54 b,
5'-GTGATAGTAGACCCAGGCATAGT-3';      (SEQ ID NO: 11)

GAPDH a,
5'-GTGAAGGTCGGAGTCAAC-3';           (SEQ ID NO: 12)
and

GAPDH b,
5'-TGGAATTTGCCATGGGTG-3'.           (SEQ ID NO: 13)
```

Autoradiography results were quantified by phosphorimaging analysis (Molecular Dynamics).

Example 2

Hybrid p48-S2C Fusion Protein Activates ISRE Dependent Transcription

The following experiments examined the transcriptional function of ISGF3 in a physiological context with the ability to direct transcription from endogenous loci as a final output. To isolate the intrinsic STAT transcriptional activation functions in a native setting, fusions of p48 with the transcriptional activation domains (TADS) of STAT1 and STAT2 were generated to reveal if these activation domains functioned in the context of an endogenous ISGF3 dependent promoter. FIGS.

12 and 13 provide the nucleic acid sequence (SEQ ID NO: 14) and the amino acid sequence (SEQ ID NO: 15) of STAT1, respectively.

For the following experiment, amino acid sequence structure prediction analysis indicated that the C-terminal 104 amino acids of STAT2 (S2C) could encompass a single protein fold. The coding region for the STAT2 TAD was fused to the p48 open reading frame (ORF) and the chimeric cDNA was cloned into a mammalian expression vector to create the hybrid p48-S2C fusion protein. For comparison, the C-terminal 38 amino acids of STAT1, which forms the STAT1 TAD (S1C) and comprises the difference between STAT1α and its transcriptionally inactive splice variant, STAT1β, were also fused to p48 to create p48-S1C. To examine reporter gene expression, 5 copies of an ISRE element from the interferon Stimulated Gene ISG54, was cloned upstream of a minimal promoter driving the expression of the firefly luciferase (Luc) gene. The ISRE-Luc reporter reflects induction in response to IFNα in most cell lines studied.

As illustrated in FIGS. 14A and 14B and 15A-15C, the hybrid protein p48-S2C activated the reporter gene by 40-50 fold and was independent of IFN treatment. However, the p48-S1C hybrid protein was much less active in ISRE reporter gene assays, inducing transcription only weakly in reporter gene assays. Furthermore, the p48-S1C protein was inactive on endogenous ISG54 gene expression. FIGS. 14A and 14B graphically depict the luciferase activity of empty vector, p48 or p48-S2C expression vectors in 293T cells using the ISRE-Luc reporter to illustrate the expression and activity of p48-S2C fusion protein. FIG. 14A shows the luciferase activity of the empty vector, p48, and p48-S2C. The insert in FIG. 14A is an anti-p48 Western blot of luciferase extracts. FIG. 14B illustrates IFN treatment. The IFN treatments were conducted for 5 hours, and each bar of the graph reflects the average of triplicates.

FIGS. 15A-15C illustrate the expression and activity of p48-S2C fusion proteins in STAT-deficient cell lines by tabulating the luciferase activity of empty vector p48, or the p48-S1 C or p48-S2C expression vectors in 2fTGH cells and STAT-deficient daughter cell lines using the ISRE-Luc reporter. The STAT-deficient daughter cell lines include U3A, which is STAT1 deficient, and U6A, which is STAT2 deficient. Relative luciferase activity data are normalized to co-transfected beta galactosidase, and each bar of the graph reflects the average of triplicates.

To determine if the activity of the p48-S2C chimeric activator required the presence/activity of endogenous STAT1 or STAT2, assays were carried out in STAT1-deficient U3A cells, STAT2-deficient U6A cells, or parental 2fTGH cells. As demonstrated in FIGS. 14A, 14B, and 15A-15C, p48 protein and p48-S1C fusion proteins did not activate transcription, while the p48-S2C fusion was highly active in all cell lines. In addition, as indicated in FIG. 14B, the high level of activity of p48-S2C was not altered by stimulation with IFNα, but a small increase was observed following IFNγ-stimulation, consistent with contributions by endogenous IFNγ-activated STAT1 dimers interacting with p48 to heighten transcriptional responses. These results indicate that only the novel p48-S2C fusion protein has intrinsic transcriptional activity conferred by the STAT2 transcriptional activation domain (TAD).

Example 3

Use of an HSV VP16 TAD as a p48 Activator

As discussed above according to the present invention, any transcriptional activating domain (TAD) of any protein or peptide sequence can function in activating inert p48, or the p48 DNA binding domain alone, to function as an ISG activator. In this example, a small but potent viral TAD from HSV VP16 was tested for its ability to activate transcription. The transcriptional activation domain of HSV VP16 serves as a model of a "generic" TAD and was used to test its ability to activate the transcription of ISGs because (1) it represents a more discrete unit, compared with STAT2, to minimize the bulk of the fusion protein used in experiments with STAT2 TAD; (2) it can be better manipulated in terms of strength of transcriptional response; and (3) it served as an example of a non-STAT TAD available in the form of a cDNA plasmid.

In the following experiments, 293T cells were transfected with the ISRE-luciferase reporter and p48, p48-S1C, p48-S2C, or p48-VP16 TAD vectors, and luciferase activity was determined using the co-transfected ISRE-Luc reporter. Furthermore, to examine gene expression, an endogenous mRNA analysis was performed using 293T cells transiently transfected with p48-VP16 TAD fusion protein or with an empty vector (CON). The total RNA was isolated and processed for RT-PCR analysis at 12 and 24 hours post-transfection.

Figure 32A:
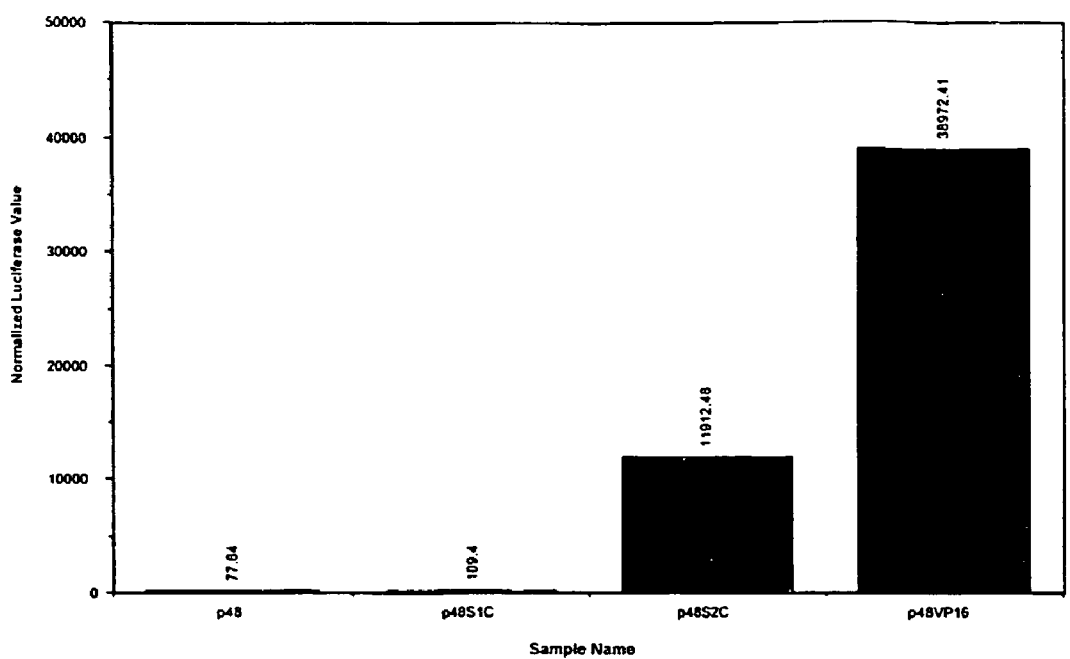
FIGS. 32A-32B illustrate the transcriptional activity of p48-VP16 TAD, i.e., p48 fused to the TAD of HSV VP16.
Figure 32B:
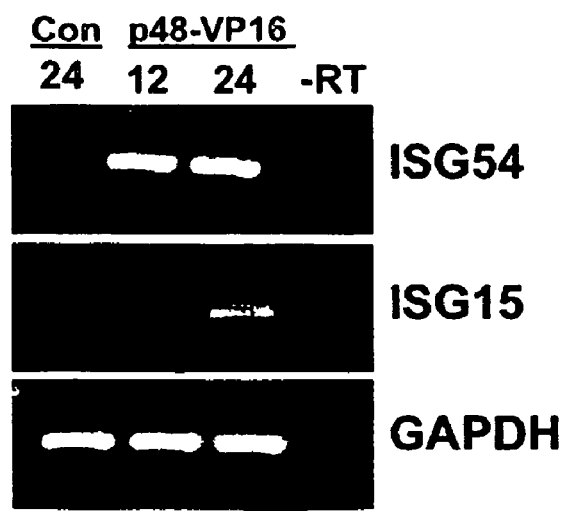
Figure 34:
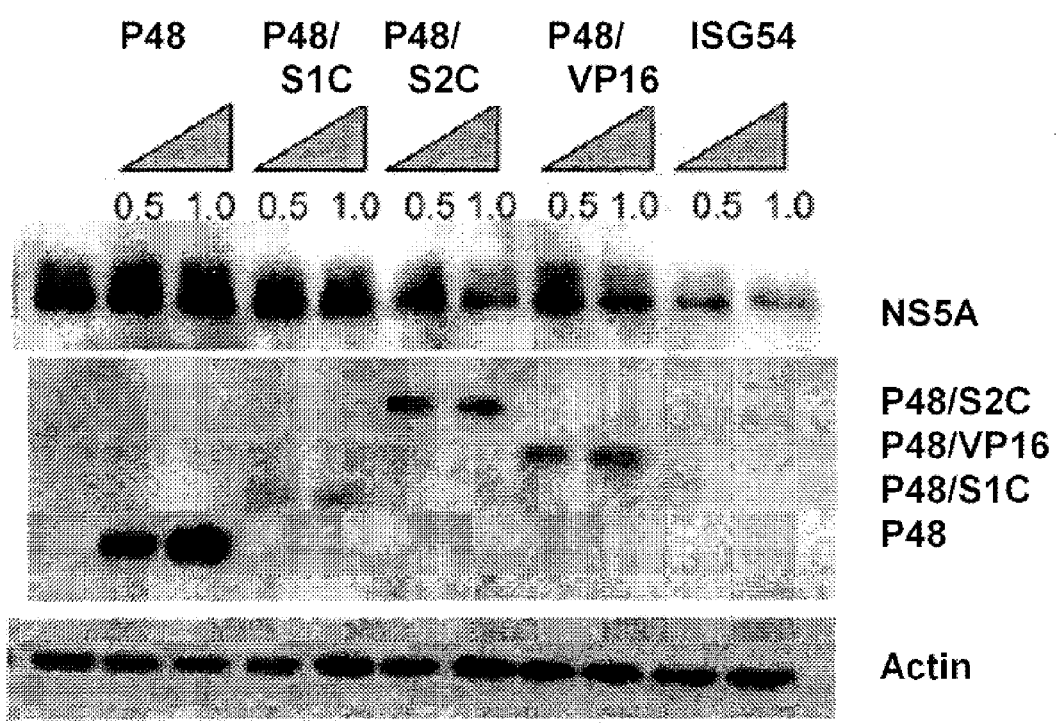
FIG. 34 compares the inhibition of a Hepatitis C virus replicon by the p48-TAD hybrid fusion proteins, p48-S1C, p48-S2C, p48-VP16.

As illustrated in FIG. 32A, expression of the p48-VP16 TAD fusion protein in 293T cells resulted in potent ISRE-directed reporter gene activity, approximately threefold higher than observed with p48-S2C. In addition, as illustrated in FIG. 32B, expression of p49-VP16 TAD was able to induce transcription of both ISG15 and ISG54. In FIGS. 32A and 32B, the p48-VP16 TAD fusion protein is labeled as "p48-VP16". These results indicate that the p48-VP16 TAD fusion protein has intrinsic transcriptional activity conferred by the VP16 transcriptional activation domain. Further, despite the qualitative differences in the functional activity of the STAT2 and VP16 TADs, both were able to turn p48 into an ISG activator.

Example 4

Hybrid p48-S2C Fusion Protein Activates Endogenous Interferon Stimulated Gene (ISG) Transcription In this example, the ability of the p48-S2C hybrid protein of the present invention to activate endogenous ISG15 and ISG54 gene transcription was evaluated. The p48-S2C hybrid proteins were expressed in cells, and total RNA was extracted and subjected to RT-PCR with ISG15 and ISG54 specific primers, or control primers specific for the cellular enzyme glyceraldehyde 3-phosphate dehydrogenase (GADPH), in the presence of radiolabelled deoxynucleoside triphosphate. As illustrated in FIG. 16, levels of mRNA transcribed from ISG54 and ISG15 in cells transfected with the p48-S2C transcription regulator were comparable to the mRNA levels generated by treatment of cells with IFNα. In FIG. 16, 293T cells were transfected with vector (V) or p48 constructs as indicated. At 48 hours post transfection, total RNA was prepared, reverse transcribed, and subjected to PCR with ISG54 and ISG15 specific or control primers. Also, untransfected cells were treated with IFNs for 12 hours prior to lysis.

Example 5

Hybrid p48-S2C Fusion Protein Duplicates IFN Biological Responses

IFN signaling through ISGF3 has the principle biological outcome of creating an anti-viral state. The p48-S2C fusion protein of the invention was tested with respect to both aspects of IFN action. The results illustrate substantial imitation of IFN responses by the p48-STAT2 TAD protein in a physiological assay milieu.

The following assays were conducted to correlate the observed transcriptional properties of hybrid p48-S2C fusion proteins with IFN biological responses. For initial experiments, U3A cells (STAT1 deficient/IFN unresponsive) were transfected with empty vector, p48, p48-S1C, and p48-S2C cDNAs. A standard assay for virus-induced cytopathic effects was used to determine the ability of the expressed cDNAs to protect the cells (Friedman, 1981, *Interferons: A Primer*; Horvath and Darnell, 1996, *J. Virol.*, 70: 647-650). The cells were placed in 96-well plates and the wells were infected with serially diluted vesicular stomatitis virus (VSV) at $10^7$ to $10^2$ pfu per well. After 20 hours, the plates were washed and surviving cells were stained with methylene blue. Since this reagent stains only the nucleic acids of the intact cells remaining on the plate, it provides a simple means to determine the ability of an expressed protein to protect against virus-induced cytopathic effects. The stain remaining after extensive washing was dissolved in methanol, and quantified with a spectrophotometer.

Figure 17:
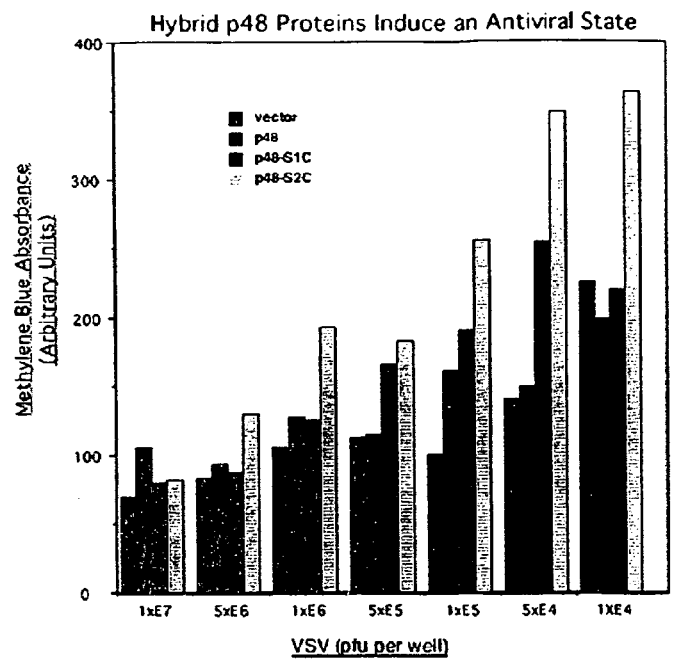
FIG. 17 illustrates the anti-viral effects of p48-STAT TAD fusion proteins.

The results in FIG. 17 reveal a hierarchy in anti-viral properties which directly corresponds to the protein's transcriptional properties. At the highest input virus concentration (multiplicity of infection (MOI) 1000 ($5 \times 10^7$ pfu), little protection was observed. However, even at MOI of 100 ($5 \times 10^6$ pfu), the p48-S2C protein expression protected cells from infection with VSV. This effect was more pronounced with lower MOI, but in all cases, p48 alone had little anti-viral effect, and p48-S1C was weakly protective. This result supports the conclusion that the p48-S2C fusion protein can induce an anti-viral state, thus protecting cells from viral infection, such as VSV infection.

Example 6

Hybrid p48-S2C Fusion Protein Confers Innate Anti-viral Immunity

Figure 18A:
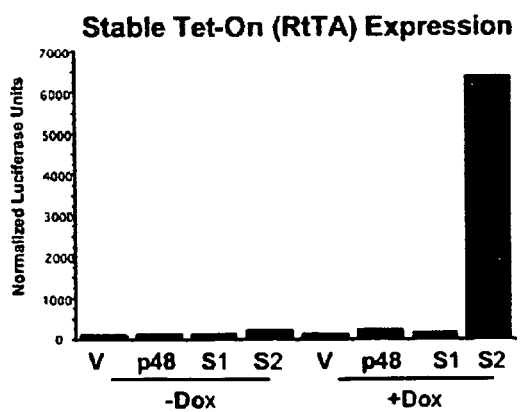
FIGS. 18A and 18B illustrate transcriptional activation by tetracycline transactivator-driven p48-S2C fusions.
Figure 18B:
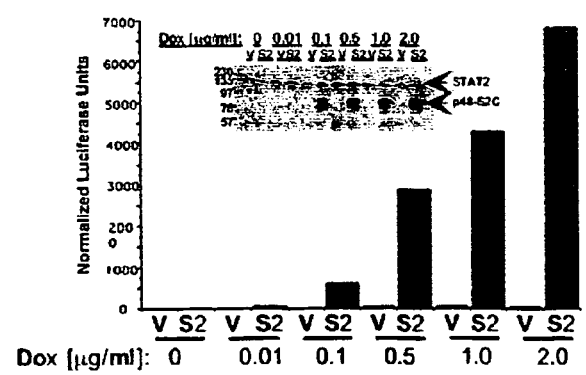

In order to more carefully control expression and to better imitate the transient activation of ISG transcription in a stable expression system, vectors were created for inducible expression of the p48-STAT transgene using a tetracycline (Tet) regulated promoter. The p48, p48-S1C, and p48-S2C open reading frames were subcloned into the Clontech plasmid, pBI, which contains a Tet regulated promoter for mammalian expression. As illustrated in FIGS. 18A and 18B, expression of these proteins can be tightly regulated using the Tet-On (RtTA) expression system as the basal activity is low and the response can be tightly controlled by Tet dosage.

In addition, several independent clones were isolated (FIGS. 19A-19C) and tested for anti-viral effects in a two-step procedure that measured resistance to virus-induced cytopathic effects in the first step and suppression of virus replication in the second step. Typical results from both steps of this assay procedure are illustrated in FIGS. 20A-20E. Essentially, cells were assayed for resistance to VSV, a representative and IFN-sensitive virus. The results from both steps of the assay indicated that expression of p48-S2C of the invention, but not p48 or p48-S1C, protected the cells from virus-induced death and also blocked virus replication. The p48-S2C fusion protein provided a 2-3 log change in virus induced cytopathic effect (CPE) endpoint and a 3-4 log decrease in infectious virus yield. Significantly, FACS analysis illustrated that this anti-viral response occurred in the absence of cell cycle arrest or apoptosis.

FIGS. 19A-19C illustrate Tet-inducible expression of p48, p48-S1C, and p48-S2C in several stable cell lines. Depicted in FIGS. 19A and 19B are independent cloned cell lines that were grown in the presence (+) or absence (−) of 1 μg/ml Doxycycline (Dox) for 24 hours, and then processed for anti-p48 immunoblotting (Western, anti-p48 antibody). The positions of p48, p48-S1C, and p48-S2C are indicated. Because p48-S1C co-migrates with a non-specific (NS) cellular protein, the blot was re-probed with antiserum for STAT1 C-terminus (Western anti-Stat1C antibody) (FIG. 19C). Prestained molecular weight marker positions are indicated at the left side of the blots of FIGS. 19A-19C.

Figure 20A:
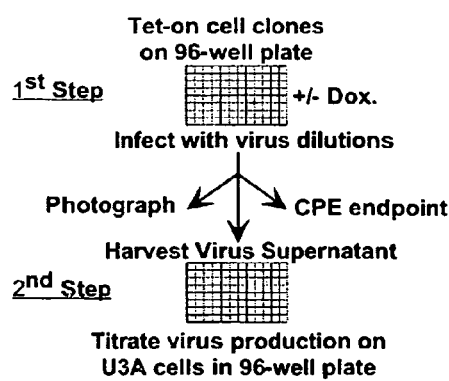
FIGS. 20A-20E illustrate a two step assay and the results thereof for determining anti-viral activity of tetracycline-induced p48-S2C stable cell lines.

FIGS. 20A-20E illustrate a two-step assay for determining anti-viral activity of tetracycline-induced p48-TAD stable cell lines. Tet-regulated cells (p48, p48-S1C, and p48-S2C), as described above, were plated in 96-well dishes and cultured both with or without doxycycline for 48 hours. Cells were then infected with serially diluted virus (VSV; 1:5 dilution series) for 16 hours, and then photographed. The supernatants were harvested and the remaining cells were stained with methylene blue to determine the extent of protection from virus-induced cytopathic effects (CPE). The harvested supernatants were then serially diluted and used to infect fresh monolayers of U3A cells in 96-well plates in order to measure their relative infectious titer, thereby indicating the degree of virus replication inhibition. FIG. 20A demonstrates that the anti-viral state was induced by the Tet-driven p48-S2C fusion protein.

Figure 20B:
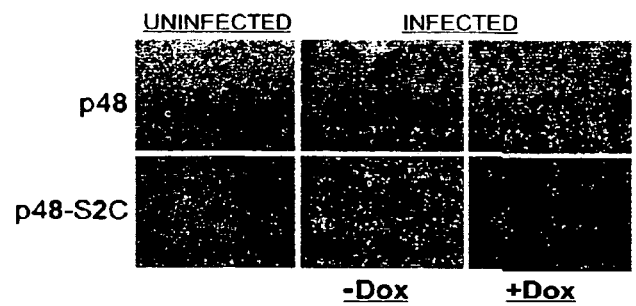

FIG. 20B illustrates the cytopathic effect assay which compared p48 and p48-S2C cell lines in a challenge with a VSV infection. Representative micrographs of uninfected or infected cells are illustrated (MOI=5, 16 h pi). When cells were treated with Dox (1 μg/ml; 24 hours), no difference in the cytopathic endpoint was apparent in cells expressing only p48, but in both cell lines expressing p48-S2C, Dox induced protection from virus infection. Uninfected monolayers were tightly adherent and flattened, but infection caused detachment and death. Only Dox-induced p48-S2C cells had an intact monolayer at this dilution, due to anti-viral effects conferred by the expression and function of the hybrid protein.

Figure 20C:
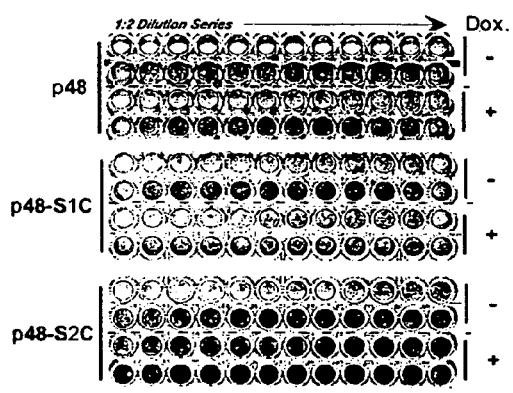
Figure 20D:
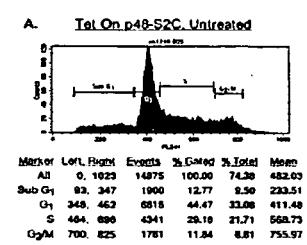
Figure 20E:
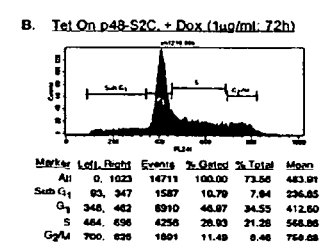

FIG. 20C illustrates that the suppression of virus replication was conferred by the Tet-driven p48-STAT2 TAD fusion construct. Supernatants from untreated (−) or Dox-treated (+) p48, p48-S1, and p48-S2C expressing cell lines were titered in two rows of a fresh 96-well plate of U3A cells (1:2 dilutions). No differences in virus titers recovered from induced versus uninduced p48 or p48-S1C lines were detected, but induction of p48-S2C strongly inhibited virus production, resulting in virus low titers. Supernatants were harvested from MOI=5 infections. FIGS. 20D and 20E illustrate that expression of p48-S2C did not alter the cell cycle profile. Tet-regulated p48-S2C cells were untreated (FIG. 20D) or treated (FIG. 20E) with Dox for 72 hours, and then were processed for propidium iodide DNA staining and flow cytometric analysis. No significant cell cycle alterations were detected as a result of induced p48-S2C expression.

Example 7

Hybrid p48-S2C Fusion Protein for Providing Innate Anti-viral Immunity in Vivo

In order to test the ability of p48-S2C to function in an animal model, several approaches can be taken. One approach includes delivering the cDNA expression vector or p48-S2C protein directly to the site of respiratory virus infection (e.g. Influenza) using an aerosolized plasmid or liposome encapsidated preparation. Accordingly, the IFN-anti-viral state is then established, and infection by a subsequent virus inoculum can be prevented. A second method entails constructing a tissue-specific inducible transgene to be introduced into the germline of transgenic mice. Induction of the transgene provides anti-viral responses to the targeted tissue. A third method involves bone marrow transplantation. After bone marrow is removed from a mouse, the bone marrow cells are cultured with recombinant retroviruses that introduce the transgene. The engineered marrow cells are then reintroduced into irradiated mice (i.e., bone marrow deficient mice). The transplanted cells repopulate the mouse with p48-S2C transgenic cells, which can provide resistance to lymphotropic viruses, such as LCMV.

For the approaches discussed above, control experiments include mock-transgenic animals (or an inert transgene like beta-gal or GFP), p48 alone, and also p48-S1C. Expression of the transgene is monitored by immunoblotting and immunohistochemical localization in the target tissue. In addition, the amount of virus in the inoculum is tested over a range to indicate the effectiveness of transgene expression.

Example 8

Molecular Dissection of the STAT2 Transcriptional Activation Domain (TAD)

In this example, comparison of the STAT2 TAD, comprising the C-terminal 104 amino acids, (S2C), with the STAT1 TAD (C-terminal 38 amino acids; SC1), revealed that the p48-S1C fusion was weaker than the p48-S2C fusion. Thus, the C-terminal 104 amino acids of STAT2 were selected as the primary TAD of the ISGF3 complex.

The STAT2 TAD was dissected to evaluate the transcriptional activity of STAT2. Additional p48-STAT2 hybrids were constructed in which a number of amino acids were truncated from the N or C terminus of the transcriptional activation domain. FIG. 21 depicts the truncations of the STAT2 TAD. Transient luciferase assays were conducted to compare the transcriptional activities of the p48-S2C construct and the TAD variants. FIG. 22A illustrates the luciferase activity of the various p48 hybrid constructs, each bar of the graph reflects the average of triplicate experiments and the standard deviation is indicated. The standard deviations for FIG. 22A are as follows: p48 n=6; S1C n=2; S2C n=6; N10 n=4; N20 n=3; C20 n=2; C30 n=2; C40 n=2; 757-767 n=2; 770-790 n=2; 801-805 n=4; 767-811 n=4; K811A n=5.

It is apparent from the results that mutations in predicted TAD regions alter, but do not eliminate, the transcriptional activity of p48-S2C. Deletion of amino acids 747-757 (N20) or C-terminal truncation (C40) produced proteins with about 30-40% activity. Internal deletions also affected activity to varying degrees, with deletions of the following amino acid regions, 757-767, 767-811, or 801-805, producing proteins that were partially active. Deletion of the direct repeat sequence (770-790) or mutations of lysine 811 caused a complete loss of response in this assay.

FIG. 22B illustrates a comparison of the relative activities of several p48-S2C constructs tested. The value for the p48-S2C construct was normalized to 100% and the p48-TAD variants were expressed as a percentage of the p48-S2C value. For a given hybrid construct, the graphical values represent the average of multiple independent triplicate experiments. Thus, the experimental results demonstrate that deletion of either the N-terminus or the C-terminus retains partial activity. This result indicates that this domain can be further subdivided into two or more sub-domains required for transcription functions, and that at least two protein interaction sites exist in the STAT2 TAD which can be used separately or in combination for mediating chromatin remodeling or RNA polymerase co-activation.

Figure 23A:
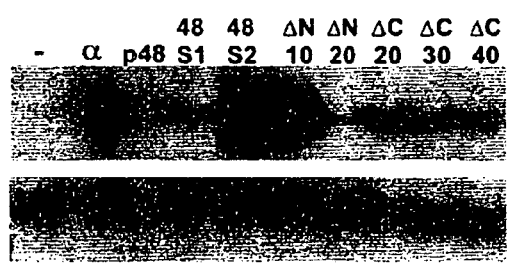
FIGS. 23A and 23B illustrate ISG54 endogenous gene induction by p48-S2C fusion proteins.
Figure 23B:
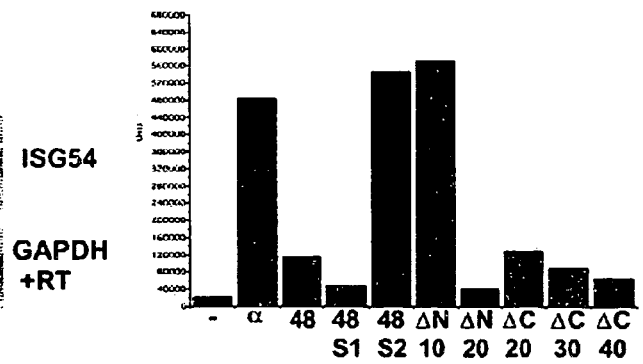

Similar results were obtained by examining endogenous ISG expression by RT-PCR analysis and are illustrated in FIGS. 23A and 23B. 293T cells were transfected for 24 hours with the TAD variants as indicated prior to RNA preparation. FIG. 23A quantifies the induction of ISG54 by p48-S2C fusions by phosphorimaging and compares the endogenous ISG54 expression of 293T cells treated with 1000 U/mol of interferon for four hours with p48, p48-S1C, p48-S2C, and the various p48-TAD variants. Partial endogenous ISG expression was retained when slight amino acid deletions from the N-terminus were made. Accordingly, depending on the level of transcriptional activity required or desired, the present invention encompasses variants of the STAT2 TAD fused with p48 protein.

Example 9

Anti-viral Effects of p48-S2C Expression

The following experiments were conducted to illustrate the anti-viral effects of p48-S2C expression. Anti-viral assays were performed for vesicular stomatitis virus (VSV), simian virus 5 (SV5), type II human parainfluenza virus (HPIV2), and Herpes simplex virus (HSV-1). These cell lines were tested for resistance to virus-induced cytopathic effects and the ability to suppress virus replication. VSV is an IFN-sensitive rhabdovirus. In contrast, SV5, HPIV2 and HSV-1, are IFN-resistant viruses. Specifically, SV5 and HPIV2, which are members of the *Rubulavirus* genus of the Paramyxovirus family of negative strand RNA viruses, evade the IFN response by targeting STAT1 and STAT2, respectively, for proteolytic degradation. Similarly, HSV-1, a DNA virus, has several strategies for evading IFN responses. Thus, the ability of the p48-S2C fusion protein to block the replication of both IFN-sensitive and IFN-resistant viruses was evaluated.

To create stably-transfected cell lines, 293 Tet-On cells were transfected with tetracycline-regulated pBI plasmids encoding the p48-S2C ORF. Individual clones were then selected and probed by anti-IRF9 immunoblotting analyses for regulated expression. In order to determine the extent of protection from viral-induced CPE, cells plated in 96 well dishes were: (i) treated with 1000 U/ml IFNα or 1 µg/ml doxycycline (Dox) for 24 hours, (ii) challenged with virus infection, and (iii) photographed and/or harvested for plaque assays. For vesicular stomatitis virus (VSV, Indiana strain), supernatants were harvested at 16 hours post infection, diluted serially (1:2) and used to inoculate fresh monolayers of U3A cells. The relative titer was then determined 24 hours later by analyzing CPE endpoint dilution by staining with methylene blue (3% in 50% ethanol).

Anti-viral assays with simian virus 5 (SV5; W3A strain) and type II human parainfluenza virus (HPIV2; Greer strain) were performed as follows: 293T cells carrying the tet-induced IRF9-S2C transgene were treated with 1 µg/ml of Dox for 24 hours. The cells were then washed with serum free medium (SFM), infected with the virus at a multiplicity of 1.0 and/or 0.1 pfu/cell for 2 hours, washed with serum free medium; and cultured for an additional 48 hours in the presence or absence of Dox in DMEM with 2% serum. The anti-viral assay using Herpes simplex virus (HSV-1) was performed similarly, except that cells were infected at a multiplicity of 5 pfu/cell. Supernatants were harvested from infected Dox-inducible p48-S2C cell lines at 24 hours pt and titered on Vero cells.

In order to determine whether p48-S2C can generate an anti-viral state that inhibits replication of both IFN-sensitive and IFN-resistant viruses, anti-viral assays were conducted in which control (UNT) or dox-treated p48-S2C Tet-On cells (DOX) were infected with VSV, SV5, HPIV2, or HSV-1. In addition, to determine the extent of protection with the p48-S2C fusion, cells were also treated with IFN (1000 U/ml IFNα for 24 hours) prior to infection.

FIG. 33 illustrates the results of the anti-viral assays. Replication of VSV was reduced 10 fold in the p48-S2C expressing cells (DOX) when compared to the cells with no Dox treatment (UNT). Specifically, VSV titer decreased from $9.6 \times 10^8$ pfu/ml for control cells to $8.7 \times 10^7$ pfu/ml following Dox induction of p48-S2C. Compared with IFN stimulation, dox induction of p48-SC2 was not quite as efficient in reducing replication and establishing an anti-viral state. VSV titer decreased from $9.6 \times 10^8$ pfu/ml for control cells to $4.3 \times 10^6$ pfu/ml following pretreatment with IFNα.

Similarly, replication of the IFN-resistant virus, SV5, was inhibited in the p48-S2C expressing cells by over 90% when compared to the cells with no Dox treatment. Specifically, SV5 titers decreased from $2.4 \times 10^6$ pfu/ml for control cells to $7.1 \times 10^4$ pfu/ml following Dox induction of p48-S2C. As with VSV infection, the anti-viral state produced by the p48-S2C fusion protein was intermediate between untreated cells and IFN-treated cells. Likewise, replication of HPIV2 was also reduced in the p48-S2C expressing cells and HPIV2 titers decreased from $2.3 \times 10^5$ pfu/ml to $7.7 \times 10^3$ pfu/ml following Dox treatment. A dramatic inhibition of HSV-1 replication was observed in cells upon p48-S2C fusion protein expression. Accordingly, the recovered viral titers were reduced from $2 \times 10^8$ pfu/ml to $2.6 \times 10^5$ pfu/ml.

These results indicate that augmenting the cellular IFN response by p48-S2C expression can inhibit the replication of diverse virus species. Indeed, the p48-S2C fusion protein is demonstrated to be an effective anti-viral for RNA and DNA viruses in spite of virus-encoded IFN resistance. Specifically, because SV5, HPIV2 and HSV-1 have several strategies for evading IFN responses, the ability to inhibit their replication is a powerful demonstration that the hybrid p48 fused to a transcriptional activation domain (TAD) strategy can overcome numerous intrinsic virus-associated anti-IFN strategies.

Example 10

Inhibition of Hepatitis C Virus Replicon by p48-TAD Hybrid Fusion Proteins

The hepatitis C virus is difficult to treat by IFN combination therapy because of the resistance developed by many genotypes. Accordingly, the following experiment was conducted to determine the inhibition of Hepatitis C virus replicon by the p48, p48-S1C, p48-S2C, and p48-VP16 TAD constructs.

For this experiment, an HCV replicon-containing cell line was transfected with 0.5 or 1.0 micrograms of plasmid expression vectors for p48, p48-S1C, p48-S2C, p48-VP16, or control anti-viral gene ISG54, respectively, and cell extracts were prepared 48 hours later. Equal amounts of extract (20 micrograms total protein) for each condition were separated on SDS-PAGE and proteins were transferred to membranes for immunoblotting with antiserum specific for the HCV protein NS5A (top panel), p48 (center panel), or cellular protein actin (bottom panel). While p48 or p48-S1C fusion had no effect on NS5A accumulation level, a dose-dependent reduction in NS5A accumulation was observed with both the p48-S2C and p48-VP16 fusion constructs. Actin expression verifies equal loading of all samples. This result demonstrated the effectiveness of p48-S2C as an inhibitor of Hepatitis C virus replication activity.

Example 11

The Effect of IFN Neutralizing Antibodies on SV5 Anti-viral Assays

This example describes the evaluation of the effects of IFN neutralizing antibodies on SV5 anti-viral assays. For the experiments carried out in this example, cells were pretreated with Dox or 200 U/ml IFNα for 24 hours in the presence or absence of 400 neutralizing units of anti-IFNα and anti-IFNβ antibodies (PBL Biomedical Laboratories). Cells were then infected as described supra in Example 9, and cultured for 48 hours in the continued presence of either Dox to express the p48-S2C fusion protein or IFN and the anti-IFN antibodies. Supernatants were then titered in plaque assays using simian CV-1 cells with an overlay containing 0.5% agar with DMEM and 10 mM HEPES (pH 7.2). The monolayer was fixed in 3.7% formaldehyde and stained with 0.1% crystal violet (Sigma) dissolved in 20% EtOH.

The protective effects of IFN during virus infection rely in part on autocrine and paracrine signaling through newly-synthesized IFN. Virus infection can activate IRF3 and IRF7 transcription factors that induce the synthesis and secretion of IFNβ and IFNα, which in turn can activate ISGF3 signaling in the infected cells as well as in adjacent cells to amplify the anti-viral response. To determine whether the mechanism of protection provided by the p48-S2C expression relied on IFN production, anti-viral assays for SV5 were performed in the continued presence of IFN-neutralizing antibodies.

Figure 35:
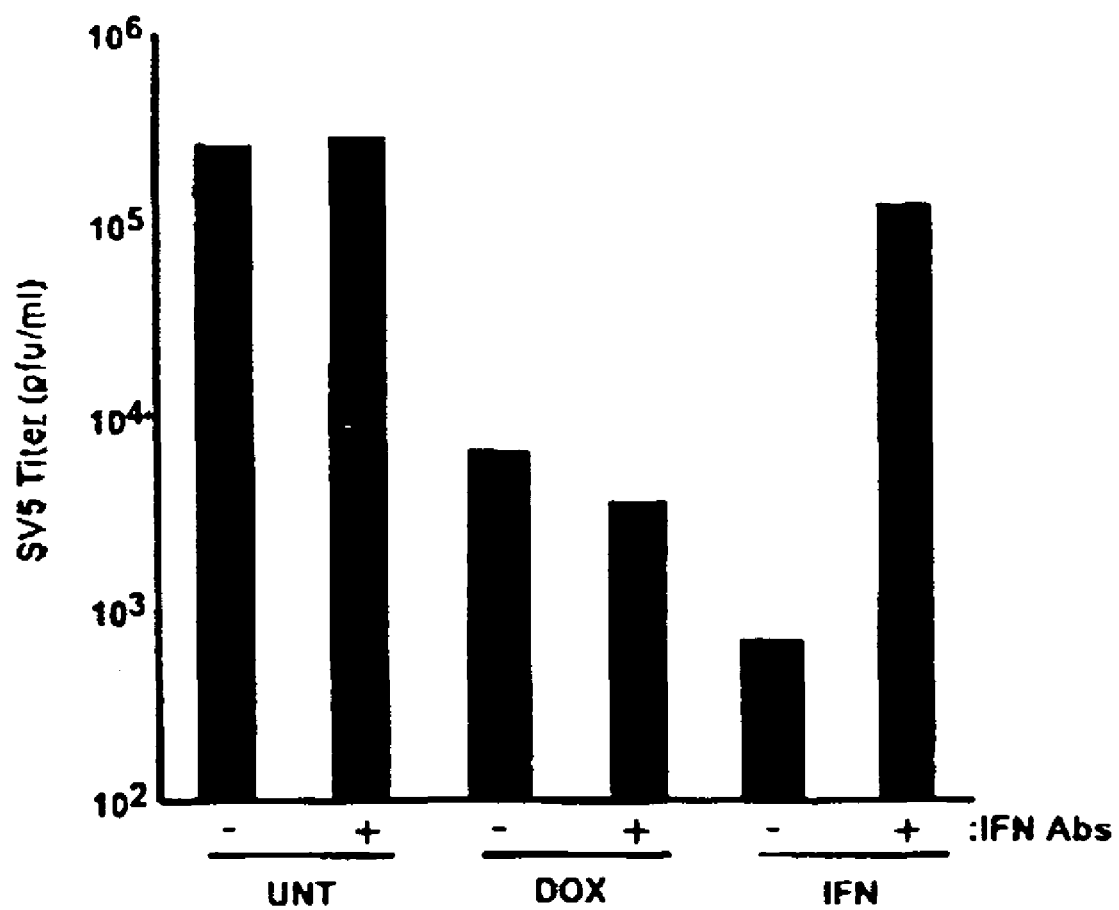
FIG. 35 illustrates the effect of autocrine IFN on the anti-viral state induced by p48-S2C.

FIG. 35 illustrates the effect of IFN neutralizing antibodies on IFN and Dox treated cells. While a 24 hour pretreatment of cells with IFN resulted in a protective anti-viral state as indicated by the reduction in SV5 infectious titer, the addition of IFN-neutralizing antibodies (indicated in FIG. 35 by a (+) IFN abs.) significantly reduced the establishment of the cellular anti-viral state. Pretreatment with Dox to express the p48-S2C transgene for 24 hours before infection also produced an anti-viral state, but with a somewhat lower efficiency than was observed with IFN treatment. However, in contrast to the results with IFN treatment, the addition of IFN-neutralizing antibodies beginning at the time of Dox treatment did not significantly alter the p48-S2C induced anti-viral state, thus indicating that the anti-viral effects are due to p48-S2C transcriptional activity rather than to autocrine/paracrine signaling downstream of induced IFN synthesis.

The contents of all patents, patent applications, published articles, books, reference manuals, abstracts and the Sequence Listings, as cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A hybrid fusion polypeptide selected from the group consisting of the amino acid sequence set forth in SEQ ID NO: 2; and the amino acid sequence set forth in SEQ ID NO: 30.

2. A composition comprising the polypeptide according to claim 1 and a pharmaceutically acceptable carrier, excipient, or diluent.

3. A method of producing the hybrid interferon fusion polypeptide according to claim 1, comprising:
   (a) introducing into a host cell, a recombinant expression system containing an open reading frame (ORF) having a polynucleotide sequence which encodes the hybrid fusion polypeptide, wherein the vector is designed to express the ORF in the host cell, and
   (b) culturing the host cell under conditions resulting in the expression of the ORF sequence.

4. A method of administering the polypeptide according to claim 1 to a host cell comprising, contacting the host cell with the composition.

5. A method of administering the composition according to claim 2 to a host cell comprising, contacting the host cell with the composition.

* * * * *